(12) United States Patent
Ochiai

(10) Patent No.: US 7,927,845 B2
(45) Date of Patent: Apr. 19, 2011

(54) FATTY ACID SYNTHETASE, POLYNUCLEOTIDE ENCODING THE SAME, AND USES THEREOF

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 29 days.

(21) Appl. No.: 12/299,662

(22) PCT Filed: May 8, 2007

(86) PCT No.: PCT/JP2007/059815
§ 371 (c)(1),
(2), (4) Date: Nov. 5, 2008

(87) PCT Pub. No.: WO2007/129770
PCT Pub. Date: Nov. 15, 2007

(65) Prior Publication Data
US 2009/0325162 A1    Dec. 31, 2009

(30) Foreign Application Priority Data

May 8, 2006   (JP) .................................. 2006-128779

(51) Int. Cl.
*C12P 7/64* (2006.01)
*C12N 1/00* (2006.01)
*C07H 21/04* (2006.01)

(52) U.S. Cl. ................ 435/134; 435/252.3; 435/252.33; 435/254.1; 435/320.1; 435/183; 536/23.2

(58) Field of Classification Search ........................ None
See application file for complete search history.

(56) References Cited

U.S. PATENT DOCUMENTS

| 2004/0172681 A1 | 9/2004 | Voelker et al. |
| 2005/0191679 A1 * | 9/2005 | Metz et al. .......................... 435/6 |
| 2008/0138874 A1 | 6/2008 | Ochiai et al. |

FOREIGN PATENT DOCUMENTS

| JP | 8-205900 | 8/1996 |
| JP | 2001-245687 | 9/2001 |
| JP | 2005-287403 | 10/2005 |
| WO | 01/40514 | 6/2001 |

OTHER PUBLICATIONS

"Schizosaccharomyces pombe fatty acid synthase subunit alpha" XP-002450605, retrieved from EBI, Database Acc. No. ADQ26426 (2004).
Takeno et al. "Transformation of Oil-Producing Fungus, *Mortierella alpina* 1S-4, Using Zeocin, and Application to Arachidonic Acid Production" *J. Biosci. Bioengineer*. 100(6):617-22 (2005).
Schweizer et al. "Microbial Type I Fatty Acid Synthases (FAS): Major Players in a Network of Cellular FAS Systems" *Microbiol. Mol. Biol. Rev.* 68(3):501-517 (2004).
Karlin et al. "Methods for assessing the statistical significance of molecular sequence features by using general scoring schemes" *Proc. Natl. Acad. Sci. USA* 87:2264-2268 (1990).
Karlin et al. "Applications and statistics for multiple high-scoring segments in molecular sequences" *Proc. Natl. Acad. Sci. USA* 90:5873-5877 (1993).
Zoller et al. "Oligonucleotide-directed mutagenesis using M13-derived vectors: an efficient and general procedure for the production of point mutations in any fragment of DNA" *Nuc. Acids Res.* 10(20):6487-6500 (1982).
Dalbadie-McFarland et al. "Oligonucleotide-directed mutagenesis as a general and powerful method for studies of protein function" *Proc. Natl. Acad. Sci. USA* 79:6409-6413 (1982).
Carter et al. "Improved oligonucleotide site-directed mutagenesis using M13 vectors" *Nuc. Acids Res.* 13(12):4431-4443 (1985).
Kunkel, T.A. "Rapid and efficient site-specific mutagenesis without phenotypic selection" *Proc. Natl. Acad. Sci. USA* 82:488-492 (1985).
Stoops et al. "Studies on the Yeast Fatty Acid Synthetase" *J. Biol. Chem.* 253(12):4464-4475 (1978).
Struhl et al. "High-frequency transformation of yeast: Autonomous replication of hybrid DNA molecules" *Proc. Natl. Acad. Sci. USA* 76(3):1035-1039 (1979).
Karin et al. "Primary structure and transcription of an amplified genetic locus: The *CUP1* locus of yeast" *Proc. Natl. Acad. Sci. USA* 81:337-341 (1984).
Mackenzie et al. "Isolation and Use of a Homologous Histone H4 Promoter and a Ribosomal DNA Region in a Transformation Vector for the Oil-Producing Fungus *Mortierella alpine*" *Appl. Environ. Microbiol.* 66(11):4655-4661 (2000).
Hinnen et al. "Transformation of yeast" *Proc. Natl. Acad. Sci. USA* 75(4):1929-1933 (1978).
Ito et al. "Transformation of Intact Yeast Cells Treated with Alkali Cations" *J. Bacteriol.* 153(1):163-168 (1983).
English language Abstract of JP 2001-245687, (Sep. 11, 2001).
English language Abstract of JP 8-205900, (Aug. 13, 1996).
English language Abstract of JP 2005-287403, (Oct. 20, 2005).

* cited by examiner

*Primary Examiner* — Nashaat T Nashed
(74) *Attorney, Agent, or Firm* — Greenblum & Bernstein, P.L.C.

(57) ABSTRACT

The present invention provides fatty acid synthetases which are responsible for novel fatty acid synthesis, polynucleotides which encode such fatty acid synthetases (e.g., a polynucleotide comprising (a) a polynucleotide consisting of the nucleotide sequence of Positions 1 to 12486 of SEQ ID NO: 1, or (b) a polynucleotide which hybridizes under stringent conditions to a polynucleotide comprising a nucleotide sequence complementary to the nucleotide sequence of Positions 1 to 12486 of SEQ ID NO: 1, and which encodes a protein having a fatty acid synthetase activity), expression vectors and transformants comprising such polynucleotides, methods for producing food and other products using such transformants, food products produced by such methods, and methods for assessing and selecting lipid-producing test fungi.

14 Claims, 5 Drawing Sheets

Fig. 1-1

| | | |
|---|---|---|
| Saccharomyces cerevisiae | 1 | ------------MDAYSTRPLTLSHGSLEHVLLYPTASFFIASQLQEQFNKIILPEPTEGFAADDEPTTPAELVGKFLGVVSSLVEPS----KVGGFDQ 100 |
| Candida albicans | | ------------MSTHRPFQLTHGSIEHTLLVPNDLFFNYSGLKDEFIKTLPEPTEGFAGDDEPSSPAELYGKFIGFISNAQFP-----------q |
| Aspergillus nidulans | | MYGTSTGPQTGINTPRSSQSLRPLILSHGSLEFSFLVPTSLHFHASQLKDTFTASLPEPTDELAQDDEPSSVAELVARYIGHVAHEVEEGEDDAHGTNQD |
| Saccharomyces cerevisiae | 101 | VLNLCLTEFENCYLEGNDIHALAAKLLQENDTTLVKTKELIKNYITARIMAKRPFDKSNSALFRAVGEGNAQLVAIFGGQGNTDDYFEELRDLYQTYHV 200 |
| Candida albicans | | IVELSLKDFESRFLDNNNDNIHSFAVKLLDDETYPTTIAKVKENIVKNYYKAVKSINKVESNLLYHCKH-DAKLVAIFGGQGNTDDYFEELRELYTLYQG |
| Aspergillus nidulans | | VLKLTLMEFERAFMRGNDVHAVAATLPGIITAKKVLVVEAYYAG------RAAAGRPTKP-YDSALFRAASDEKARIYSVLGGQGNIEEYFDELREVYNTYIS |
| Saccharomyces cerevisiae | 201 | LVGDLIKFSAETLSELIRTTLDAEKVFTQGLNIILEMILENPSNTPDKDYLLSIPIISQPLIGVIQLAHYVVTAKLLGFTPGELRSYLKGATGHSQGLVTAVA 300 |
| Candida albicans | | LIEDLLVSIAEKLNQLHPS------FDKIYTQGLNILSWLKHPETTPDQDYLESVPVSQPVICVIQLCHYTITCKVLGLTPGEFRNSLKWISTGHSQGLVTAVT |
| Aspergillus nidulans | | FVDDLISSSAELLQSLSREP-DANKLYPKGLNVMQWLREPDTQPDVDYLVSAPVVSLPLIGLVQLAHFAVTCRVLGKEPGEILERFSGTTGHSQGIVTAAA |
| Saccharomyces cerevisiae | 301 | IAETDSWESFFVSVRRKAITVLFFIGVRCYEAYPNTSLPPSILEDSLENNEGVPSPMLSISNLTQEQVQDYVNKTNSHLPAGKQVEISLVNGAKNLVVSGP 400 |
| Candida albicans | | IAASDSWDSFLKNSLTAVSLLLFIGSRCLSTYPRTSLPPTMLQDSLDNGEGRPSPMLSVRDLSIKQVEKFIEQTNSHLPREKHIAISLINGARNLVLSGP |
| Aspergillus nidulans | | IATATTMESFHKAVANALTMLFWIGLRSQQAYPRTSIAPSVLQDSIENGEGTPTPMLSIRDLPRTAVQEHIDMITNQHLPEDRHISISLVNSARNFVVTGP |
| Saccharomyces cerevisiae | 401 | PGSLYGLNLTLRKAKAPSGLDQSRIPFSERKLKFSNRFLPVASPFHSHLLVPASDLINKDLVKNNVSFNAKDIQIPYDTFDGSDLRVLSGS-ISERIVD 500 |
| Candida albicans | | PESLYGFNLNLRNQKAPMGLDQSRYPFSERKLKCSNRFLPIFAPFHSHLLADATELILDDVKEHGLSFEG--LKIPVYDTFDGSDFQALKEP-ILDRVVK |
| Aspergillus nidulans | | PLSLYGLNLRLRKVKAPTGLDQNRYPETQRKVRFVNRFLPIIAPFHSQYLIAPFHSQYLYSAFDRIMEDLEDVEISPKS--LTIPYYGTKIGDDLRAISDANVVPALVR |

Fig.1-2

```
                                                                                                                                      600
Saccharomyces cerevisiae   501 CIIRLPVKWETTTQFK-ATHILDFGPGGASGLGVLTHRNKDGTGVRVIVAGTLDIN-PDDDYGFKQEIFDVTSN-GLKKNPNWILEEYHPKLIKNKSGKIF
            Candida albicans       LITELPVHWEEATNHK-ATHILDFGPGGVSSGLGVLTHRNKEGTGARIILAGTLDSNPIDDEYGFKHEIFQTSADKAIKWAPDWLKELRPTLVKNSEGKIY
           Aspergillus nidulans    MITHDPVNWEQTTAFPNATHIVDFGPGGISGLGVLTNRNKDGTGVRVILAGSMDGT—NAEVGYKPELFDRDEH-SVKYAIDWVKEYGPRLVKNATGQTF
                                                                                                                                      700
Saccharomyces cerevisiae   601 VETKFSKLIGRPPLLVPGMTPCTVSPDFVAAITNAGYTIELAGGGYFSAAGMTAAIDSVVSQIEKGSTFGINLIYNPFMLQWGIPLIKELRSKGYPIQF
            Candida albicans       VKTKFSQLLGRAPLMVAGMTPTTVNTDIVSASLNAGYHIELAGGGYFSPVMMTRAIDDIVSRIKPGYGLGINLIYNPFMLQWGIPLIKDLREKGYPIGS
           Aspergillus nidulans    VDTKMSRLLGIPPIMVAGMTPTTVPNDFVAATMNAGYHIELAGGGYYNAKTMTEAITKIEKAIPPGRGITVNLIYNPRAMGWQIPLIGKLRADGVPIEG
                                                                                                                                      800
Saccharomyces cerevisiae   701 LTIGAGVPSLEVASEYIETLGLKYLGLKPGSIDAISQVINIAKAHPNFPIALQWTGGRGGGHHSFEDAHTPMLQMYSKIRRHPNIMLIFGSGFGSADDTY
            Candida albicans       LTIGAGVPSIEVATEYIEDLGLTHLGLKPGSVDAISQVIAIAKAHPTFPIVLQWTGGRGGGHHSFEDFHQPIIQMYSKIRRCSNIVLVAGSGFGSDEDTY
           Aspergillus nidulans    LTIGAGVPSIEVANEYIETLGIKHIAFKPGSSVDAIQQVINIAKANPKFPVILQWTGGRGGGHHSFEDFHQPILQMYSRIRRHENIILVAGSGFGGAEDTY
                                                                                                                                      900
Saccharomyces cerevisiae   801 PYLTGEWSTKFDYPPMPFDGFLFGSRVMIAKEVKTSPDAKKCIAACGTGVPDDKWEQTYKRPTGGIVTVRSEMGEPIHKIATRGVMLWKEFDETIFNLPKN
            Candida albicans       PYLSGYWSEKFNYPPMPFDGVLFGSRVMTSKESHTSLAAKKLIVECGKGVPDQQWEQTYKRPTGGIITVRSEMGEPIHKIATRGVMFWKELDDTIFNLPKN
           Aspergillus nidulans    PYLSGNWVSSRFGYPPMPFDGGLFGSRMMTAKEAHTSKNAKGAIVDAPGLDDQDWEKTYKGAAGGVVTVLSEMGEPIHKLATRGVLFWHEMDQKIFKLDKA
                                                                                                                                      1000
Saccharomyces cerevisiae   901 KLVPTLEAKRDYIISRLNADFGKPWFATV-NGQARDLATMTYEEVAKRLVELMFIRSTNSWFDVTWRTFTGDFLRRVEERFTKSK-TLSLIQSYSLLDKP
            Candida albicans       KLLDALNKKRDHIIKKLNNDFGKPWFGKN-ANGVCDLQEMTYKEVANRLVELMYVKKSHRWIDVSLRNMYGDFLRRVEERFTSSAGTVSLLQNFNQLNEP
           Aspergillus nidulans    KRVPELKKQRDYIIKKLNDDFGKVWFGRNSAGETVDLEDMTYAEVVHRMVDLMYYKHEGRWIDDSLKKLTGDFIRRVEERFTTAEGQASLLQNYSELNVP
```

Fig.1-3

```
                              1001                                                                                              1100
Saccharomyces cerevisiae      DEAIEKVFNAYPAAREQFLNAQDIDHFLSMCQNPMQKPVPFVPVPVLDRRFEIFFKKDSLWQSEHLEAVVDQDVQRTCILHGPVAAQFTKVIDEPIKSLMDG
Candida albicans              EQFTADFFEKFPQAGKQLLSEEDCDYFLMLAARPGGKPVPFVPVPVLDERFEFFEKKDSLWQSEDLESVVDEDVQRTCILHGPVASQYTSKVDEPIGDILNS
Aspergillus nidulans          YPAVDNILAAYPEAATQLINAQDVQHFLLLGQRRGGKPVPFVPSLDENFEYWFKKDSLWQSEDLEAVVGQDVGRTCILQGPMAAKFSTVIDEPVGDILNS 1101                                                                                              1200
Saccharomyces cerevisiae      IHDGHIKKLLHQYYGDDESKIPAVEYFGGES---------PVDVQSQVDSSSVSEDSAVFKATSSTDEESWFKALAGSEINWRHASFLCGSFITQDKMFVSNP
Candida albicans              IHEGHIARLIKEEYAGDESKIPVVEYFGGKK---------PASVSATSVNIIDGNQVVYEIDSELPNKGEWIDLLAGTELNWLQAFISTDRIVGGSKHVSNP
Aspergillus nidulans          IHQGHIKSEIKDMYNGDETTIPITEYFGGRLSEAQEDIEMDGLTISEDAMKISYRLSSSAADLPEVNRWCRLLAGRSYSWRHALFSADVFVQGHRFQTNP 1201                                                                                              1300
Saccharomyces cerevisiae      IRKVFKPSQGMVVEISMGNTSSKTVWTLSEPVQG-ELKPTVILKLLKENITQMEMIENRTMDGKPVSLPLLYNFNPDNGFAPISEVMEDRNGRIKEMYWK
Candida albicans              LHDILTPAKHSKVTID-------KKTKKLTAFENIKG-DLLPVVEIELVKPNTIQLSLIEHRTADTNPVALPFLYKYNPADGFAPILEIMEDRNERIKEFYWK
Aspergillus nidulans          LKRVLAPSTGMVVEIANPEDAPKTVISVREPYGSGKLVKTVDIKLNEKGPIALTLYEGRTAENGVVPLTELFTYHPDTGYAPIREVMDSRNDRIKEFYYR 1301                                                                                              1400
Saccharomyces cerevisiae      LWID--EPFNLDFDPRDVIKGKOFEITAKEVDFTHAVGNNNCEDFVSRPDRTMLAPMDFAIVVGWIRAIIKAIFPNTVDGDLKLVHLSNGYKMIPGAKPL
Candida albicans              LWFGSSVPYSNDINVEKAILGDEITLSSQTISEFTHAIGNIKGDAFVDRPGKATLAPMDFAIVIGNKAIIKAIFPKSVDGDLLKLVHLSNGYKMITGAAPL
Aspergillus nidulans          IWFG-NKDVPFYTPTTATFNGGRETIISQAVADFVHAVGNTGEAFVERPGKEVFAPMDFAIVAGWKAITKPIFPRTIDGDLKLVHLSNGFKMVPGAQPL 1401                                                                                              1500
Saccharomyces cerevisiae      QVGDVVSTTAVIESVVAQPTGKIVDVWGTLSRNGKPVMEVTSSFFYRGNYTDFENTFQKTVEPVYGMHIKTSKDIAVLRSKEWFQLDDEDFDLLNKTLTF
Candida albicans              KKGDVVSTKAELKAVLNQPSGKLVEWVGTIYREGKPVMEVTSQFLYRGEYANDYQNTFQKVTETPVGVAFKSAKDLAVLRSKEWFHL--EKD--VQFDVLTF
Aspergillus nidulans          KVGDVLDTTAQINSIINEESGKIVEVCGTIRRDGKPIMHVTSQFLYRGAYTDFENTFQRKDEVPMQVHLASSRDVAILRSKEWFRLDMDDVELLGQTLTF
```

Fig. 1-4

```
                              1501                                                                                                  1600
Saccharomyces cerevisiae      ETETEVTFKNANIFSSVKCFGPIKVELPTKETVEIGIVDYEAGASHGNPVVDFLKRNGSTLEQKVNLENPIPIA---VLDSYTPSTNEPYARVSGDLNPI
        Candida albicans     RCESTYKFKSANVYSSIKTTGGVLLELPTKEVIQVGSVDYEAGTSYGNPVTDYLSRNGNKTIEESVIFENAIPLSSGEELTSKAPGTNEPYAIVSGDYNPI
      Aspergillus nidulans    RLQSLIRFKNKNVFSQVQTMGGVLLELPTKEVIQVASVDYEAGTSHGNPVIDYLQRNGTSIEQPVYFENPIPLSGKTPLVLRAPASNETYARVSGDYNPI 1601                                                                                                  1700
Saccharomyces cerevisiae      HVSRHFASYANLPGTIIHGMFSSASVRALIENWHAADSVSSRVRGYTCQFVDMVLPNTALKTSIQHVGMINGRKLIKFETR-NEDDVVVLTGEAEIEQPVT
        Candida albicans     HVSRVFAAYAKLPGTIIHGMYSSASIRALVEEWAANNVAARVRAFKCDFVGMVLPNDTLQTMEHVGMINGRKIIKVETRNVETELPVLIGEAEIEQPTT
      Aspergillus nidulans    HVSRVFSSYANLPGTIIHGMYTSAAVRSLVETWAAENNIGRVRGFHVSLVDMVLPNDLITVRLQHVGMIAGRKIIKVEASNKETEDKVLLGEAEVEQPVT 1701                                                                                                  1800
Saccharomyces cerevisiae      TFVFTGQGSQEQGMGMDLYKTSKAAQDVWNRADMNHFKDTYGFSILDIVINNPVNLTIHFGGEKGKRJRENYSAMIFETIVDG-KLKTEKIFKEINEHSTS
        Candida albicans     TYVFTGQGSQEQGMGMELYNSSEVAREVWDKADRHFVMNYGFSILDIVQNNPNELTIHFGGAKGRAIRDNYIGMMFETIGEDGALKSEKIFKDIDETTTS
      Aspergillus nidulans    AYVFTGQGSQEQGMGMELYATSPVAKEVWDRPSFHWN—YGLSIIDIVKNNPKERTVHFGGPRGKAIRQNYMSMTFETVNADGTIKSEKIFKEIDETTTS 1801                                                                                                  1900
Saccharomyces cerevisiae      YTFRSEKGLLSATQFTQPALTLMEKAAFEDLKSKGLIPADATFAGHSLGEYAALASIADVWSIESLVEVVFYRGMTMQVAVPRDELGRSNYGMIAINPGR
        Candida albicans     YTFVSPTGLLSATQFTQPALTLMEKAAYEDIKSKGLIPSDIMFAGHSLGEYSALSSLANVWPIESLVDVVFYRGMTMQVAVPRDELGRSNYGMVAVNPSR
      Aspergillus nidulans    YTYRSPTGLLSATQFTQPALTLMEKASFEDMRSKGLVQRDSSFAGHSLGEYSALADLADVWLIESLVSVVFYRGLTMQVAVERDEQGRSNYSMCAVNPSR 1901                                                                                                  2000
Saccharomyces cerevisiae      VAASFSQEALQYVVERVGKRTGWLVEIVAYNVENQQYVAAGDLRALDTVTNVLNFIKLQKIDIIELQKSLSLEEVEGHLFEIIDEASKKSAVKPRPLKLE
        Candida albicans     VSATFDDSALRFVDEVANKTKWLLEIVAYNVENQQYVAAGDLRALDTLTNVLNVLKINKIDIVKLQEQMSIEKVKEHLYEIVDEVAAKSLAKPGPIDLE
      Aspergillus nidulans    ISKTFNEQALQYVVGNISEQTGWLLEIVAYNVANWQYVAAGDLRALDCLTNLLNYLKAQNIDIPALMQSMSLEDVKAHLVNIIHECVKQTEAKPKPINLE
```

Fig.1-5

```
                    2001                                                                                                                        2100
Saccharomyces cerevisiae    RGFACIPLVGISVPFHSTYLMNGVKPFKSFLKKNLIKENWKVARLAGKYIPNLTAKPFQVTKEYFQDVYDLTGSEPIKEIIDNWEKYEQS----
       Candida albicans    RGFAVIPLKGISVPFHSSYLMSGVKPFQRFLCKKIPKSSVKPQDLIGKYIPNLTAKPFELTKEYFQSVYDLTKSEKIKSILDNWEQYE----
    Aspergillus nidulans    RGFATIPLKGIDVPFHSTFLRSGVKPFRSFLIKKINKTTIDPSKLVGKYIPNVTARPFEITKEYFEDVYRLTNSPRIAHILANWEKYEEGTEGGSRHGGT 2101
Saccharomyces cerevisiae    ----
       Candida albicans    ----
    Aspergillus nidulans    TAASS
```

FATTY ACID SYNTHETASE, POLYNUCLEOTIDE ENCODING THE SAME, AND USES THEREOF

TECHNICAL FIELD

The present invention relates to a gene which encodes fatty acid synthetase, and the uses thereof.

BACKGROUND ART

Fatty acid synthetase genes which are responsible for novel fatty acid synthesis have been cloned in a variety of organisms and thoroughly studied (e.g., Non-Patent Document 1: E. Schweizer et al., Microbiol. Mol. Biol. Rev., 68, 501-517 (2004)).

In some bacteria and in fungi and animals, so-called "type I" multifunctional enzymes such as those shown below are known to catalyze a series of reactions in fatty acid synthesis.

Type Ia: (Fungi) AC-ER-DH-MPT/ACP-KR-KR-KS-PPT, $\alpha_6\beta_6$ ($\beta+\alpha$: approx. 3,950 amino acids). (Bacteria) AC-ER-DH-MPT-ACP-KR-KS-PPT, $\alpha_6$, structure in which the $\beta$ and $\alpha$ subunits of fungal fatty acid synthetase (FAS) are connected head-to-tail ($\alpha$: approx. 3,000 amino acids).

Type Ib: (Animals) KS-AT-DH-ER-KR-ACP-TE, $\alpha_2$ ($\alpha$: approx. 2,500 amino acids). The above abbreviations stand for the following:

AC: ac(et)yltransferase
AT: malonyl/acetyl-transferase
MPT: malonyl/palmitoyl-transferase
KS: ketoacyl synthase
KR: ketoacyl reductase
DH: dehydratase
ER: enoyl reductase
ACP: acyl carrier protein
TE: thioesterase
PPT: palmitoyl/palmitoyl-transferase.

In the yeast *Saccharomyces cerevisiae* (also abbreviated below as "*S. cerevisiae*"), novel fatty acid synthesis is carried out by a fatty acid synthetase (an α6β6 complex composed of β subunits encoded by a FAS1 gene and α subunits encoded by a FAS2 gene) up to 18 carbons (stearic acid). In addition, ELO1, ELO2 and ELO3 are known as fatty acid elongase genes. It is thought that ELO1 is responsible for extending the length of C12 to C16 chains to from C16 to C18, ELO2 is responsible for extending the length of C16 to C18 chains to C22, and ELO3 is responsible for extending the length of C18 to C24 chains to C26.

At the same time, the fact that, in the lipid-producing fungus *Mortierella alpina* (also abbreviated below as "*M. alpina*"), a mutant strain having a lowered fatty acid elongation activity from palmitic acid to stearic acid can be obtained by mutagenic treatment (Patent Document 1: Japanese Patent Application Laid-open No. 2001-245687) suggests that, at the very least, different enzymes are responsible for synthesis up to palmitic acid and for synthesis from palmitic acid to stearic acid.

However, the fatty acid synthetase genes which are responsible for novel fatty acid synthesis in lipid-producing fungi such as *M. alpina* have not previously been cloned.

DISCLOSURE OF THE INVENTION

In light of the above, there has existed a desire to identify the fatty acid-synthesizing enzymes which are responsible for novel fatty acid synthesis in fatty acid-producing fungi such as *M. alpina* and the genes which encode for such enzymes.

The inventors have conducted extensive investigations, as a result of which they have succeeded in cloning the a fatty acid synthetase gene responsible for novel fatty acid synthesis in the lipid-producing fungus *M. alpina* and have ultimately arrived at the present invention. Accordingly, the invention provides the following polynucleotides, proteins, expression vectors, transformants, methods for producing foods and other products using such transformants, foods and other products produced by such methods, and methods for assessing and selecting lipid-producing test fungi.

(1) A polynucleotide selected from any one of the following (a) to (h):

(a) a polynucleotide comprising a polynucleotide consisting of the nucleotide sequence of Positions 1 to 12486 of SEQ ID NO: 1;

(b) a polynucleotide comprising a polynucleotide consisting of the nucleotide sequence of SEQ ID NO: 2 or a part thereof;

(c) a polynucleotide comprising a polynucleotide encoding a protein having the amino acid sequence of SEQ ID NO: 3;

(d) a polynucleotide comprising a polynucleotide encoding a protein which consists of an amino acid sequence of SEQ ID NO: 3 in which one or more amino acids are deleted, substituted, inserted and/or added, and which has a fatty acid synthetase activity;

(e) a polynucleotide comprising a polynucleotide encoding a protein having 60% or higher identity with the amino acid sequence of SEQ ID NO: 3, and which has a fatty acid synthetase activity;

(f) a polynucleotide comprising a polynucleotide which hybridizes under stringent conditions to a polynucleotide consisting of a nucleotide sequence complementary to the nucleotide sequence of Positions 1 to 12486 of SEQ ID NO: 1, and which encodes a protein having a fatty acid synthetase activity;

(g) a polynucleotide comprising a polynucleotide which hybridizes under stringent conditions to a polynucleotide consisting of a nucleotide sequence complementary to the nucleotide sequence of SEQ ID NO: 2 or a part thereof, and which encodes a protein having a fatty acid synthetase activity; and (h) a polynucleotide comprising a polynucleotide which hybridizes under stringent conditions to a polynucleotide consisting of a nucleotide sequence complementary to the nucleotide sequence of a polynucleotide encoding a protein consisting of the amino acid sequence of SEQ ID NO: 3, and which encodes a protein having a fatty acid synthetase activity.

(2) The polynucleotide of (1) above which is selected from any one of following (i) to (m):

(i) a polynucleotide comprising a polynucleotide encoding a protein which consists of an amino acid sequence of SEQ ID NO: 3 in which one to ten amino acids are deleted, substituted, inserted and/or added, and which has a fatty acid synthetase activity;

(j) a polynucleotide comprising a polynucleotide encoding a protein having 90% or higher identity with the amino acid sequence of SEQ ID NO: 3, and which has a fatty acid synthetase activity;

(k) a polynucleotide comprising a polynucleotide which hybridizes under highly stringent conditions to a polynucleotide consisting of a nucleotide sequence complementary to the nucleotide sequence of Positions 1 to 12486 of SEQ ID NO: 1, and which encodes a protein having a fatty acid synthetase activity;

(l) a polynucleotide comprising a polynucleotide which hybridizes under highly stringent conditions to a polynucleotide consisting of a nucleotide sequence complementary to the nucleotide sequence of SEQ ID NO: 2 or a part thereof, and which encodes a protein having a fatty acid synthetase activity; and (m) a polynucleotide comprising a polynucleotide which hybridizes under highly stringent conditions to a polynucleotide consisting of a nucleotide sequence complementary to the nucleotide sequence of a polynucleotide encoding a protein consisting of the amino acid sequence of SEQ ID NO: 3, and which encodes a protein having a fatty acid synthetase activity.

(3) The polynucleotide of (1) above, comprising a polynucleotide which consists of the nucleotide sequence of Positions 1 to 12486 of SEQ ID NO: 1.

(4) The polynucleotide of (1) above, comprising a polynucleotide which consists of the nucleotide sequence of SEQ ID NO: 1.

(5) The polynucleotide of (1) above, comprising a polynucleotide which consists of the nucleotide sequence of SEQ ID NO: 2.

(6) The polynucleotide of (1) above, comprising a polynucleotide which encodes a protein consisting of the amino acid sequence of SEQ ID NO: 3.

(7) The polynucleotide of any one of (1) to (6) above which is DNA.

(8) A protein encoded by the polynucleotide of any one of (1) to (7) above.

(8a) A protein which comprises the amino acid sequence of SEQ ID NO: 3.

(8b) A protein which comprises an amino acid sequence of SEQ ID NO: 3 in which one or more amino acids are deleted, substituted, inserted and/or added, and which has a fatty acid synthetase activity.

(8c) A protein having 60% or higher identity with the amino acid sequence of SEQ ID NO: 3, and which has a fatty acid synthetase activity.

(9) A vector comprising the polynucleotide of any one of (1) to (7) above.

(9a) The vector of (9) above which comprises an expression cassette comprising the following components (a) to (c):
 (a) a promoter which can transcribes in a host cell;
 (b) the polynucleotide of any one of (1) to (7) above which is joined to the promoter; and
 (c) a signal which functions within a host cell in connection with the transcription termination and polyadenylation of an RNA molecule.

(9b) The vector of (9a) above wherein the host cell is a lipid-producing fungus (e.g., *M. alpina*) or a yeast (e.g., *S. cerevisiae*).

(10) A transformed organism having introduced therein the polynucleotide of any one of (1) to (7) above.

(11) A transformed organism having introduced therein the vector of (9) above.

(12) The transformed organism of (11) above having an increased fatty acid-forming ability owing to introduction of the vector of (9) above.

(13) The transformed organism of any one of (10) to (12) above, wherein the organism is a fatty acid-producing fungus.

(14) The transformed organism of (13) above, wherein the fatty acid-producing fungus is *Mortierella alpina*.

(15) A method for producing a lipid or fatty acid using the transformed organism of any one of (10) to (14) above.

(16) A method for producing a food, drug or industrial material using the transformed organism of any one of (10) to (14) above.

(16a) The production method of (16) above, wherein the food is an oil and fat-containing food.

(17) A food, drug or industrial material produced by the method of (16) above.

(17a) The food or industrial material of (17) above, wherein the food is an oil and fat-containing food.

(18) A method for assessing the fatty acid-forming ability of a lipid-producing test fungus, which comprises use of a primer or probe designed based on the nucleotide sequence of a fatty acid synthetase gene having the nucleotide sequence of Positions 1 to 12486 of SEQ ID NO: 1.

(18a) A method for selecting, by the method of (18) above, a lipid-producing fungus having a high fatty acid-forming ability.

(18b) A method for producing an oil and fat using the lipid-producing fungus selected by the method of (18a) above.

(19) A method for assessing the fatty acid-forming ability of a lipid-producing test fungus, comprising culturing a lipid-producing test fungus and measuring an expression level of a fatty acid synthetase gene having the nucleotide sequence of Positions 1 to 12486 of SEQ ID NO: 1.

(19a) A method for selecting a lipid-producing fungus having a high ability to form 16-carbon fatty acids, comprising assessing lipid-producing test fungi by the method of (19) above, and selecting a lipid-producing fungus having a high expression level of the fatty acid synthetase gene.

(19b) A method for producing an oil and fat, comprising the use of the lipid-producing fungus selected by the method of (19a) above.

(20) A method for selecting a lipid-producing fungus, comprising: culturing a lipid-producing reference fungus and a lipid-producing test fungus, measuring an expression level of a fatty acid synthetase gene having the nucleotide sequence Positions 1 to 12486 of SEQ ID NO: 1 in each lipid-producing fungus, and selecting a lipid-producing test fungus which expresses the gene more highly than the lipid-producing reference fungus.

(21) A method for selecting a lipid-producing fungus, comprising: culturing a lipid-producing reference fungus and a lipid-producing test fungus, quantitatively determining the protein of (8) above in each lipid-producing fungus, and selecting a lipid-producing test fungus containing a larger amount of protein than the lipid-producing reference fungus. That is, a method for selecting a lipid-producing fungus, comprising the steps of culturing a plurality of lipid-producing fungi, quantitatively determining the protein of (8) above in each lipid-producing fungus, and selecting from among these a lipid-producing test fungus containing a large amount of the protein.

The polynucleotides of the invention, when utilized to transform organisms such as lipid-producing fungi (e.g., *M. alpina*) and yeasts, are useful for application in the manufacture of foods, cosmetics, drugs (e.g., external skin preparations), soaps and the like.

Fatty acids can be efficiently produced by the method for producing lipids or fatty acids of the invention. Moreover, by employing the nucleotides of the invention in transformation of yeasts and other organisms, lipids or fatty acids having a high content of 16-carbon fatty acids (e.g., palmitic acid, palmitoleic acid) can be produced. The present invention is thus beneficial for increasing the ability to produce such fatty acids.

By using lipid-producing fungi which have been assessed and selected using the methods for assessing and selecting lipid-producing fungi of the invention, oils and lipids of the desired composition (e.g., oils and lipids having a high proportion of 16-carbon fatty acids) can be efficiently manufactured.

BRIEF DESCRIPTION OF THE DRAWINGS

FIG. 1 (1-1 to 1-5) shows the alignment of amino acid sequences for known FAS1 proteins (from *Saccharomyces cerevisiae* (SEQ ID NO: 17), *Candida albicans* (SEQ ID NO: 18, and *Aspergillus nidulans* (SEQ ID NO: 19)).

BEST MODE FOR CARRYING OUT THE INVENTION

As shown in detail in the subsequently described examples of the invention, the inventors have succeeded for the first time in cloning full-length cDNA for a fatty acid synthetase from the *M. alpina* strain 1S-4, which is a lipid-producing fungus. Moreover, they have obtained the base sequence of the genomic DNA for the fatty acid synthetase from *M. alpina* strain 1S-4 (SEQ ID NO: 2), and the putative amino acid sequence for that fatty acid synthetase (SEQ ID NO: 3). This DNA and enzyme can be obtained using, for example, the techniques mentioned in the subsequently described examples of the invention, known genetic engineering techniques, and known synthesis techniques. The fatty acid synthetase polynucleotides provided by the present invention, when employed to transform organisms such as lipid-producing fungi or yeasts, are useful for the production of oils and lipids with such transformed lipid-producing fungi (e.g., *M. alpina*) or yeast and for the manufacture of foods, drugs (e.g., external skin preparations), industrial materials (such as for cosmetics and soaps) and the like that utilize such oils and lipids.

1. Polynucleotides of the Invention

Accordingly, in one aspect, the invention provides the following polynucleotides:

(a) a polynucleotide comprising a polynucleotide consisting of the nucleotide sequence of Positions 1 to 12486 of SEQ ID NO: 1;

(b) a polynucleotide comprising a polynucleotide consisting of the nucleotide sequence of SEQ ID NO: 2 or a part thereof;

(c) a polynucleotide comprising a polynucleotide encoding a protein having the amino acid sequence of SEQ ID NO: 3;

(d) a polynucleotide comprising a polynucleotide encoding a protein which consists of an amino acid sequence of SEQ ID NO:3 in which one or more amino acids are deleted, substituted, inserted and/or added, and which has a fatty acid synthetase activity;

(e) a polynucleotide comprising a polynucleotide encoding a protein having 60% or higher identity with the amino acid sequence of SEQ ID NO: 3, and which has a fatty acid synthetase activity;

(f) a polynucleotide comprising a polynucleotide which hybridizes under stringent conditions to a polynucleotide consisting of a nucleotide sequence complementary to the nucleotide sequence of Positions 1 to 12486 of SEQ ID NO: 1, and which encodes a protein consisting of a fatty acid synthetase activity;

(g) a polynucleotide comprising a polynucleotide which hybridizes under stringent conditions to a polynucleotide consisting of a nucleotide sequence complementary to the nucleotide sequence of SEQ ID NO: 2 or a part thereof, and which encodes a protein having a fatty acid synthetase activity; and (h) a polynucleotide comprising a polynucleotide which hybridizes under stringent conditions to a polynucleotide consisting of a nucleotide sequence complementary to the nucleotide sequence of a polynucleotide encoding a protein consisting of the amino acid sequence of SEQ ID NO: 3, and which encodes a protein having a fatty acid synthetase activity.

As used herein, the term "polynucleotide" refers to DNA or RNA.

As used herein, "part of the DNA consisting of the nucleotide sequence of SEQ ID NO: 2" encompasses, for example, the portion of the nucleotide sequence of SEQ ID NO: 2 corresponding to the exon.

"A polynucleotide which hybridizes under stringent conditions" refers herein to a polynucleotide which is obtained by, for example, colony hybridization, plaque hybridization or Southern hybridization using as the probe all or part of a polynucleotide consisting of the nucleotide sequence complementary to the nucleotide sequence of Positions 1 to 12486 of SEQ ID NO: 1 and the nucleotide sequence of SEQ ID NO: 2, or a polynucleotide consisting of a nucleotide sequence coding for the amino acid sequence of SEQ ID NO: 3. The hybridization method used may be a method described in, for example, Sambrook & Russell, Molecular Cloning: A Laboratory Manual, Vol. 3 (Cold Spring Harbor, Laboratory Press 2001) or Ausubel: Current Protocols in Molecular Biology (John Wiley & Sons, 1987-1997).

As used herein, "stringent conditions" may refer to low stringency conditions, moderate stringency conditions and high stringency conditions. "Low stringency conditions" are, for example, 5×SSC, 5×Denhart's solution, 0.5% SDS and 50% formamide at 32° C. "Moderate stringency conditions" are, for example, 5×SSC, 5×Denhart's solution, 0.5% SDS and 50% formamide at 42° C. "High stringency conditions" are, for example, 5×SSC, 5× Denhart's solution, 0.5% SDS and 50% formamide at 50° C. Under these conditions, DNA of higher homology is expected to be obtained efficiently at higher temperature. Multiple factors are involved in hybridization stringency, including temperature, probe concentration, probe length, ionic strength, time and salt concentration, and one skilled in the art may appropriately select these factors to realize a similar stringency.

An example of a commercial kit that may be used for hybridization is AlkPhos Direct Labeling Reagents (Amersham Pharmacia Biotech). According to the protocol that comes with the kit, after incubation with a labeled probe overnight, the membrane is washed with a primary wash buffer containing 0.1% (w/v) SDS at 55° C., following which the hybridized DNA can be detected.

Other polynucleotides that can be hybridized include DNAs having about 60% or higher, about 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity to the DNA of SEQ ID NO: 1 (or the nucleotide sequence of Positions 1 to 12486 of SEQ ID NO: 1), the DNA of SEQ ID NO: 2, or the DNA coding for the amino acid sequence of SEQ ID NO: 3, as determined with homology search software, such as FASTA or BLAST, using the default parameters.

Identity between amino acid sequences or nucleotide sequences may be determined using the algorithm BLAST by Karlin and Altschul (Proc. Natl. Acad. Sci. USA, 872264-2268 (1990); Proc. Natl. Acad. Sci. USA, 90: 5873 (1993)). Programs called BLASTN and BLASTX based on the BLAST algorithm have been developed (Altschul S F, et al., J. Mol. Biol. 215: 403 (1990)). When a nucleotide sequence is analyzed using BLASTN, the parameters are set to, for example, score=100 and word length=12. When an amino acid sequence is analyzed using BLASTX, the parameters are set to, for example, score=50 and word length=3. When the BLAST and Gapped BLAST programs are used, the default parameters for the respective programs are employed.

The foregoing polynucleotides of the invention may be obtained by a known genetic engineering technique or a known synthesis technique.

2. Proteins of the Invention and Polynucleotides Which Encode the Proteins

In another aspect, the invention provides proteins encoded by one of the above polynucleotides (a) to (h).

In yet another aspect, the invention provides:
(a) a protein which comprises the amino acid sequence of SEQ ID NO: 3;
(b) a protein which comprises an amino acid sequence of SEQ ID NO: 3 in which one or more amino acids are deleted, substituted, inserted and/or added, and which has a fatty acid synthetase activity; or
(c) a protein having 60% or higher identity with the amino acid sequence of SEQ ID NO: 3, and which has a fatty acid synthetase activity.

In still another aspect, the invention provides a polynucleotide which comprises a nucleotide sequence coding for the above protein.

Above protein (b) or (c) is typically a variant of the naturally occurring protein of SEQ ID NO: 3, and may be obtained artificially by using a site-specific mutagenesis technique described in, for example, Sambrook & Russell, Molecular Cloning: A Laboratory Manual, Vol. 3 (Cold Spring Harbor Laboratory Press, 2001); Ausubel, Current Protocols in Molecular Biology (John Wiley & Sons, 1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985); or Proc. Natl. Acad. Sci. USA, 82, 488 (1985).

In the specification, the "protein which consists of an amino acid sequence of SEQ ID NO:3 in which one or more amino acids are deleted, substituted, inserted and/or added, and which has a fatty acid synthetase activity" is exemplified by proteins which consist of an amino acid sequence wherein from 1 to 500, from 1 to 100, from 1 to 90, from 1 to 80, 1 to 70, from 1 to 60, from 1 to 50, from 1 to 40, from 1 to 39, from 1 to 38, from 1 to 37, from 1 to 36, from 1 to 35, from 1 to 34, from 1 to 33, from 1 to 32, from 1 to 31, from 1 to 30, from 1 to 29, from 1 to 28, from 1 to 27, from 1 to 26, from 1 to 25, from 1 to 24, from 1 to 23, from 1 to 22, from 1 to 21, from 1 to 20, from 1 to 19, from 1 to 18, from 1 to 17, from 1 to 16, from 1 to 15, from 1 to 14, from 1 to 13, from 1 to 12, from 1 to 11, from 1 to 10, from 1 to 9, from 1 to 8, from 1 to 7, from 1 to 6 (from 1 to several), from 1 to 5, from 1 to 4, from 1 to 3, 1 or 2, or 1 amino acid residue in the amino acid sequence of SEQ ID NO:3 has been deleted, substituted, inserted and/ or added, and which have a fatty acid synthetase activity. A smaller number of the above deleted, substituted, inserted and/or added amino acid residues is generally more preferable. Such proteins are exemplified by proteins having an amino acid sequence with about 60% or higher, about 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity to the amino acid sequence of SEQ ID NO: 3, and having a fatty acid synthetase activity. A higher percent identity is generally more preferable. The fatty acid synthetase activity can be measured by, for example, the method described in James K Stoops et al., J.B.C. 253, 4464-4475 (1978).

The deletion, substitution, insertion and/or addition of one or more amino acid residue in the amino acid sequence of the protein of the invention means that one or more amino acid residue is deleted, substituted, inserted and/or added at any one or more position in the same sequence. Any two or more types of changes from among deletions, substitutions, insertions and additions may occur concurrently.

Examples of mutually substitutable amino acid residues are given below. Amino acid residues belonging to the same group are mutually substitutable.

Group A: leucine, isoleucine, norleucine, valine, norvaline, alanine, 2-aminobutanoic acid, methionine, o-methylserine, t-butylglycine, t-butylalanine, cyclohexylalanine;

Group B: aspartic acid, glutamic acid, isoaspartic acid, isoglutamic acid, 2-aminoadipic acid, 2-aminosuberic acid;

Group C: asparagine, glutamine;

Group D: lysine, arginine, ornithine, 2,4-diaminobutanoic acid, 2,3-diaminopropionic acid;

Group E: proline, 3-hydroxyproline, 4-hydroxyproline;

Group F: serine, threonine, homoserine; and

Group G: phenylalanine, tyrosine.

The protein of the invention may also be produced by a chemical synthesis process such as the Fmoc process (fluorenylmethyloxycarbonyl process) or the tBoc process (t-butyloxycarbonyl process). In addition, peptide synthesizers available from, for example, Advanced ChemTech, PerkinElmer, Pharmacia, Protein Technology Instrument, Synthecell-Vega, PerSeptive and Shimadzu Corporation may be used for chemical synthesis.

3. Vector of the Invention and Transformants in which the Vector Has Been Introduced In a further aspect, the invention provides an expression vector which comprises the polynucleotide of the invention. The expression vector of the invention comprises one of the following polynucleotides:

(a) a polynucleotide comprising a polynucleotide consisting of the nucleotide sequence of Positions 1 to 12486 of SEQ ID NO: 1;

(b) a polynucleotide comprising a polynucleotide consisting of the nucleotide sequence of SEQ ID NO: 2 or a part thereof;

(c) a polynucleotide comprising a polynucleotide encoding a protein having the amino acid sequence of SEQ ID NO: 3;

(d) a polynucleotide comprising a polynucleotide encoding a protein which consists of an amino acid sequence of SEQ ID NO: 3 in which one or more amino acids are deleted, substituted, inserted and/or added, and which has a fatty acid synthetase activity;

(e) a polynucleotide comprising a polynucleotide encoding a protein having 60% or higher identity with the amino acid sequence of SEQ ID NO: 3, and which has a fatty acid synthetase activity;

(f) a polynucleotide comprising a polynucleotide which hybridizes under stringent conditions to a polynucleotide consisting of a nucleotide sequence complementary to the nucleotide sequence of Positions 1 to 12486 of SEQ ID NO: 1, and which encodes a protein consisting of a fatty acid synthetase activity;

(g) a polynucleotide comprising a polynucleotide which hybridizes under stringent conditions to a polynucleotide consisting of a nucleotide sequence complementary to the nucleotide sequence of SEQ ID NO: 2 or a part thereof, and which encodes a protein having a fatty acid synthetase activity; or (h) a polynucleotide comprising a polynucleotide which hybridizes under stringent conditions to a polynucleotide consisting of a nucleotide sequence complementary to the nucleotide sequence of a polynucleotide encoding a protein consisting of the amino acid sequence of SEQ ID NO: 3, and which encodes a protein having a fatty acid synthetase activity.

The vector of the invention generally comprises an expression cassette comprising the followings as components: (i) a promoter which can transcribes in a host cell; (ii) the polynucleotide of any one of (a) to (h) above which is joined to the promoter; and (iii) a signal which functions within a host cell in connection with the transcription termination and polyadenylation of an RNA molecule. The vector constructed in this way is introduced in a host cell. Host cells suitable for use in the invention are exemplified by lipid-producing fungi and yeasts.

Fungal strains mentioned in, for example, Mycotaxon, Vol. XLIV, No. 2, pp. 257-265 (1992) may be used as the lipid-producing fungus. Illustrative examples include microorganisms belonging to the genus *Mortierella*, such as the following microorganisms belonging to the subgenus *Mortierella*: *Mortierella elongata* IFO8570, *Mortierella exigua* IFO8571, *Mortierella hygrophila* IFO5941, and *Mortierella alpina* IFO8568, ATCC16266, ATCC32221, ATCC42430, CBS219.35, CBS224.37, CBS250.53, CBS343.66, CBS527.72, CBS528.72, CBS529.72, CBS608.70 and CBS754.68; and the following microorganisms belonging to the subgenus *Micromucor*: *Mortierella isabellina* CBS194.28, IFO6336, IFO7824, IFO7873, IFO7874, IFO8286, IFO8308 and IFO7884, *Mortierella nana* WF08190, *Mortierella ramanniana* IFO5426, IFO8186, CBS112.08, CBS212.72, IFO7825, IFO8184, IFO8185 and IFO8287, and *Mortierella vinacea* CBS236.82. *Mortierella alpina* is especially preferred.

Illustrative examples of yeasts include *Saccharomyces cerevisiae* NBRC1951, NBRC1952, NBRC1953 and NBRC1954. These host cells that have been transformed with the vector of the invention are able to very efficiently produce in particular fatty acids having 16 carbon atoms.

The vector used for introduction into a lipid-producing fungi is exemplified by, but not limited to, pDura5 (Appl. Microbiol. Biotechnol., 65, 419-425, (2004)).

The vector used for introduction into a yeast may be a multicopy vector (YEp vector), a single-copy vector (YCp vector), or a chromosomal integration vector (YIp vector). An example of a known YEp vector is YEp24 (J. R. Broach et al., Experimental Manipulation of Gene Expression (Academic Press, New York; 1983), 83), an example of a YCp vector is YCp50 (M. D. Rose et al., Gene 60: 237 (1987)), and an example of a YIp vector is YIp5 (K. Struhl et al., Proc. Natl. Acad. Sci. USA, 76: 1035 (1979)). All of these are readily available.

Any combination of promoters and terminators may be used for regulating gene expression in the host cell, so long as they function in the host cell. For example, when a lipid-producing fungus is employed, use may be made of the histone H4.1 gene promoter or the glyceraldehyde 3-phosphate dehydrogenase gene promoter.

Examples of selective markers that may be used during transformation include auxotrophic markers (ura5, niaD), drug resistant markers (hygromycin, zeocin), geneticin-resistant genes (G418r), copper-resistant genes (CUP1) (Marin et al., Proc. Natl. Acad. Sci. USA, 81, 337 (1984)), and cerulenin-resistant genes (fas2m, PDR4) (respectively Junji Inokoshi et al., Biochemistry, 64, 660 (1992); and Hussain et al., Gene, 101: 149 (1991)).

A commonly known method may be used to transform the host cell. In the case of lipid-producing fungi, examples of suitable methods include electroporation (Mackenzie D. A., et al., Appl. Environ. Microbiol. 66, 4655-4661 (2000)) and the particle delivery method (the method described in Japanese Patent Application Laid-open No. 2005-287403, entitled "Method for Breeding Lipid-Producing Fungi"). In the case of yeasts, illustrative, non-limiting examples of suitable methods include electroporation, the spheroplast method (Proc. Natl. Acad. Sci. USA, 75: 1929 (1978)), the lithium acetate method (J. Bacteriology, 153: 163 (1983)), and the methods described in Proc. Natl. Acad. Sci. USA, 75: 1929 (1978) and in Methods in Yeast Genetics, 2000 Edition: A Cold Spring Harbor Laboratory Course Manual.

More specifically, in the case of lipid-product fungi, the host is inoculated on a Czapek-Dox medium and cultured for 2 weeks at 28° C. to form spores. The spores are then collected, and a gene is introduced therein by the particle delivery method (described in Japanese Patent Application Laid-open No. 2005-287403, entitled "Method for Breeding Lipid-Producing Fungi") or the like. Next, the spores comprising the introduced gene are placed on a standard agar medium containing an antibiotic or the like to be used as a selective marker or, when an auxotrophic marker is to be used, on an agar medium lacking the nutrient to be used as the marker so as to obtain a transformant. Alternatively, in the case of yeasts, the host is cultured in a standard nutrient medium (e.g., the YEPD medium described in Genetic Engineering, Vol. 1 (Plenum Press, New York; 1979), p. 117) such that the optical density of the medium at 600 nm (OD600) is between 1 and 6. The cultured cells are then collected by centrifugation, washed, and pre-treated with alkali metal ions, preferably lithium ions, at a concentration of about 1 to 2 M. The cells are left to stand at about 30° C. for about 60 minutes, then left to stand together with the DNA to be introduced (about 1 to 20 µg) at about 30° C. for about 60 minutes. Polyethylene glycol, preferably a polyethylene glycol having a molecular weight of about 4,000 daltons, is added to a final concentration of about 20% to 50%. The cells are left at rest at about 30° C. for about 30 minutes, then heat-treated at about 42° C. for about 5 minutes. Preferably, the resulting cell suspension is washed with a standard nutrient medium, added to a predetermined amount of fresh standard nutrient medium, and left to stand at about 30° C. for about 60 minutes. The resulting culture is inoculated on a standard agar medium containing an antibiotic or the like to be used as a selective marker or, when an auxotrophic marker is to be used, on an agar medium lacking the nutrient to be used as an auxotrophic marker so as to obtain a transformant. Other common cloning techniques may be found in, for example, Sambrook & Russell, Molecular Cloning: A Laboratory Manual, Vol. 3 (Cold Spring Harbor Laboratory Press, 2001) and Methods in Yeast Genetics: A Laboratory Manual (Cold Spring Harbor Laboratory Press; Cold Spring Harbor, N.Y.).

4. Method for Producing a Lipid or Fatty Acid of the Invention

In a still further aspect, the invention provides a method for producing a lipid or a fatty acid using the above-described transformed lipid-producing fungus or yeast.

As used herein, "lipid" refers to simple lipids containing, for example, a compound made up of a fatty acid and an alcohol with an ester linkage therebetween (e.g., a glyceride) or an analog thereof (e.g., a cholesterol ester), complex lipids additionally having, for example, a phosphoric acid, amino acid or sugar bonded to part of a simple lipid, and derivative lipids which are lipid hydrolyzates and do not dissolve in water.

"Oils and fats" refers herein to esters of glycerols and fatty acids (glycerides).

"Fatty acids" refers herein to aliphatic monocarboxylic acids (carboxylic acids having a single carboxyl group, in which the carbon atoms are linked together in the form of a chain) of the general formula RCOOH (R being an alkyl group). Fatty acids include saturated fatty acids having no double bonds on the hydrocarbon chain, and unsaturated fatty acids which contain a double bond.

The lipid or fatty acid of the invention may be extracted in the following manner from cells transformed according to the present invention. In the case of transformed organisms (e.g., lipid-producing fungi or yeasts), following the completion of culturing, the cultured cells are collected by a conventional technique such as centrifugation or filtration. The cells are thoroughly rinsed and preferably dried. Drying may be carried out by lyophilization, air drying or the like. The dried cells are disrupted, such as with a Dynomill or ultrasonically, then preferably subjected to extraction treatment with an organic solvent under a stream of nitrogen. Organic solvents that may be used include ether, hexane, methanol, ethanol, chloroform, dichloromethane and petroleum ether. Alternatively, good results may also be obtained by alternating extraction with methanol and petroleum ether, or by extraction using a chloroform-methanol-water single-layer system as the solvent. By driving off the organic solvent from the extract under a reduced pressure, a fatty acid-containing lipid can be obtained.

Separation of the fatty acid from the fatty acid-containing lipid above in the state of a mixed fatty acid or a mixed fatty acid ester may be carried out by concentration and separation according to a conventional technique (e.g., the urea addition method, the cooling separation method, column chromatography).

Using the method for producing a lipid or fatty acid of the invention, a fatty acid can be efficiently produced by increasing the fatty acid content of the cells. Alternatively, when a yeast is used as the host, a lipid or fatty acid having a high content of 16-carbon saturated or unsaturated fatty acid (e.g., palmitic acid or palmitoleic acid) can be obtained, which is particularly useful when there is a need to produce such a fatty acid in a large amount and/or at a high efficiency.

The lipid or fatty acid thus obtained may be used in accordance with a conventional method in such applications as the manufacture of lipid-containing foods, drugs (e.g., external skin preparations), and industrial materials (starting materials for cosmetics, soaps and the like).

To illustrate, because palmitoleic acid is a fatty acid which is present in a concentration of at least about 10% in human sebum and reputedly plays a major role in regeneration of sebum, it may utilized by being included in skin cosmetics for preventing aging of the skin or in external skin preparations. For example, in a patient having a skin disorder such as eczema, regardless of the patient's age, regeneration of the skin tissue can be promoted by supplementing the palmitoleic acid. Therefore, the lipid or fatty acid obtained by the method for producing a lipid or fatty acid of the invention may be advantageously used in the production of cosmetics and drugs (e.g., external skin preparations) produced for such purposes as to prevent aging of the skin or to regenerate skin tissue.

Accordingly, in yet another aspect, the invention provides a method for producing a food, cosmetic, drug, soap or the like using the transformed lipid-producing fungus or the transformed yeast of the invention. This method includes the step of forming a lipid or fatty acid using the transformed lipid-producing fungus or the transformed yeast of the invention. The food, cosmetic, drug, soap or the like containing the lipid or fatty acid that has been formed is prepared by a conventional method. In this way, the food, cosmetic, drug, soap or the like manufactured by the method of the invention contains a lipid or fatty acid formed using the transformed lipid-forming fungus or the transformed yeast of the invention. In addition, the invention also provides the food, cosmetic, drug, soap or the like manufactured by such a method.

The form of the cosmetic (composition) or drug (composition) of the invention is not subject to any particular limitation. Any suitable form, such as that of a solution, paste, gel, solid or powder, may be employed. Cosmetic compositions or drug compositions according to the invention may be used in, for example, cosmetics or external skin preparations such as oils, lotions, creams, emulsions, gels, shampoos, hair rinses, hair conditioners, nail polishes, foundations, lipsticks, face powders, facial masks, ointments, perfumes, powders, colognes, toothpastes, soaps, aerosols and cleansing foams; and in skin aging inhibiting and improving agents, dermatitis inhibiting and improving agents, bath agents, hair growth medications, skin serums, sunscreens, and inhibiting and improving agents for cuts, chapped skin, and rough, dry skin.

Cosmetic compositions according to the invention may optionally include also other oils and fats and/or dyes, fragrances, preservatives, surfactants, pigments and antioxidants, etc. The proportion in which such ingredients are included may be appropriately decided by one skilled in the art according to the intended purpose (for example, oils and fats may be included in the composition in a proportion of from 1 to 99.99 wt %, preferably from 5 to 99.99 wt %, and more preferably from 10 to 99.95 wt %). Drug compositions according to the invention (e.g., external skin preparations) may optically include other pharmaceutically active ingredients (e.g., anti-inflammatory ingredients) or adjuvant ingredients (e.g., lubricating ingredients, carrier ingredients). For instance, illustrative examples of other common ingredients in cosmetics or external skin preparations include acne medications, anti-dandruff and pruritus agents, antiperspirants, burn medications, anti-tick and lice agents, keratin softeners, xeroderma medications, antiviral agents and percutaneous absorption enhancers.

Examples of foods according to the invention include dietary supplements, health foods, functional foods, children's foods, infant modified milk, premature infant modified milk, and geriatric foods. In this specification, "foods" refers generically to ingestible products that are solids, fluids, liquids, or mixtures thereof.

"Dietary supplements" refers to foods fortified with specific nutritional ingredients. "Health foods" refers to foods regarded as healthful or good for the health, and include dietary supplements, natural foods and diet foods. "Functional foods" refers to foods for replenishing nutritional ingredients that have body regulating functions, and is synonymous with foods for specified health uses. "Children's foods" refers to foods given to children up to about 6 years of age. "Geriatric foods" refers to foods that have been treated so as to be easier to digest and absorb than untreated foods. "Infant modified milk" refers to milk formulas given to children up to about 1 year of age. "Premature infant modified milk" refers to milk formulas given to premature infants up to about 6 months after birth.

Examples of the forms of these foods include naturally occurring foods such as meat, fish and nuts (foods treated with oils and fats); foods to which oils and fats are added at the time of preparation, such as Chinese food, ramen noodles and soups; foods prepared using oils and fats as a heat transfer medium, such as tempura, deep-fried foods, fried tofu, fried rice, donuts and the sweet fried Japanese snack known as karinto; oil and fat-based foods or processed foods obtained by the addition of oils and fats during processing, such as butter, margarine, mayonnaise, salad dressing, chocolate, instant ramen, caramel, biscuits, cookies, cakes and ice cream; and foods that have been finished by spraying or coating with an oil and fat, such as okaki rice crackers, hard biscuits and the bean paste-filled buns known as anpan. However, the foods of the invention are not limited to foods containing oils and fats, and include also, for example, breads, noodles, rice, sweets (hard candies, chewing gum, gummy candies, pressed dry candies, Japanese sweets), agricultural foods such as tofu and processed foods made from tofu; fermented foods such as sake, medicinal liquor, rice cooking wine (mirin), vinegar, soy sauce and miso; foods obtained from livestock, such as yogurt, ham, bacon and sausage; seafood products such as molded fish paste (kamaboko), fish-based fried foods known as ageten and hanpen fish cakes; and also fruit drinks, soft drinks, sports drinks, alcoholic beverages and tea.

The foods of the invention may alternatively be in the form of drug preparations such as capsules; or in processed forms such as free-flowing foods, semi-digested diets, elemental diets, energy drinks and enteral foods obtained by formulating the oil and fat of the invention together with ingredients such as proteins, sugars, fats, trace elements, vitamins, emulsifiers and flavoring agents.

5. Methods for Assessing the Fatty Acid-Forming Ability of Lipid-Producing Test Fungi and for Selecting Lipid-Producing Fungi of the Invention In additional aspects, the invention provides (i) a method for assessing the fatty acid-forming ability of a lipid-producing test fungus, comprising the use of a primer or probe designed based on the nucleotide sequence of a fatty acid synthetase gene having the nucleotide sequence of Positions 1 to 12486 of SEQ ID NO: 1; (ii) a method for assessing the fatty acid-forming ability of a lipid-producing test fungus, comprising the steps of culturing a lipid-producing test fungus and measuring the expression level of a fatty acid synthetase gene having the nucleotide sequence of Positions 1 to 12486 of SEQ ID NO: 1; and (iii) a method for selecting a lipid-producing fungus, comprising the steps of culturing a lipid-producing reference fungus and a lipid-producing test fungus, measuring the expression level of a fatty acid synthetase gene having the nucleotide sequence of Positions 1 to 12486 of SEQ ID NO: 1 in each lipid-producing fungus, and selecting a lipid-producing test fungus which expresses the gene more highly than the lipid-producing reference fungus. The nucleotide sequence of SEQ ID NO: 2 may be used instead of the nucleotide sequence of Positions 1 to 12486 of SEQ ID NO: 1.

General techniques for carrying out such a method of assessment are known to the art and include those described in, for example, WO 01/040514 and Japanese Patent Application Laid-open No. H8-205900. The method of assessment is briefly described below.

First, the genome of the lipid-producing test fungus is prepared. Preparation may be carried out by any known method, such as one involving the use of a commercially kit; e.g., a DNeasy Plant Kit (QIAGEN). A primer or probe designed based on the fatty acid synthetase gene nucleotide sequence of Positions 1 to 12486 of SEQ ID NO: 1 or of SEQ ID NO: 2 (preferably the nucleotide sequence of Positions 1 to 12486 of SEQ ID NO: 1) is then used to determine whether this gene itself or a specific nucleotide sequence on the gene is present in the lipid-producing test fungus genome that has been prepared. A known technique may be used to design the primer or probe.

A known technique may be used for detecting the gene or a specific nucleotide sequence thereon. For example, using as one primer a polynucleotide comprising part or all of a specific nucleotide sequence or a polynucleotide comprising a nucleotide sequence complementary to the specific nucleotide sequence, and using as another primer a polynucleotide comprising part or all of a nucleotide sequence upstream or downstream from the specific nucleotide sequence or a polynucleotide comprising a nucleotide sequence complementary to the upstream or downstream nucleotide sequence, the nucleic acid of the lipid-producing fungus is amplified by the polymerase chain reaction (PCR) method, the presence or absence of amplification products is determined, and the molecular weights of any such products are measured. The number of nucleotides in the polynucleotides used as the primers is generally at least 10 bp, and preferably from 15 to 25 bp. It is generally appropriate for the number of nucleotides in the portion of the polynucleotide between the primers to be from 300 to 2,000 bp.

The reaction conditions for the PCR method are not subject to any particular limitation. For example, conditions within the following ranges may be used: denaturing temperature, 90 to 98° C.; annealing temperature, 40 to 60° C.; extension temperature, 60 to 75° C.; number of cycles, 10 or more. The reaction product obtained as a result may be separated off by a technique such as agarose gel electrophoresis, and the molecular weights of the amplification products may be measured. Using this method, the ability of the lipid-producing fungus to form fatty acids is predicted and assessed based on whether the molecule weights of the amplification products are large enough to contain the DNA molecule for specific portions. The above ability can be even more accurately predicted and assessed by analyzing the nucleotide sequences of the amplification products.

Moreover, in the practice of the invention, by culturing the lipid-producing test fungus and measuring the expression level of the fatty acid synthetase gene having the nucleotide sequence of Positions 1 to 12486 of SEQ ID NO: 1, it is also possible to assess the fatty acid-forming ability of the lipid-producing test fungus. This may be done by culturing the lipid-producing test fungus, and quantitatively determining the mRNA or protein product of the fatty acid synthetase gene having the nucleotide sequence of Positions 1 to 12486 of SEQ ID NO: 1. Quantitative determination of the mRNA or protein may be carried out using a known technique. For example, the mRNA may be determined quantitatively by northern hybridization or quantitative RT-PCR, and the protein may be determined quantitatively by western blotting (Current Protocols in Molecular Biology, John Wiley & Sons, 1994-2003).

In addition, a suitable lipid-producing fungus may be selected by culturing lipid-producing test fungi, measuring the expression level of a fatty acid synthetase gene having the nucleotide sequence of Positions 1 to 12486 of SEQ ID NO: 1, and selecting a lipid-producing test fungus having an expression level of the fatty acid synthetase gene which is in accordance with the desired fatty acid-forming ability. Alternatively, it is possible to culture a fatty acid-producing reference fungus and fatty acid test fungi, measure the expression level of the gene in each of the lipid-producing fungi, compare the expression levels of the gene in the lipid-producing reference fungus and the lipid-producing test fungi, and select the desired lipid-producing test fungus. Specifically, suitable lipid-producing fungi can be selected by culturing a lipid-producing reference fungus and lipid-producing test fungi, measuring the expression amounts of the fatty acid synthetase gene having the nucleotide sequence of Positions 1 to 12486 of SEQ ID NO: 1 in each lipid-producing fungus, and selecting a lipid-producing test fungus within the expression of this gene is higher than in the lipid-producing reference fungus.

Alternatively, a desired lipid-producing test fungus may be selected by culturing lipid-producing test fungi, and selecting a lipid-producing fungus which has a high or low fatty acid-forming ability or in which the fatty acid synthetase gene containing the nucleotide sequence of Positions 1 to 12486 of SEQ ID NO: 1 shows a high or low fatty acid synthetase activity. In such cases, lipid-producing fungi in which the above-described vector of the invention has been introduced, lipid-producing fungi in which expression of the above-described polynucleotide (DNA) of the invention is suppressed, lipid-producing fungi which have been subjected to mutagenic treatment, and lipid-producing fungi which have spontaneously mutated may be used as the lipid-producing test fungi or the lipid-producing reference fungus. The fatty acid-forming ability may be measured using a method for quantitatively determining the level of fatty acids within the fungus cells, and the fatty acid synthetase activity may be measured using the method described in James K. Stoops et al.: J.B.C. 253, 4464-4475 (1978).

Because it is thus possible by the invention to assess the fatty acid-forming ability of lipid-producing fungi (e.g., *M. alpina*), and to select a desired lipid-producing fungus (e.g., a lipid-producing fungus having a high fatty acid-forming ability or a lipid-producing fungus having a high fatty acid content per cell), fats and oils of a desired composition can be efficiently manufactured.

Moreover, the expression level of the fatty acid synthetase gene may be used as an indicator for such purposes as to investigate the culturing conditions for efficiently carrying out fatty acid production, and to control the culturing process.

EXAMPLES

Examples are given below to more fully illustrate the present invention, but are not intended to limit the scope of the invention.

EST Analysis

*M. alpina* strain 1S-4 was inoculated in 100 mL of medium (1.8% glucose, 1% yeast extract, pH 6.0) and precultured for 3 days at 28° C. Next, 5 liters of medium (1.8% glucose, 1% soy powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) was placed in a 10-liter bioreactor (Able Co., Tokyo), following which the entire amount of the above preculture was inoculated therein and aeration cultured under stirring for 8 days at 300 rpm, 1 vvm and 26° C. Glucose in amounts corresponding to 2%, 2% and 1.5% were added to the cultures on days 1, 2 and 3 of culturing, respectively. Cells were collected at different stages on days 1, 2, 3, 6 and 8 of culturing, and the total RNA was prepared by the guanidine hydrochloride/CsCl method. An Oligotex-dT30 Super mRNA Purification Kit (Takara Bio) was used to carry out poly(A)+RNA purification from the total RNA. A cDNA library for each stage was constructed using the ZAP-cDNA Gigapack III Gold Cloning Kit (Stratagene), and one-pass sequence analysis (8,000 clones×5 stages) from the 5' end of the cDNA was carried out.

FAS Homolog Search

The nucleotide sequence thus obtained was searched for known fatty acid synthetase gene homologs by BLAST. As a result, two nucleotide sequences having extremely high homology with portions of the α subunit of a fatty acid synthetase from *Schizosaccharomyces pombe* (GB Accession No. BAB62032; the gene was FAS2) were found. These sequences had sections in common, and were thought to originate from a single gene. The sequence obtained as a result of assembly matched nucleotides 12262 to 12920 on SEQ ID NO: 1 (cDNA). However, homologs of the FAS1 gene could not be found.

Obtaining a Partial Sequence of a FAS1 Homolog

Because a FAS1 homolog was not found by the above analysis, the alignment of known FAS1 protein amino acid sequences (GB No. P07149 from *Saccharomyces cerevisiae*; GB No. P34731 from *Candida albicans*; GB No. AAB41494 from *Aspergillus nidulans*) was carried out (FIG. 1). Based on sequences (1) and (2) of the conserved domain:

```
Sequence (1):    QGSQEQGMGM      (SEQ ID NO: 4)

Sequence (2):    ATQFRQPALT,     (SEQ ID NO: 5)
``` the following degenerate primers were designed:

```
                                           (SEQ ID NO: 6)
    F1h-f:    CARGGNWSNCARGARCARGGNATGGGNATG (SEQ ID NO: 7)
    F1h-r:    GTNARNGCNGGYTGNGTRAAYTGNGTNGC.
```

The cDNA of *M. alpina* 1S-4 was synthesized from the total RNA obtained by the above-described EST analysis using random hexamer primers with the SuperScript Fast Strand System for RT-PCR (Invitrogen). Using the cDNA of *M. alpina* 1S-4 as the template, 30 PCR reaction cycles—each cycle consisting of 1 minute at 94° C., 1 minute at 50° C. and 1 minute at 72° C.—were carried out with ExTaq (Takara Bio), thereby giving approximately 300 bp DNA fragments. The DNA fragments obtained were TA cloned with a TA Cloning Kit (Invitrogen), and the plasmid thus obtained was named pCR-MaFAS1-1. The nucleotide sequence was then determined. BLAST analysis showed there to be a high degree of homology with part of the β subunit of fatty acid synthetase.

Screening from cDNA Library

FAS1 homologs and FAS2 homologs were screened as follows from the cDNA library. A DIG Labeling System (Roche) was used for screening. With the plasmid pCR-MaFAS1-1 as the template, a DIG-labeled probe for FAS1 homologs was created using the primer F1-1f: 5'-GCTCTG-TATGACTCTTCCCCC-3' (SEQ ID NO: 8) and the primer F1-1r: 5'-GCCAAAAGACCGTTGGGTGAC-3' (SEQ ID NO: 9).

A probe for FAS2 homologs was created with the cDNA of the *M. alpina* strain 1S-4 as the template and using the primers F2-1f: 5'-GGTGCAGGAGCGGGACTGAGTG-3' (SEQ ID NO: 10) and F2-1r: 5'-CGCATTTGCAACCGCAAC-CGCG-3' (SEQ ID NO: 11) by carrying out 30 reaction cycles—each cycle consisting of 1 minute at 94° C., 1 minute at 55° C. and 1 minute at 72° C.—with ExTaq (Takara Bio).

The approximately 170 bp DNA fragment obtained was TA cloned with a TOPO-TA Cloning Kit (Invitrogen), and the resulting plasmid was named pCR-MaFAS2-1. A DIG-labeled probe was created by PCR with the plasmid pCR-MaFAS2-1 as the template and using the primers F2-1f and F2-1r.

Screening from the cDNA library was carried out using these probes. Positive clones could not be obtained with the probe for FAS1 homologs.

However, when the probe for FAS2 homologs was used, it was possible to obtain several positive clones. The longest clone included a sequence which corresponded to nucleotides 7861 to 12,920 (5,060 bp) of SEQ ID NO: 1 (cDNA). This clone was named as the plasmid pBSMAFAS2-1. However, when compared with the known FAS2 gene, it did not appear to include the full length.

Construction of Genomic Library

The *M. alpina* strain 1S-4 was inoculated into 100 ml of a liquid medium (1% glucose, 0.5% yeast extract, pH 6.0), and shake cultured at 28° C. for 4 days. The cells were collected by filtration with a filter, and the genomic DNA was extracted by the CTAB method.

The genomic DNA thus obtained (approximately 200 µg) was partially digested with the restriction enzyme Sau3AI so that the distribution of the cleaved DNA was centered at close to 20 kb. The resulting DNA fragments were subjected to 10% to 40% sucrose density gradient centrifugation (rotor, SW28 (Beckman), 25,000 rpm, 10° C., 24 hours), and fractionated using an Automatic Liquid Charger (Advantec) and a Micro Tube Pump (Eyela) into 1 ml fractions. The fractions having distributions centered near 20 kbp were purified. With the DNA fragments thus obtained, a genomic library was prepared using the λBlueSTAR/BamHI Vector Kit (Novagen).

Screening from Genomic Library

The FAS1 homologs and FAS2 homologs were screened from the genomic library in the same way as in the above example (screening from cDNA library). As a result, clones that were positive both with the probe for FAS1 homologs and the probe for FAS2 homologs were obtained. Part of the nucleotide sequence of the insert for this clone (15,539 bp of SEQ ID NO: 2 (genome)) was sequenced.

From a comparison with the amino acid sequences of known FAS1 proteins and FAS2 proteins, it was inferred that nucleotides 1062 to 1064 (ATG) on SEQ ID NO: 2 (genome) function as an initiation codon. It was also inferred that the FAS1 homologs and the FAS2 homologs are encoded by a single polypeptide.

Cloning the Full-Length cDNA

First, with the cDNA of *M. alpina* 1S-4 as the template and using the primer F1-2f: ATGACTACCGCACAGTCCAACTTGACC (SEQ ID NO: 12) and the primer F1-1r, 30 PCR reaction cycles—each cycle consisting of 10 seconds at 98° C. and 15 minutes at 68° C.—were carried out with LATaq (Takara Bio). The approximately 5.4 kb DNA fragment obtained as a result was cloned with a TOPO-TA Cloning Kit (Invitrogen), giving a plasmid that was named pCR-MAFAS-1. The nucleotide sequence of the insert was checked, and found to correspond to nucleotides 1 to 5435 of SEQ ID NO: 1 (cDNA). The DNA was digested with the restriction enzyme EcoRI, and the 5.4 kb DNA fragment obtained was ligated to the EcoRI site of the vector pBluescriptII SK+. Product in which nucleotide No. 1 on SEQ ID NO: 1 (cDNA) is located on the SacI side of a multicloning site in the vector pBluescriptII SK+ was selected. The resulting plasmid was named pBS-MAFAS-1.

Next, an approximately 2 kb DNA fragment obtained by digesting the plasmid pBS-MAFAS2-1 with the restriction enzymes ApaI and EcoRV was linked to the ApaI and EcoRV sites of the vector pBluescript II SK+. The resulting plasmid was named pBS-FAS-2. Next, with the cDNA of *M. alpina* 1S-4 as the template and using the primer F1-3f: TGTCTTGAAGAGCAAGGAGTGG (SEQ ID NO: 13) and the primer F2-2r: GCGTAGTAGTCGCCGTGCTCAGCCATC (SEQ ID NO: 14), ten reaction cycles—each cycle consisting of 2 minutes at 92° C. followed by 10 seconds at 92° C., 30 seconds at 55° C. and 8 minutes at 68° C., then twenty reaction cycles—each cycle consisting of 10 seconds at 92° C., 30 seconds at 55° C. and 8 minutes plus 10 seconds at 68° C.—were carried out with Pfu Turbo DNA Polymerase (Stratagene). The approximately 3.6 kb DNA fragment obtained as a result was cloned to the vector pCR4Blunt-TOPO using the Zero Blunt TOPO PCR Cloning Kit (Invitrogen), and the resulting plasmid was named pCR-MAFAS-5. The approximately 3.1 kb DNA fragment obtained by digesting the plasmid pCR-MAFAS-5 with the restriction enzymes EcoRV and SpeI was ligated with the 4.9 kb DNA fragment obtained by digesting the plasmid pBS-MAFAS-2 with the restriction enzymes EcoRV and SpeI. The resulting plasmid was named pBS-MAFAS-3.

In addition, a 2.6 kb DNA fragment obtained by digesting pBS-MAFAS2-1 with the restriction enzyme EcoRV was ligated with a DNA fragment obtained by digesting the plasmid pBS-MAFAS-3 with the restriction enzyme EcoRV. The inserted DNA fragment was confirmed to be oriented in the proper direction, thus giving the plasmid pBS-MaFAS.

The plasmid pBS-MaFAS comprises DNA having the nucleotide sequence of SEQ ID NO: 1, and was thought to include the full length of the FAS homolog cDNA from *M. alpina* 1S-4. CDS was the sequence of nucleotides 1 to 12489, and ORF was the sequence of nucleotides 1 to 12486, of SEQ ID NO: 1. The putative amino acid sequence is shown in SEQ ID NO: 3 (protein).

This amino acid sequence, when compared with known fatty acid synthetase genes, had the structure of fatty acid synthetases from known fungi in which the β and α subunits are connected head-to-tail. However, the homology with type I fatty acid synthetases of bacterial origin known to have a similar structure was low. When the amino acid sequence of this protein was compared with the amino acid sequences of fatty acid synthetases of fungal origin in which the β subunit and α subunit are connected, the identity was about 50%. There were two repetitions of a motif composed of 165 amino acids corresponding to part of the conserved sequence (COG4982) of 3-oxoacyl-[acyl-carrier protein].

Moreover, when compared with the genomic sequence obtained earlier, this gene had 7 introns. In SEQ ID NO: 2, there were 8 exons: bases 1062 to 1304, bases 2140 to 2679, bases 2778 to 4724, bases 4823 to 7027, bases 7115 to 7243, bases 7339 to 7497, bases 7582 to 10668 and bases 10772 to 14947; and 7 introns: bases 1305 to 2139, bases 2680 to 2777, bases 4725 to 4822, bases 7028 to 7114, bases 7244 to 7338, bases 7498 to 7581, and bases 10669 to 10771.

Construction of Expression Vector for the Yeast *Saccharomyces cerevisiae*

The plasmid pBS-MaFAS was digested with the restriction enzyme ApaI, and then the ends were blunted with a DNA Blunting Kit (Takara Bio). This was followed by digestion with the restriction enzyme EcoRI, giving an approximately 13 kb DNA fragment. This DNA fragment was digested with the restriction enzyme BamHI, then blunted and subsequently ligated with the vector pYE22m (Biosci. Biotech. Biochem., 59, 1221-1228, 1995) digested with the restriction enzyme EcoRI, thereby constructing the plasmid pYE-MaFAS.

Fatty Acid Analysis of MaFAS High-Expression Yeast

Two randomly selected strains from among the transformants obtained by transforming the yeast strain *S. cerevisiae* EH1315 (Appl. Microbiol. Biotechnol., 30, 515-520, 1989) with the plasmid pYE-MaFAS were called the MaFAS-1 strain and the MaFAS-2 strain. In addition, one strain randomly selected from among the transformants obtained by transforming the yeast strain *S. cerevisiae* EH1315 with the vector pYE22m was used as the control (C-1 strain). One platinum loop of each of these strains was inoculated onto 10 ml of an SC-Trp liquid medium or 10 ml of a YPD liquid medium, and cultured at 30° C. for 2 days. The cells were then collected by centrifugal separation and lyophilized. The fatty acids in the cells were converted to their methyl esters by the hydrochloric acid/methanol method, and extracted with hexane. The hexane was then driven off, and gas chromatographic analysis was carried out. The results are shown in Table 1.

TABLE 1

Fatty Acid Composition of Yeast Cells Grown in Different Media

| Fatty acid composition (%) | Medium | | | | | |
|---|---|---|---|---|---|---|
|  | SC-Trp | | | YPD | | |
|  | Strain | | | | | |
|  | C-1 | FAS-1 | FAS-2 | C-1 | FAS-1 | FAS-2 |
| 14:0 | nd | 1.2 | 1.2 | nd | nd | 1.4 |
| 14:1 | nd | 1.0 | 1.1 | nd | nd | nd |
| 16:0 | 4.7 | 10.9 | 10.6 | 5.4 | 13.7 | 13.0 |
| 16:1 | 38.3 | 52.2 | 53.0 | 34.0 | 59.8 | 57.0 |
| 18:0 | 3.7 | 2.6 | 2.5 | 5.6 | nd | 2.9 |
| 18:1 | 51.3 | 28.5 | 27.9 | 52.3 | 26.5 | 24.1 |

In the C-1 strain, the proportion of the 18-carbon fatty acids stearic acid and oleic acid was higher than that of the 16-carbon fatty acids, whereas in the MaFAS-1 strain and the MaFAS-2 strain which had a high expression of MaFAS, the proportion of the 16-carbon fatty acids palmitic acid and palmitoleic acid was higher.

Construction of Expression Vector in the Lipid-Producing Fungus *Mortierella alpina*

The plasmid pBlueHpt (JP Laid-Open Publication No. 2005-287403) was digested with NcoI and BamHI, and then MCS1-F and MCS1-R in which 5'-terminus was phosphorylated were annealed and inserted, to give plasmid pBlueHpt-MCS.

(SEQ ID NO: 15)
MCS1-F: 5'-catggatcctctagactgcaggcatgcaagcttctcga (SEQ ID NO: 16)
MCS1-R: 5'-ctaggagatctgacgtccgtacgttcgaagagctctag The plasmid pDura5 (Appl. Microbiol. Biotechnol., 65, 419-425, (2004)) was digested with the restriction enzyme BamHI, and then the ends were blunted, followed by self-ligation. Then, the plasmid obtained was digested with the restriction enzyme XbaI, and then the ends were blunted, followed by self-ligation. Further, the plasmid obtained was digested with the restriction enzyme HindIII, and then the ends were blunted, followed by self-ligation. After the plasmid obtained was digested with EcoRI, a fragment having about 1.7 kbp obtained by digestion of the plasmid pBlueHptMCS with EcoRI was inserted. A plasmid having the histonH4.1 gene promoter inserted in the same direction was selected, and designated as plasmid vector pDura5MCS.

The plasmid pBS-MaFAS was digested with the restriction enzyme ApaI, and then the ends were blunted using the DNA Blunting Kit (Takara Bio). The product was then digested with the restriction enzyme XbaI, giving an approximately 13 kb DNA fragment. This DNA fragment was digested with the restriction enzyme HindIII, then blunted, following which it was ligated to the vector pDura5MCS digested with the restriction enzyme XbaI, thereby constructing the plasmid pDura5-MaFAS.

Transformation of the Lipid-Producing Fungus *M. alpina*

Using the plasmid pDura5-MaFAS, transformation by the particle delivery method was carried out, with use of the uracil-requiring strain Δura-3, as the host, derived from *M. alpina* in accordance with the method of the patent document (Method for Breeding Lipid-Producing Fungi). An SC agar medium (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, 2% agar) was used for selection of the transformants.

Two of the transformants obtained were named FAS-3 strain and FAS-4 strain. One randomly selected strain in which pDura5 had been introduced was named C-2 strain. These strains were inoculated into a liquid medium containing 2% glucose and 1% yeast extract, and shake cultured at 28° C. On day 3 of culturing, a 20% glucose solution was added in an amount corresponding to $1/20^{th}$ of the liquid culture. On day 4, some of the cells were collected and lyophilized. The fatty acids from the cells were converted to the corresponding methyl esters, then extracted with hexane. The hexane was driven off and gas chromatographic analysis was carried out, thereby quantitatively determining the amount of fatty acids per cell. The results are shown in Table 2.

TABLE 2

Fatty Acid Content (%) Per Cell

| Strain | | |
|---|---|---|
| FAS-3 | FAS-4 | C-2 |
| 30.6 | 30.1 | 28.1 |

Compared with the C-2 strain, the amount of fatty acid per cell increased in the FAS-3 and FAS-4 strains.

INDUSTRIAL APPLICABILITY

The present invention is useful for improving fatty acid productivity, for the production of desired fatty acids, and/or for the production of any of the following which contain desired fatty acids: foods, cosmetics, external skin preparations and/or soaps.

The invention claimed is:

1. An isolated polynucleotide selected from any one of the following (a) to (g):
    (a) a polynucleotide comprising the nucleotide sequence of positions 1 to 12486 of SEQ ID NO: 1;
    (b) a polynucleotide comprising the nucleotide sequence of SEQ ID NO: 2;
    (c) a polynucleotide comprising a polynucleotide encoding a protein having the amino acid sequence of SEQ ID NO: 3;
    (d) a polynucleotide comprising a polynucleotide encoding a protein which consists of an amino acid sequence of SEQ ID NO:3 in which one to 100 amino acids are deleted, substituted, inserted and/or added, and which is capable of synthesizing a 16-carbon fatty acid in a cell;
    (e) a polynucleotide comprising a polynucleotide encoding a protein having 95% or higher identity with the amino acid sequence of SEQ ID NO: 3, and which is capable of synthesizing a 16-carbon fatty acid in a cell;
    (f) a polynucleotide comprising a polynucleotide which hybridizes under stringency conditions of 5×SSC, 5×Denhart's solution, 0.5% SDS and 50% formamide at 50° C. to a polynucleotide consisting of a nucleotide sequence complementary to the nucleotide sequence of positions 1 to 12486 of SEQ ID NO: 1, and which encodes a protein capable of synthesizing a 16-carbon fatty acid in a cell; and
    (g) a polynucleotide comprising a polynucleotide which hybridizes under stringency conditions of 5×SSC, 5×Denhart's solution, 0.5% SDS and 50% formamide at 50° C. to a polynucleotide consisting of a nucleotide sequence complementary to the nucleotide sequence of SEQ ID NO: 2 or a part thereof, and which encodes a protein capable of synthesizing a 16-carbon fatty acid in a cell.

2. The polynucleotide according to claim 1, comprising the nucleotide sequence of positions 1 to 12486 of SEQ ID NO: 1.

3. The polynucleotide according to claim 1, comprising the nucleotide sequence of SEQ ID NO: 1.

4. The polynucleotide according to claim 1, comprising the nucleotide sequence of SEQ ID NO: 2.

5. The polynucleotide according to claim 1, comprising a polynucleotide which encodes a protein consisting of the amino acid sequence of SEQ ID NO: 3.

6. The polynucleotide according to claim 1, which is DNA.

7. A vector comprising the polynucleotide according to claim 1.

8. A transformed microorganism having introduced therein the polynucleotide according to claim 1.

9. A transformed microorganism having introduced therein the vector according to claim 7.

10. A transformed microorganism comprising the vector according to claim 7, wherein said microorganism has a higher 16-carbon fatty acid content than such a microorganism prior to transformation.

11. The transformed microorganism according to claim 8, wherein the microorganism is a fatty acid-producing fungus.

12. The transformed microorganism according to claim 11, wherein the fatty acid-producing fungus is *Mortierella alpina*.

13. A method for producing a lipid or fatty acid with a transformed microorganism, comprising:
   culturing the transformed microorganism according to claim 8 to produce a 16-carbon fatty acid; and
   extracting the 16-carbon fatty acid from the culture.

14. A method for producing a food or drug, comprising:
   (a) culturing the transformed microorganism according to claim 8 to produce a 16-carbon fatty acid;
   (b) extracting the 16-carbon fatty acid from the culture; and
   (c) adding the product of (b) to a food or drug composition.

* * * * *

SEQUENCE LISTING

<160> NUMBER OF SEQ ID NOS: 19

<210> SEQ ID NO 1
<211> LENGTH: 12926
<212> TYPE: DNA
<213> ORGANISM: Mortierella alpina

<400> SEQUENCE: 1

```
atgactaccg cacagtccaa cttgacccgt cctttggccc tcaagcaagg aacttctgag      60
gtctcgatcc tcgttccttc ggatgtctgg gtagcggctg aacaacttcg tgaggagttt     120
ctgatctcgg tcgaggctgc tcctgcagag gaggccgcag cgaccggaag tgctgacgat     180
caggcccccgg agatggcttt ggtggcccgt tttctcaaat ttgctacgga caagagcgag     240
cagagcgatc cttcactgca gttcattcct gtgctgagaa ccgtcttcct gttctttgtc     300
accaaatacc ttaaaggaaa cgacatccac gcggtcactc gacttttagc aaaggatacc     360
cgggtggtga tcatcaatgc gttcttctcg gccttggtct tcctccgtgc tacggaggct     420
cttgcacccg aggactacac cccgccaacc tcggcactat ttgccgctgc tcaggaggga     480
aaggctaagc tgtttgccat cttggcggt cagggcaata tcgaggagta ctttgacgag     540
ctggcagaca tctacacgac ctataccacg ttggtgcagg actacgtcga ggacatggct     600
gcagtgttgc gcgagcacgc cagatcggat gatgcctcgg tcttccactc caagggactg     660
gatgtcatgg ggtggttgag gagcccagac tcgaagccag atgttgcgta tctggtttca     720
gcacccgtct ctctgccctt gattggactt gtccagctta tgcattacta tgtgatgctc     780
aaggttcttg accagactcc cgcccagctt cgcgatgtta ttcttggttc gacgggacac     840
tcccagggca tcatctcgtc tgtggtcatc tcatcctcgg ccacattcga ggagttcttt     900
gctaactctc gtaaggcact gggacttctt ttctggatcg aacccgctc ccaggaggtc     960
taccctcaaa ccaccctcaa tcccgccatt cttcaagact cgctctctaa caatgaaggc    1020
aaccctactc ctatgctggt tgtcaactct ttgcgcgcat ctgaggtcca gaagtacgtc    1080
gaggccacca accgccattt gccagaggac cgcaagatca agatcgcgct tattaacgga    1140
ccccgctcat ctatctgcac gggacctcct caatcgttgt acggcctgaa ccttgctctt    1200
cgcaagctca aggctcccac gggcctggag cagggtcgtg tacccttttc gcagagaaag    1260
gtcaagttct cgtcccgttt cttgcccatc actgcaccct ccactcttc gtatctggat    1320
ggcgtctctg ccctggtcga gagcgatatt gctcggtacg acctgaggtt tgaccatacc    1380
cagatgacca tccccgtctt ctcaaccgac tctggaaagg acattgcagg atcgcctact    1440
attactacgg accttgtcaa tcaaatttgt tcccttcccg tgcactggga aaggcgact    1500
gctatggcag gattgaccca tgtgatcgat ttcggccccg gcggctcctc gggcgtcggc    1560
tctttgacgg cccgcaacaa ggacggcacg ggtgtccagg tgatgctggc cggcgcttct    1620
gagggcgtca accgcgagct gtcgtacaaa cccgacatct tcgatgccaa cccagctgct    1680
ctgcgctatg cccccaactg ggccaatgag ttccagccaa gctggttcg ctccgtcaac    1740
ggcgagatcc acatcgacac tcgcatgtcc cgcctccttt ccaagccccc attgatggtc    1800
gccggaatga cccctcgac tgttaacgag gctttgtca gtgctgttat gaatgccggt    1860
taccacgttg agctggccgg tggtggacac tataacgagg ccgcggtccg cagcaaggtc    1920
aagaagatca tgcagctcac cactcctgga gccggtatca ctctcaacac cctcttcatc    1980
aatgtgcgcc agtgggcctt ccaagctccc ttggtgccca agctccgtcg cgagggcctc    2040
```

-continued

```
cccatggagg gcttttgttg cgctgccggt gttccctcgc tcgaggtcgc agacgagttc      2100
atcactgaca tgctcagtgc cggaatccgt cacatctcct tcaagcctgg ctcggccgag      2160
gccatccgcc aggtcttggc gatcgccaat gcccaccctg agatgcccat cgttcttcag      2220
tggactggtg gccgtgctgg tggccatcac agtttcgagg atttccatca gcccatcctg      2280
gagacatact ctgccatccg tcgtcaccct aacgttgtcc tggtggccgg ctctggtttc      2340
ggtggcgctg aggacaccta cccctacctc acaggtgact ggtctgtcca gctcgactac      2400
cctcccatgc cttttgatgg tatgcttttt ggttcacgcg tcatggtggc caaggaggga      2460
atggcttcgc ttggtgtgaa gcaggctatt gtcgatgcac ccggagtcga ggactctgag      2520
tgggaaaaga cttacaaggg acccaccgga ggcgtcatga ctgtccgttc cgaattggga      2580
gagcccattc ataaaattgc aacccgcgga gtcaagctgt ggaaggagat ggacgacacc      2640
atctttgctc tgcccaagga caagcgtccc gctgccctct␣ggccaagaa ggactacatc      2700
atcaagcgtc tgaacgctga cttccaaaag gtctggttcg gtaagaaggc caacggcagc      2760
gttgctgatc ttcaggacat gacttatgag gaggtcatca accgcttgat tgagctcatg      2820
tttatcaagc atgaggagcg ctggattgat cactctcacc gcaacttgct cggcgacatc      2880
cttcgccgga ttgaggagcg cttcgttggc gttgagaaga agtccattgt ccaaaccttc      2940
tctcagcttg acatcccttt tgcgtttgcc caggagtttg tcgacaccta tcccctgacc      3000
aagacccagc tcttgactac cgaggatgtt ggatacttct tgttcttgat gaaccgtcgt      3060
ggacaaaagc ccgtgccatt cattcccgtg ctcgacaagg actttgaggt gtggtttaag      3120
aaggactctc tctggcaggc cgaggacttg gccgctgttg ttgatcagga tgtgcagcgc      3180
acctgcattc ttcagggacc tgccgccgtc cgctatgcaa ccaaggtgga tgagcccgtc      3240
aaggatattt tggacggcat cttccacagc cacattgcct ggttgaagga gcgttattac      3300
aacaacaacg atgccaacat tccccaggtc gagtactttg gcggcaagcc cggacgcttc      3360
gagtccgcct tggatgctgt cttgcccttg gtcaaggtcg agacttacga caacggcaag      3420
gtcaagatgg tggagacctc catgctagag tcaagcttgc ccaagaatga ggattggctc      3480
gagtaccttg ctggccagga cccctcttgg ttccgcgccc tcttgactgc ccccgccgtc      3540
attcaaggca agaagttctt ggataatcct cttgcacgca tcttccgtcc tcgtgtctct      3600
caagccgttc acttcgagta cgccgaggac aagttgcaaa ccattaccgt ttacgatcgt      3660
cgctcctggt ctgcttccag caagtcgagc gagctctctc cctcgcttcg cgcccgtctg      3720
cagcccaacg agctcattga ggtcgtgctg gtggagaaga acggcgagcg tttgattcct      3780
ttccctctcc tcttccacta caccccgag aagggatatg cccctatcca tgaggtcatg      3840
gagggtcgca acgagagaat caaggagttc tactacaagc tttggttccc ttcagaggag      3900
gatcaattca acgcctgcct ggccactgat gccttcaccg aaaagtttat ttgcaatggt      3960
gagcaggtca gcacgccaga gatcaaggag ttttgccagg ctgtcggaaa ccaggccgag      4020
ctctacgttg agcgccgcca gaaagttgtc tatgcgccca tggattttgc tattgtcgtt      4080
ggctggaagt ctatcatcaa ggccatcttc cccaagtcga ttgacggtga tctgttgaag      4140
cttgtccatc tctcgaacgg cttccgtatg ttagatggcg ccgagtcctt gaagcaaggc      4200
gacattgttg acactgttgc cgagatcaat gccgttgtca caacgattc cgggaagttg      4260
gttcaggtca agggcgtggt tctgcgtgag ggcaagcgcg tcatggaggt gacctcggag      4320
ttcttgtacc gcggcacctt tgtggattac cagaacacat tccaaaagac ggttgagacc      4380
cccatggagg ttaagctgac gtccgccaag gatgtggctg tcttgaagag caaggagtgg      4440
```

-continued

```
atccagtggg ccgagggtga gcacaccgtc gggcctaatg cgtccttggt cttccgcctg    4500
aacacgattg ttcgcttcaa gaacaagacc accttctcgc atgttgagac cactggtacc    4560
gtgtcgatgc agatttccac taaggagcat gtcgagattg ccactgttca ctatagcaac    4620
gacgaggaga ctcagggaaa tcccgtcctc gcctacttga agcgctcggg ttctcctatc    4680
gagcaggcca tccacttcga gaacggtgga tattctgtca tgcccgaggg ttccttcagc    4740
tcggaggtca tttctcccTT cagcaatgag ccctatgcta aggtttcggg tgactttaac    4800
cctatccacg ttaacccTTA ctttgctgat ctcgctgagc tccctggcac tattacccat    4860
ggcatgtgga ctagtgcctc gacccgcaag tttgtggaga tctttgctgc agagaatcat    4920
cctcagcgtg tcactagcta cgaggtcaag ttcctttcta tggtgcttcc tcaggaccgt    4980
cTTTcgacca agttatcgca cattggaatg atcaacggaa agaagatcat caaagtggaa    5040
acTTTcaacc agaacggcag caaggttgtt gagggcactg ctgagattga tcagcccacg    5100
atcgcctatg tgttcactgg acagggatct caggagcagg gaatgggaat ggctctgtat    5160
gactcttccc ccgtcgccaa ggacatctgg cagagagccg accgtcattt cttggaaaac    5220
tatggcttct ccattctgga tattgtccgc aacaatcctc tgaagaagac gattcactTT    5280
ggtggtccca agggtaacgc cattcgtcag aattacatgt cgatgcgcta cgatcaagtt    5340
gaccaggatg gctccatcaa atctttgcct ctgttccccg gcatcaacga gaccacgcac    5400
TTTtacaccT Tccagtcacc caacggtctt ttggctgcca ctcagttcac acagcctgcc    5460
Ttgaccctta tggagaaggc cgccttcgag gacatgcgct ccaagggtTT gatccagggc    5520
aactgtgcct ttgccggtca ctcgctcgga gagtactctg ctcttgctgc cattggtgag    5580
gtccttccca tcgaatcctt ggttgatgtc gtcttctacc gtggtatgac catgcaggtc    5640
gctgttcccc gcgactctgt cggccgctcc aactatggaa tggtcgccat caacccatcg    5700
cgtgtctcgc ccacattcaa cgactctgct ctccgctatg tcgtggacgc aatcgccaga    5760
cagtcgaacg gtcTTTTgga aattgtcaat gagaacgttg agaactggca gtatgttgct    5820
gctggtgagc tTTctaactt ggacgctctc tcgactgtcc tgaactacct caaggtgcag    5880
aagatcgatc ttcagaagct gatggagacc atgcccttgg aagaggtcaa gaagcacctg    5940
tctcagatca ttgccggcgc ccttgagaag gttgccgaga aggttgccaa ggatggtcac    6000
atcaagcctg agcgcggtgt tgctaccatc cccttggctg aatcgatgt  ccccttccac    6060
tctagcttct tgttgtccgg tgtcgctccc ttccgcacct atctcgccaa gaagatcaac    6120
cctacgttca ttaacgtgcc cctgttgact ccaagtaca ttcccaatTT gactgctcag    6180
cccTTcagca ttgagaagtc ctacattgag ggcgtctaca acctcacgtc gtctccccgt    6240
ctggccaagg tcctcaagaa ctggatcgac accaagctga ctgccaagca gcagcagcgt    6300
ctgggatata ctctcttggt cgagttgctc gcttaccagt tcgcttcgcc cgtccgttgg    6360
attgagaccc aggatagact cttcaaggag tacaacgtcg tccgcttgat tgaggttgga    6420
ccctcgccca cgctctgtgg tatggcccaa cgcacgctca gttcaagta cgaggcttat    6480
gatgatgcct tgaccttcca gcgttcgact ctttgcacgt ccaaggactc caaggagatt    6540
tattatgcca tggacaatgt cgagtcctcg gctcctgctc cggctgccag tgctgctgct    6600
cccgccccca agccacccc  agttgccgct gcagccccg  ctcccgtggc tgtcgccgct    6660
gcaggacctg ctgccgccgt ttcagatgtc cccatcaagg cccttgagat cttgcatgtg    6720
atcgttgccc aaaaggtcaa gaagactctc gaagaggtcc ctctctcgaa ggccatcaag    6780
gatcttgtag gaggcaagtc gactcttcag aacgaaatct gggtgatct  tcagaaggag    6840
```

```
tttggtagca gcggattccc tgagaagggc gaggaggctc ctctggagga gcttgccaac   6900
gctcttcagg gcaacttcaa cggagctctt ggaaagcaga ccacttcgct catcgccaag   6960
atgattggat ccaagatgcc cggtggttat tcgctctcga ctgccaaggg atacctggcc   7020
aaggcccacg gcctgggtcc tgtccgtgcc gatgctgcgc tcttggtcgg tttgacgatg   7080
gagcccgcag cccgtctggg cgccgttcct gaggccaatg cttggttgga ttcggtcgct   7140
caggcttacg cccgccgtgc tggtatctcg ctgtcggctg gtgccccgc tggtggtgcc    7200
gctcccgtca tgatggcggc tgctggccct gctgctgctg tcctgcagc tgctgttgct    7260
gatgctccta tcaaggctat tgacattctt cacgtcattg ttgcccaaaa gatcaagaag   7320
actgtcgagg aggtcccact ctcgaaggcc atcaaggatc ttgttggtgg caagtcgact   7380
ctgcagaacg agatcttggg tgatcttcag aaggagtttg gcagcagtgg cttccctgag   7440
aagggcgagg aggctccttt ggaagatctc ggaaatgctc tccagggtaa ctttggtgga   7500
tccttgggca tgcagacgac ctcgttgatt gccaagatga tgggatccaa gatgccaggt   7560
ggatttaccc agtcctcagc caaggcttac ctcgcctcgt cttatggctt gggtccactc   7620
cgcgctgacg gtgcgttgct cttgggtgtc actatggagc ccagcgcccg cctcggatcc   7680
gagggtgatg ccaaggcttg gttggacact gtcgcccaag cttacgctcg tcgtgccggt   7740
atttccttgg gaggcggcgg cggcggtgct gtcgctggtg gtgccgttgg tggtgccatg   7800
atgaacagtg aggagttcaa ccaattccag gccaagcaga acgcgatgat gtaccagcac   7860
ctcgagatct atgctcgtta ccttgagaag gatctccgtg ctggcgaaaa gcagtacgag   7920
gaggagaagc tggcgaccct gcgcttgcag gcagatatcg accagtggat ggctgagcac   7980
ggcgactact acgccgaggg catcaagcct gccttcagcg ccaagaaggc ccgcaagtac   8040
gactcacact ggaactgggt ccgtcaggat gccatgtcgc tcttgtacga catgatcttt   8100
ggccgactca ccgtcgttga ccgcgaggtc gtgcccagt gcatccatgt catgaaccgc    8160
gctaaccccc agttgcttga gtttatgatc taccacattg acaacactgc tgctgatcgc   8220
ggcaagacct atgctttggc caaggagttt ggtaacatgt tgatcgagaa ctgtcgcgag   8280
gttctggaag ccgcgcctgt ctacaaggat gtcggtgttc ctaccggtcc ccagacgacg   8340
atcgataaca agggcaatat cttgtacgag gaggttcagc gcgtgggtgt ccgcaagctg   8400
gatcactatg tcaaggatat ggtcgctggt ggcaagatgt ccgagtacag caaccgccag   8460
aaggtgcaga agaaccttgc tcagatctac aagatcatta aggctcagaa cacgatgaag   8520
tcttcctcca agttggcgat caagtcactc tacggcgagg tcatccatgc catgaacatg   8580
tccaacacca tcatccgtga ggagaagaac cgccgtgcca gccgcgtccg ccgcgcctcg   8640
gccgttccca gcgccgaccg ccctaagaag gaggccaaga aggagaccat tcccttcttg   8700
cacctcaaga agaagaaccc ccagtctgag agcggatggg agttcagtca gcgtttgaca   8760
agcgtttact tggatgtctt gaccaacatt gcgcgcgacg tgttacatt tgagaaccgc    8820
atggtcctga tgaccggtgc tggaaaggac tcgatcggag cctcgatcct caagggtctc   8880
ttgtccggag gagccaaggt tgttgtcacg acctcgcgct tcagccgtga tgtgaccgag   8940
tactaccaat cgatctacca gcgccacgga tccaagaact catgcttggt tgttgttccc   9000
ttcaacggag gctccaagca ggatgtcgac gcacttgtca actacattta cgataaggat   9060
ctcaagaagg gtcttggctg ggatctcgac tacatcatcc ccttcgctgc catctcggtc   9120
cagggcaagg agattgacaa catcgactcg cagtccgagc tggctcaccg tatcatgttg   9180
accaacgttt tgcgtctgct cggaaacgtt aaggccaaga agatggagca cggctacgac   9240
```

```
actcgccctg ctcaggtcat cctgcccttg tcgcccaacc acggaacctt cggagctgac    9300
ggtctctatg gtgagtctaa ggttgctctc gagaccttgt tcaaccgctg gagttccgag    9360
tcttggggcg cctatctgac catcaccgga gccgttattg gctggactcg cggtactgga    9420
ttgatgagcg gtaacaacat tgtggccgag ggcctggaga agtacggtgt ccgcaccttc    9480
tctggccagg agatggcatt caacattctc ggtctcatgc atccctcgat caccaacctc    9540
tgccaggtcg agcctgtctg ggccgacttg aacggtggtc ttcagtactt gcccaacctg    9600
aacgaaatct cggccaactt gcgtgccgaa taccgccaga cggccgagat ccgcaaggcg    9660
atcgtcaccg agaacactct ggatttcaag gagacccacg tgctgaggc cgagcgtaag    9720
caccaacccc acaaggtcac gcctcgtgcc aacatgaaat tccctttccc tgagctgaag    9780
gactacaagg acctgtcgca cgctcacaag ctccgcggca tgctcgatct tgagaaggtt    9840
gtcgtcgtca ctggtttctc tgaggtcgga ccttgggta actcgcgcac tcgctgggaa    9900
atggaggcta atggccagtt ctcactcgag ggatgcattg agatggcctg gatcatgggc    9960
ttcatcaaac atcacaatgg taacctcaag tctggctccc cttactctgg ctgggtcgat   10020
gccaagactg aagagcccgt caaggatcgc gatgtgaaag ccaagtacga gaagcagatc   10080
ttggagcaca ctggtatccg tctgattgag cccgagctct ttgaggtta tgatcccaag   10140
cgtaagggac tgcttcagga ggtcttgatc gaccatgatc ttgaggcctt tgaggtctcg   10200
aaggaggagg cccagatgtt caagcttgag cacggcgaca aggtcgacat ttacgaggag   10260
gagtctggtc agtgggccgt caagttcaag aagggcgcta acatgtatat tcccaaggcc   10320
ctgaagttcg atcgtcttgt tgctggccag atccccactg gatgggatgc tgcccgcttt   10380
ggagtaccca aggacatcat tgaccaggtc gatactatta ccctttatgt cttggtctcg   10440
accgtggagg ccttggttgc ctcgggtatc actgatcctt atgagttcta ccagtacgtt   10500
cacgtgtctg aggttggaaa tacagctgga tccggtgtcg gaggcatgct ctcgcttcgc   10560
ggcatgtacc gcggtcgcgt gatggatgat cctgtgcaga aggatatctt gcaggagtcc   10620
ttcatcaaca cgatgcctgc ctgggtcaac atgctgctcc tgtcatcctc tggacctatc   10680
aagacacccg tcggagcttg tgccaccgct gtcgagtctg tcgagattgg tgtggatacg   10740
atccagagcg gtaaggcaaa gattgtgatt gtcggaggct acgatgactt ccaggaggaa   10800
ggttcgtacg agtttgccaa catgaaggcg accagcaaca ccgaggaaga gtttgcgcat   10860
ggacgtacgc ccaaggagat gtcccgcccct gcaacctcga cccgctctgg attcatggag   10920
tctcacggag ctggtattga gattttgatg caggccaagc ttgccgtgga gatgggtgtg   10980
cccatttacg gtatcgtcgg tctcaccaac actgccaccg acaaggaggg tcgctctgtt   11040
ccagctcctg gacagggtgt cctcaccact gctcgtgagg ctaagggcaa gatgccttcg   11100
cgccttctgg acatcaagta ccgcaagcgc cagatcgatt cccgccgagc tcagattaag   11160
caatgggtcg agaacgagta tgctgagctc cgctacgagc tcgatgagct caaggccagc   11220
aacagcctca ccgtctcgga agaagagtat cttgctgctg agactgagcg cattcagaag   11280
gaagccaagc gtcagcaccg cgaggccctt aacctgtggg gcaatgagtt ctacagacag   11340
gaccctcaga tcgctcctct gcgtggtgcc cttgcctcct ttggcttgac gatcgatgac   11400
attggtgttg atccttcca cggtacctcc accaaggcca acgacaagaa cgaatccgaa   11460
gtcgtcaaca agcagctcga gcatttgggt cgcagcaagg gtaacgcttt gccctctatc   11520
tggcaaaagt acctcacggg acatcccaag ggtgctgctg ctgcctggat gatgaacggt   11580
gtcctgcaag tcctccagac gggtctcatt cccggaaacc gtaacgccga caacattgac   11640
```

-continued

```
gacacaatga gacagtatga gcacgtcttg tacacctcgc ggtcgattca gactgatggt    11700
gtcaaggccg gtctgctcaa atcgttcggt ttcggccagg tcggaggtga agttctcctg    11760
atccactcgg attacattct tggtgcattg gaggagcacg agtacgaggc ttacaaggtc    11820
aagcagcagg cgcgccaggc caagtcgtac cggtacttgc atgactctat gaccggcggc    11880
cctgccctgg tccaggtcaa gaacgctccc ccatactcgc ccgagctcga gtccccgtg     11940
tacttgaacc ccaaggcccg tgcgcagtac aacaacgcga ccaagtcctg ggcgttcaac    12000
gctaagcacc tggtacccga gtctgacaag attgatgtgg acatgacgcg tgcgattctg    12060
gagacgtccg ctcaagagtc attaggtgtg acgtcctcgt cttcgcgcgg tgtgggtgtg    12120
gatgtggaaa tggtctctgc gatcaacatt gagaacgaca cgttcttgga gcgtaacttt    12180
acccagcagg agattgacta ctgtctgagc cgaccggatc ctcaggctag ctttgctggt    12240
cggtggtctg ccaaggaggc cgtggttaag gccgtttcgt cgttctcgct cgactctgag    12300
aaggtgtgga cacagggtgc aggagcggga ctgagtgaga ttgagattgt gatggcgagg    12360
agcggcgcac cctcggtggt gttctcgggt gcggcccagg aggcggcggc caaggccggc    12420
gtcaaggaga tcaaggtctc gatcagccat tctggcgcgt acgcggttgc ggttgcaaat    12480
gcgttgtaaa aacctcccct ctccttcaag tgttcttgtt ctttcatttt ttctttcgtt    12540
cttttaattg cgcttgcttg tgctttcttc agtagagttc tcttttttct ttcttcattc    12600
tatttcttta cttcttatac cttttcatgg gcccttgtat acaaacaact tataaataaa    12660
aagggtgttc tgcgggtggg gtgggaggcg ggccacgatg ggtttcaagc aggtatgatg    12720
gaagaaggct ctacattctc aagagaacag ctggggagtg acaggttgag ttgaacgcaa    12780
cgcttctctt cttgcctcct ttattttcta gttctcccga gtcccttctt gactacttgg    12840
cttacgcaac aagtacccag cgcgcctcct tcaccttcac ttacgagagc aatatctcta    12900
aaaaaaaaaa aaaaaaaaaa ctcgac                                         12926
```

<210> SEQ ID NO 2
<211> LENGTH: 15539
<212> TYPE: DNA
<213> ORGANISM: Mortierella alpina

<400> SEQUENCE: 2

```
tccagggttc cagggttcgg agaatataat aaatctttga aagagagaca gaggaggcag      60
aggcaattca tcttgggatc gactgggatg cgagagacag agggcgttgt ttatttaatg     120
tagtagtgca gcacatcaat gacctatagg gcaatgatgg tagtgggtgg tgactagagg     180
cgccaggacg acgcaagcat agatgcagct aatcgtgcag tgtgcagcga cagtgatggg     240
ctgccctgaa tctgcacgca aggacagcgg tgctatgtcc aaatcgagaa ggcgggttcc     300
agagggacag cgcgacagac tggtccaaat gttggggca atctcgcagc tggctgggtt      360
tgagacgaag aagccgagag tgaaaatttt gttctatcgg aggaatgggg ggacggaggc     420
cgtgctaggg ccttgtggga agccaggctc atcgtatggc ctgccagggc tggtgagaag     480
gagctcgctt agaccccccc acaatgttgg atgggagtg tgcaagagca atcaaaagta      540
ccaaaaaaaa aaaaaaaaaa ataagatcct gccctatcag ctggataaga tatccgcttg     600
ctgtaggtgt cgtatgtgtt gtggtgtatt gcggatcaag cttcaaggtg ctgttggtg      660
ttatattatt ccttgcgctg gaacccttt cgctttcttt tcttcctctc ttcttcccca      720
tcctccacct ccatctccct ccgcaatctt ctttcctccc tcagcctctt catctcgaca     780
ctccgcatcc tttgttcatt actcattatt gcatagaaca acctgcaatc tcctttgtat    840
```

-continued

```
tccttctgta tctacctcgc atctcctcct gttctcttgc attatcgtct ttcacaccca      900
cctctatctc tttctcgaaa gcaagaacat cctattgaaa agttgcattc aattgtcctt      960
tgttctcttt gaaaaagtta accgctgaaa gccgatactt catcctttat atcatccaaa     1020
agaaaacata tctaaaaaaa ccagaacgcc ttttcttaat catgactacc gcacagtcca     1080
acttgacccg tcctttggcc ctcaagcaag gaacttctga ggtctcgatc ctcgttcctt     1140
cggatgtctg ggtagcggct gaacaacttc gtgaggagtt tctgatctcg gtcgaggctg     1200
ctcctgcaga ggaggccgca gcgaccggaa gtgctgacga tcaggccccg gagatggctt     1260
tggtggcccg ttttctcaaa tttgctacgg acaagagcga gcaggtaaag gaacatgcta     1320
cgcttcattc ttgtttagca tcgacattgg cagtggtggg tggttgggat tggggttttg     1380
tatatagttt ttcttgcgtg ctaggaacgc agcggaaaag cagcagcctc aatggcagga     1440
agtgcgtcag agaaacagga aagaccagat gcgactcttt ttttttttg tttttgttt      1500
cttgggttgt agggcaggag gcgatctgga gattgtggca gaaaaggctg ccctcagacc     1560
atgtaacacc caacaaaaaa aaagtgaaca gaataaggaa ggggagcgtg tgttaccata     1620
ccttttgatt tggacccttc ttcttcaaga gagagggatg catgcacaca tcagcctctc     1680
cgagggataa caagggcggg atctctcacc tcatcgtcgt tttcccccct ccttttccgc     1740
cttcaatgct gacggagtgg gaagtggagg aggtggatat cgttgagagc ggggcggggt     1800
cagcgagacg gtcaaagagc ggatcgtaaa aaaaaaaaa aaagcgctgg ctagttcttt     1860
cccttgctct tattttggg tcttttcctt tcaccacgac caaaaaaaaa aaaaaaaaaa     1920
aaaaaaaaa aaaattaaa tttagcgttt caatgaaagg gtgagagagt ggtggtacat      1980
ttggtttccc acgatctgct tgcagatgtg caaccgacg tgcaggccgc cttcagggtt     2040
actgggcgtg attctgtatg gctttgacca aagcagccgt aaggcaagag ctaacagcaa     2100
gtcgatgcac cactttcttc ttttcttttt gtactataga gcgatccttc actgcagttc     2160
attcctgtgc tgagaaccgt cttcctgttc tttgtcacca ataccttaa aggaaacgac      2220
atccacgcgg tcactcgact tttagcaaag gataccggg tggtgatcat caatgcgttc      2280
ttctcggcct tggtcttcct ccgtgctacg gaggctcttg cacccgagga ctacaccccg     2340
ccaacctcgg cactatttgc cgctgctcag gagggaaagg ctaagctgtt tgccatcttt     2400
ggcggtcagg gcaatatcga ggagtacttt gacgagctgg cagacatcta cacgacctat     2460
accacgttgg tgcaggacta cgtcgaggac atggctgcag tgttgcgcga gcacgccaga     2520
tcggatgatg cctcggtctt ccactccaag ggactggatg tcatggggtg gttgaggagc     2580
ccagactcga agccagatgt tgcgtatctg gtttcagcac ccgtctctct gcccttgatt     2640
ggacttgtcc agcttatgca ttactatgtg atgctcaagg taagagcaac tacaggtcaa     2700
tacaccaagt tgagaatcat caactccaca gatgctgacc ccattatatt cattcaaaac     2760
tttaaacgcg gtaacaggtt cttgaccaga ctcccgccca gcttcgcgat gttattcttg     2820
gttcgacggg acactcccag ggcatcatct cgtctgtggt catctcatcc tcggccacat     2880
tcgaggagtt ctttgctaac tctcgtaagg cactgggact tcttttctgg atcggaaccc     2940
gctcccagga ggtctaccct caaaccaccc tcaatcccgc cattcttcaa gactcgctct     3000
ctaacaatga aggcaaccct actcctatgc tggttgtcaa ctctttgcgc gcatctgagg     3060
tccagaagta cgtcgaggcc accaaccgcc atttgccaga ggaccgcaag atcaagatcg     3120
cgcttattaa cggacccccgc tcatctatct gcacgggacc tcctcaatcg ttgtacggcc     3180
tgaaccttgc tcttcgcaag ctcaaggctc ccacgggcct ggagcagggt cgtgtaccct     3240
```

```
tttcgcagag aaaggtcaag ttctcgtccc gtttcttgcc catcactgca cccttccact      3300
cttcgtatct ggatggcgtc tctgccctgg tcgagagcga tattgctcgg tacgacctga      3360
ggtttgacca tacccagatg accatccccg tcttctcaac cgactctgga aaggacattg      3420
caggatcgcc tactattact acggaccttg tcaatcaaat ttgttccctt cccgtgcact      3480
gggagaaggc gactgctatg gcaggattga cccatgtgat cgatttcggc cccggcggct      3540
cctcgggcgt cggctctttg acggcccgca acaaggacgg cacgggtgtc caggtgatgc      3600
tggccggcgc ttctgagggc gtcaaccgcg agctgtcgta caaacccgac atcttcgatg      3660
ccaacccagc tgctctgcgc tatgccccca actgggccaa tgagttccag ccaaaagctgg     3720
ttcgctccgt caacggcgag atccacatcg acactcgcat gtcccgcctc ctttccaagc      3780
ccccattgat ggtcgccgga atgacccct cgactgttaa cgagggcttt gtcagtgctg        3840
ttatgaatgc cggttaccac gttgagctgg ccggtggtgg acactataac gaggccgcgg      3900
tccgcagcaa ggtcaagaag atcatgcagc tcaccactcc tggagccggt atcactctca      3960
acaccctctt catcaatgtg cgccagtggg gcttccaagc tcccttggtg cccaagctcc      4020
gtcgcgaggg cctccccatg gagggctttt gttgcgctgc cggtgttccc tcgctcgagg      4080
tcgcagacga gttcatcact gacatgctca gtgccggaat ccgtcacatc tccttcaagc      4140
ctggctcggc cgaggccatc cgccaggtct tggcgatcgc caatgcccac cctgagatgc      4200
ccatcgttct tcagtggact ggtggccgtg ctggtggcca tcacagtttc gaggatttcc      4260
atcagcccat cctggagaca tactctgcca tccgtcgtca ccctaacgtt gtcctggtgg      4320
ccggctctgg tttcggtggc gctgaggaca cctacccta cctcacaggt gactggtctg       4380
tccagctcga ctaccctccc atgccttttg atggtatgct ttttggttca cgcgtcatgg      4440
tggccaagga gggaatggct tcgcttggtg tgaagcaggc tattgtcgat gcacccggag      4500
tcgaggactc tgagtgggaa aagacttaca agggacccac cggaggcgtc atgactgtcc      4560
gttccgaatt gggagagccc attcataaaa ttgcaacccg cggagtcaag ctgtggaagg      4620
agatggacga caccatcttt gctctgccca aggacaagcg tcccgctgcc ctcttggcca      4680
agaaggacta catcatcaag cgtctgaacg ctgacttcca aaaggtaaat aagtcgttgc      4740
cgttgtactc acgctcggct ggtatactta catgccgcgc gcaaccagtt attaaccagc      4800
tagcatgtga ttatggtatt aggtctggtt cggtaagaag gccaacggca gcgttgctga     4860
tcttcaggac atgacttatg aggaggtcat caaccgcttg attgagctca tgtttatcaa      4920
gcatgaggag cgctggattg atcactctca ccgcaacttg ctcggcgaca tccttcgccg      4980
gattgaggag cgcttcgttg gcgttgagaa gaagtccatt gtccaaacct tctctcagct      5040
tgacatccct tttgcgtttg cccaggagtt tgtcgacacc tatcccctga ccaagaccca      5100
gctcttgact accgaggatg ttggatactt cttgttcttg atgaaccgtc gtggacaaaa      5160
gcccgtgcca ttcattcccg tgctcgacaa ggactttgag gtgtggttta agaaggactc      5220
tctctggcag gccgaggact ggccgctgt tgttgatcag gatgtgcagc gcacctgcat       5280
tcttcaggga cctgccgccg tccgctatgc aaccaaggtg gatgagcccg tcaaggatat      5340
tttggacggc atcttccaca gccacattgc ctggttgaag gagcgttatt acaacaacaa      5400
cgatgccaac attccccagg tcgagtactt tggcggcaag cccggacgct tcgagtccgc      5460
cttggatgct gtcttgccct tggtcaaggt cgagacttac gacaacggca aggtcaagat      5520
ggtggagacc tccatgctag agtcaagctt gcccaagaat gaggattggc tcgagtacct      5580
tgctggccag gaccccctctt ggttccgcgc cctcttgact gccccgccg tcattcaagg     5640
```

```
caagaagttc ttggataatc ctcttgcacg catcttccgt cctcgtgtct ctcaagccgt    5700
tcacttcgag tacgccgagg acaagttgca aaccattacc gtttacgatc gtcgctcctg    5760
gtctgcttcc agcaagtcga gcgagctctc tccctcgctt cgcgcccgtc tgcagcccaa    5820
cgagctcatt gaggtcgtgc tggtggagaa gaacggcgag cgtttgattc ctttccctct    5880
cctcttccac tacaccccg agaagggata tgcccctatc catgaggtca tggagggtcg    5940
caacgagaga atcaaggagt tctactacaa gctttggttc ccttcagagg aggatcaatt    6000
caacgcctgc ctggccactg atgccttcac cgaaaagttt atttgcaatg gtgagcaggt    6060
cagcacgcca gagatcaagg agttttgcca ggctgtcgga aaccaggccg agctctacgt    6120
tgagcgccgc cagaaagttg tctatgcgcc catggatttt gctattgtcg ttggctggaa    6180
gtctatcatc aaggccatct tccccaagtc gattgacggt gatctgttga agcttgtcca    6240
tctctcgaac ggcttccgta tgttagatgg cgccgagtcc ttgaagcaag gcgacattgt    6300
tgacactgtt gccgagatca atgccgttgt caacaacgat tccgggaagt tggttcaggt    6360
caagggcgtg ttctgcgtga agggcaagcg cgtcatggag gtgacctcgg agttcttgta    6420
ccgcggcacc tttgtggatt accagaacac attccaaaag acggttgaga cccccatgga    6480
ggttaagctg acgtccgcca aggatgtggc tgtcttgaag agcaaggagt ggatccagtg    6540
ggccgagggt gagcacaccg tcgggcctaa tgcgtccttg gtcttccgcc tgaacacgat    6600
tgttcgcttc aagaacaaga ccaccttctc gcatgttgag accactggta ccgtgtcgat    6660
gcagatttcc actaaggagc atgtcgagat tgccactgtt cactatagca acgacgagga    6720
gactcaggga aatcccgtcc tcgcctactt gaagcgctcg ggttctccta tcgagcaggc    6780
catccacttc gagaacggtg atattctgt catgcccgag ggttccttca gctcggaggt    6840
catttctccc ttcagcaatg agcccatagc taaggtttcg ggtgacttta accctatcca    6900
cgttaacccct tactttgctg atctcgctga gctccctggc actattaccc atggcatgtg    6960
gactagtgcc tcgacccgca gtttgtgga gatctttgct gcagagaatc atcctcagcg    7020
tgtcactagg ttagttcgtt ttcttttccg cattgcttga gagtatgcac tctagtattc    7080
tttccggcgt agctaattct tgattcttct ctctagctac gaggtcaagt tcctttctat    7140
ggtgcttcct caggaccgtc tttcgaccaa gttatcgcac attggaatga tcaacggaaa    7200
gaagatcatc aaagtggaaa cttcaacca gaacggcagc aaggtaaaac cagaaacgtc    7260
ttgttagcat ttcatgtgaa aaatcgcgta acctgttgga atcatttatt aacgttggca    7320
gcgattcatt tggcacaggt tgttgagggc actgctgaga ttgatcagcc cacgatcgcc    7380
tatgtgttca ctggacaggg atctcaggag cagggaatgg gaatggctct gtatgactct    7440
tcccccgtcg ccaaggacat ctggcagaga gccgaccgtc atttcttgga aaactatggt    7500
atgtaccttg ccagcttttc ttgttatgat attcgttctc tttcgttatg ctgtaactga    7560
tcgattttgt tccttttgac aggcttctcc attctggata ttgtccgcaa caatcctctg    7620
aagaagacga ttcactttgg tggtcccaag ggtaacgcca ttcgtcagaa ttacatgtcg    7680
atgcgctacg atcaagttga ccaggatggc tccatcaaat cttttgcctct gttccccggc    7740
atcaacgaga ccacgcactt ttacaccttc cagtcaccca acggtctttt ggctgccact    7800
cagttcacac agcctgcctt gacccttatg gagaaggccg ccttcgagga catgcgctcc    7860
aagggtttga tccagggcaa ctgtgccttt gccggtcact cgctcggaga gtactctgct    7920
cttgctgcca ttggtgaggt ccttcccatc gaatccttgg ttgatgtcgt cttctaccgt    7980
ggtatgacca tgcaggtcgc tgttccccgc gactctgtcg gccgctccaa ctatggaatg    8040
```

```
gtcgccatca acccatcgcg tgtctcgccc acattcaacg actctgctct ccgctatgtc   8100
gtggacgcaa tcgccagaca gtcgaacggt cttttggaaa ttgtcaatga gaacgttgag   8160
aactggcagt atgttgctgc tggtgagctt tctaacttgg acgctctctc gactgtcctg   8220
aactacctca aggtgcagaa gatcgatctt cagaagctga tggagaccat gcccttggaa   8280
gaggtcaaga agcacctgtc tcagatcatt gccggcgccc ttgagaaggt tgccgagaag   8340
gttgccaagg atggtcacat caagcctgag cgcggtgttg ctaccatccc cttggctgga   8400
atcgatgtcc ccttccactc tagcttcttg ttgtccggtg tcgctcccct tccgcacctat   8460
ctcgccaaga agatcaaccc tacgttcatt aacgtgcccc tgttgacttc caagtacatt   8520
cccaatttga ctgctcagcc cttcagcatt gagaagtcct acattgaggg cgtctacaac   8580
ctcacgtcgt ctccccgtct ggccaaggtc ctcaagaact ggatcgacac caagctgact   8640
gccaagcagc agcagcgtct gggatatact ctcttggtcg agttgctcgc ttaccagttc   8700
gcttcgcccg tccgttggat tgagacccag gatagactct tcaaggagta caacgtcgtc   8760
cgcttgattg aggttggacc ctcgcccacg ctctgtggta tggcccaacg cacgctcaag   8820
ttcaagtacg aggcttatga tgatgccttg accttccagc gttcgactct ttgcacgtcc   8880
aaggactcca aggagattta ttatgccatg acaatgtcg agtcctcggc tcctgctccg    8940
gctgccagtg ctgctgctcc cgcccccaaa gccacccccag ttgccgctgc agcccccgct   9000
cccgtggctg tcgccgctgc aggacctgct gccgccgttt cagatgtccc catcaaggcc   9060
cttgagatct tgcatgtgat cgttgcccaa aaggtcaaga agactctcga agaggtccct   9120
ctctcgaagg ccatcaagga tcttgtagga ggcaagtcga ctcttcagaa cgaaatcttg   9180
ggtgatcttc agaaggagtt tggtagcagc ggattccctg agaagggcga ggaggctcct   9240
ctggaggagc ttgccaacgc tcttcagggc aacttcaacg gagctcttgg aaagcagacc   9300
acttcgctca tcgccaagat gattggatcc aagatgcccg tggttattc gctctcgact    9360
gccaagggat acctggccaa ggcccacggc ctggtcctg tccgtgccga tgctgcgctc    9420
ttggtcggtt tgacgatgga gcccgcagcc cgtctgggcg ccgttcctga ggccaatgct   9480
tggttggatt cggtcgctca ggcttacgcc cgccgtgctg tatctcgct gtcggctggt    9540
gcccccgctg gtggtgccgc tcccgtcatg atggcggctg ctggccctgc tgctgctggt   9600
cctgcagctg ctgttgctga tgctcctatc aaggctattg acattcttca cgtcattgtt   9660
gcccaaaaga tcaagaagac tgtcgaggag gtcccactct cgaaggccat caaggatctt   9720
gttggtggca agtcgactct gcagaacgag atcttgggtg atcttcagaa ggagtttggc   9780
agcagtggct tccctgagaa gggcgaggag gctcctttgg aagatctcgg aaatgctctc   9840
cagggtaact ttggtggatc cttgggcatg cagacgacct cgttgattgc caagatgatg   9900
ggatccaaga tgccaggtgg atttacccag tcctcagcca aggcttacct cgcctcgtct   9960
tatggcttgg gtccactccg cgctgacggt gcgttgctct gggtgtcac tatggagccc   10020
agcgcccgcc tcggatccga gggtgatgcc aaggcttggt tggacactgt cgcccaagct  10080
tacgctcgtc gtgccggtat ttccttggga ggcggcggcg gcggtgctgt cgctggtggt   10140
gccgttggtg gtgccatgat gaacagtgag gagttcaacc aattccaggc caagcagaac   10200
gcgatgatgt accagcacct cgagatctat gctcgttacc ttgagaagga tctccgtgct   10260
ggcgaaaagc agtacgagga ggagaagctg gcgaccctgc gcttgcaggc agatatcgac   10320
cagtggatgg ctgagcacgg cgactactac gccgagggca tcaagcctgc cttcagcgcc   10380
aagaaggccc gcaagtacga ctcacactgg aactgggtcc gtcaggatgc catgtcgctc   10440
```

```
ttgtacgaca tgatctttgg ccgactcacc gtcgttgacc gcgaggtcgt ggcccagtgc  10500
atccatgtca tgaaccgcgc taaccccag ttgcttgagt ttatgatcta ccacattgac   10560
aacactgctg ctgatcgcgg caagacctat gctttggcca aggagtttgg taacatgttg  10620
atcgagaact gtcgcgaggt tctggaagcc gcgcctgtct acaaggatgg tgagtctgct  10680
tttcttttca cccctctct cacatgtaac gcttaagatt atgatcagct agctaatgac   10740
atcctccttt tgtttgtttg tttttctaat agtcggtgtt cctaccggtc cccagacgac  10800
gatcgataac aagggcaata tcttgtacga ggaggttcag cgcgtgggtg tccgcaagct  10860
ggatcactat gtcaaggata tggtcgctgg tggcaagatg tccgagtaca gcaaccgcca  10920
gaaggtgcag aagaaccttg ctcagatcta caagatcatt aaggctcaga cacgatgaa   10980
gtcttcctcc aagttggcga tcaagtcact ctacggcgag gtcatccatg ccatgaacat  11040
gtccaacacc atcatccgtg aggagaagaa ccgccgtgcc agccgcgtcc gccgcgcctc  11100
ggccgttccc agcgccgacc gccctaagaa ggaggccaag aaggagacca ttcccttctt  11160
gcacctcaag aagaagaacc cccagtctga gagcggatgg gagttcagtc agcgtttgac  11220
aagcgtttac ttggatgtct tgaccaacat tgcgcgcgac ggtgttacat ttgagaaccg  11280
catggtcctg atgaccggtg ctggaaagga ctcgatcgga gcctcgatcc tcaagggtct  11340
cttgtccgga ggagccaagg ttgttgtcac gacctcgcgc ttcagccgtg atgtgaccga  11400
gtactaccaa tcgatctacc agcgccacgg atccaagaac tcatgcttgg ttgttgttcc  11460
cttcaacgga ggctccaagc aggatgtcga cgcacttgtc aactacattt acgataagga  11520
tctcaagaag ggtcttggct gggatctcga ctacatcatc cccttcgctg ccatctcggt  11580
ccagggcaag gagattgaca acatcgactc gcagtccgag ctggctcacc gtatcatgtt  11640
gaccaacgtt ttgcgtctgc tcggaaacgt taaggccaag aagatggagc acggctacga  11700
cactcgccct gctcaggtca tcctgcccct gtcgcccaac cacggaacct tcggagctga  11760
cggtctctat ggtgagtcta aggttgctct cgagaccttg ttcaaccgct ggagttccga  11820
gtcttggggc gcctatctga ccatcaccgg agccgttatt ggctggactc gcggtactgg  11880
attgatgagc ggtaacaaca ttgtggccga gggcctggaa agtacgcgtg tccgcacctt  11940
ctctggccag gagatggcat tcaacattct cggtctcatg catccctcga tcaccaacct  12000
ctgccaggtc gagcctgtct gggccgactt gaacggtggt cttcagtact gcccaacct   12060
gaacgaaatc tcggccaact tgcgtgccga ataccgccag acggccgaga tccgcaaggc  12120
gatcgtcacc gagaacactc tggatttcaa ggagacccac ggtgctgagg ccgagcgtaa  12180
gcaccaaccc cacaaggtca cgcctcgtgc caacatgaaa ttccctttcc ctgagctgaa  12240
ggactacaag gacctgtcgc acgctcacaa gctccgcggc atgctcgatc ttgagaaggt  12300
tgtcgtcgtc actggtttct ctgaggtcgg accttggggt aactcgcgca ctcgctggga  12360
aatggaggct aatggccagt tctcactcga gggatgcatt gagatggcct ggatcatggg  12420
cttcatcaaa catcacaatg gtaacctcaa gtctggctcc ccttactctg gctgggtcga  12480
tgccaagact gaagagcccg tcaaggatcg cgatgtgaaa gccaagtacg agaagcagat  12540
cttggagcac actggtatcc gtctgattga gcccgagctc tttggaggtt atgatcccaa  12600
gcgtaaggga ctgcttcagg aggtcttgat cgaccatgat cttgaggcct tgaggtctc   12660
gaaggaggag gcccagatgt tcaagcttga gcacggcgac aaggtcgaca tttacgagga  12720
ggagtctggt cagtgggccg tcaagttcaa gaagggcgct aacatgtata ttcccaaggc  12780
cctgaagttc gatcgtcttg ttgctggcca gatccccact ggatgggatg ctgcccgctt  12840
```

```
tggagtaccc aaggacatca ttgaccaggt cgatactatt acccctttatg tcttggtctc    12900 gaccgtggag gccttggttg cctcgggtat cactgatcct tatgagttct accagtacgt    12960
tcacgtgtct gaggttggaa atacagctgg atccggtgtc ggaggcatgc tctcgcttcg    13020
cggcatgtac cgcggtcgcg tgatggatga tcctgtgcag aaggatatct tgcaggagtc    13080
cttcatcaac acgatgcctg cctgggtcaa catgctgctc ctgtcatcct ctggacctat    13140
caagacaccc gtcggagctt gtgccaccgc tgtcgagtct gtcgagattg tgtgtggatac   13200 gatccagagc ggtaaggcaa agattgtgat tgtcggaggc tacgatgact tccaggagga    13260
aggttcgtac gagtttgcca acatgaaggc gaccagcaac accgaggaag agtttgcgca    13320
tggacgtacg cccaaggaga tgtcccgccc tgcaacctcg acccgctctg gattcatgga    13380
gtctcacgga gctggtattg agattttgat gcaggccaag cttgccgtgg agatgggtgt    13440
gcccatttac ggtatcgtcg gtctccaccaa cactgccacc gacaaggagg gtcgctctgt    13500
tccagctcct ggacagggtg tcctcaccac tgctcgtgag gctaagggca agatgccttc    13560
gcgccttctg gacatcaagt accgcaagcg ccagatcgat tcccgccgag ctcagattaa    13620
gcaatgggtc gagaacgagt atgctgagct ccgctacgag ctcgatgagc tcaaggccag    13680
caacagcctc accgtctcgg aagaagagta tcttgctgct gagactgagc gcattcagaa    13740
ggaagccaag cgtcagcacc gcgaggccct taacctgtgg ggcaatgagt tctacagaca    13800
ggaccctcag atcgctcctc tgcgtggtgc ccttgcctcc tttggcttga cgatcgatga    13860
cattggtgtt ggatccttcc acggtacctc caccaaggcc aacgacaaga acgaatccga    13920
agtcgtcaac aagcagctcg agcatttggg tcgcagcaag ggtaacgctt tgccctctat    13980
ctggcaaaag tacctcacgg gacatcccaa gggtgctgct gctgcctgga tgatgaacgg    14040
tgtcctgcaa gtcctccaga cgggtctcat tcccggaaac cgtaacgccg acaacattga    14100
cgacacaatg agacagtatg agcacgtctt gtacacctcg cggtcgattc agactgatgg    14160
tgtcaaggcc ggtctgctca aatcgttcgg tttcggccag gtcggaggtg aagttctcct    14220
gatccactcg gattacattc ttggtgcatt ggaggagcac gagtacgagg cttacaaggt    14280
caagcagcag gcgcgccagg ccaagtcgta ccggtacttg catgactcta tgaccggcgg    14340
ccctgccctg gtccaggtca agaacgctcc cccatactcg cccgagctcg agtccccgt    14400 gtacttgaac cccaaggccc gtgcgcagta caacaacgcg accaagtcct gggcgttcaa    14460
cgctaagcac ctggtaccccg agtctgacaa gattgatgtg gacatgacgc gtgcgattct    14520
ggagacgtcc gctcaagagt cattaggtgt gacgtcctcg tcttcgcgcg gtgtgggtgt    14580
ggatgtggaa atggtctctg cgatcaacat tgagaacgac acgttcttgg agcgtaactt    14640
tacccagcag gagattgact actgtctgag ccgaccggat cctcaggcta gctttgctgg    14700
tcggtggtct gccaaggagg ccgtggttaa ggccgtttcg tcgttctcgc tcgactctga    14760
gaaggtgtgg acacagggtg caggagcggg actgagtgag attgagattg tgatggcaga    14820
gagcggcgca ccctcggtgg tgttctcggg tgcggcccag gaggcggcgg ccaaggccgg    14880
cgtcaaggag atcaaggtct cgatcagcca ttctggcgcg tacgcggttg cggttgcaaa    14940
tgcgttgtaa aaacctcccc tctccttcaa gtgttcttgt tctttcattt tttctttcgt    15000
tcttttaatt gcgcttgctt gtgctttctt cagtagagtt ctcttttttc tttcttcatt    15060
ctatttcttt acttcttata ccttttcatg ggcccttgta tacaaacaac ttataaataa    15120
aaagggtgtt ctgcgggtgg ggtgggaggc gggccacgat gggtttcaag caggtatgat    15180
ggaagaaggc tctacattct caagagaaca gctggggagt gacaggttga gttgaacgca    15240
```

-continued

```
acgcttctct tcttgcctcc tttattttct agttctcccg agtcccttct tgactacttg   15300
gcttacgcaa caagtaccca gcgcgcctcc ttcaccttca cttacgagag caatatctct   15360
aaaaaaaaat aatgcttcta ttgtacttca aaatgcagtg cgatgattat gatgcttttg   15420
tggatgctcc gactatctac atccccaggg gtaggggttt catccctctc gatgcccttc   15480
cttctcgttc agccgtgcgt tggctcctga gcctcactgt ccagcgttcc tcgccgata   15539
```

<210> SEQ ID NO 3
<211> LENGTH: 4162
<212> TYPE: PRT
<213> ORGANISM: Mortierella alpina

<400> SEQUENCE: 3

```
Met Thr Thr Ala Gln Ser Asn Leu Thr Arg Pro Leu Ala Leu Lys Gln
1               5                   10                  15

Gly Thr Ser Glu Val Ser Ile Leu Val Pro Ser Asp Val Trp Val Ala
                20                  25                  30

Ala Glu Gln Leu Arg Glu Glu Phe Leu Ile Ser Val Glu Ala Ala Pro
            35                  40                  45

Ala Glu Glu Ala Ala Ala Thr Gly Ser Ala Asp Asp Gln Ala Pro Glu
        50                  55                  60

Met Ala Leu Val Ala Arg Phe Leu Lys Phe Ala Thr Asp Lys Ser Glu
65                  70                  75                  80

Gln Ser Asp Pro Ser Leu Gln Phe Ile Pro Val Leu Arg Thr Val Phe
                85                  90                  95

Leu Phe Phe Val Thr Lys Tyr Leu Lys Gly Asn Asp Ile His Ala Val
                100                 105                 110

Thr Arg Leu Leu Ala Lys Asp Thr Arg Val Val Ile Ile Asn Ala Phe
            115                 120                 125

Phe Ser Ala Leu Val Phe Leu Arg Ala Thr Glu Ala Leu Ala Pro Glu
130                 135                 140

Asp Tyr Thr Pro Pro Thr Ser Ala Leu Phe Ala Ala Gln Glu Gly
145                 150                 155                 160

Lys Ala Lys Leu Phe Ala Ile Phe Gly Gly Gln Gly Asn Ile Glu Glu
                165                 170                 175

Tyr Phe Asp Glu Leu Ala Asp Ile Tyr Thr Thr Tyr Thr Thr Leu Val
            180                 185                 190

Gln Asp Tyr Val Glu Asp Met Ala Ala Val Leu Arg Glu His Ala Arg
        195                 200                 205

Ser Asp Asp Ala Ser Val Phe His Ser Lys Gly Leu Asp Val Met Gly
    210                 215                 220

Trp Leu Arg Ser Pro Asp Ser Lys Pro Asp Val Ala Tyr Leu Val Ser
225                 230                 235                 240

Ala Pro Val Ser Leu Pro Leu Ile Gly Leu Val Gln Leu Met His Tyr
                245                 250                 255

Tyr Val Met Leu Lys Val Leu Asp Gln Thr Pro Ala Gln Leu Arg Asp
            260                 265                 270

Val Ile Leu Gly Ser Thr Gly His Ser Gln Gly Ile Ile Ser Ser Val
        275                 280                 285

Val Ile Ser Ser Ser Ala Thr Phe Glu Glu Phe Phe Ala Asn Ser Arg
    290                 295                 300

Lys Ala Leu Gly Leu Leu Phe Trp Ile Gly Thr Arg Ser Gln Glu Val
305                 310                 315                 320

Tyr Pro Gln Thr Thr Leu Asn Pro Ala Ile Leu Gln Asp Ser Leu Ser
                325                 330                 335
```

```
Asn Asn Glu Gly Asn Pro Thr Pro Met Leu Val Val Asn Ser Leu Arg
            340                 345                 350

Ala Ser Glu Val Gln Lys Tyr Val Glu Ala Thr Asn Arg His Leu Pro
        355                 360                 365

Glu Asp Arg Lys Ile Lys Ile Ala Leu Ile Asn Gly Pro Arg Ser Ser
    370                 375                 380

Ile Cys Thr Gly Pro Pro Gln Ser Leu Tyr Gly Leu Asn Leu Ala Leu
385                 390                 395                 400

Arg Lys Leu Lys Ala Pro Thr Gly Leu Glu Gln Gly Arg Val Pro Phe
                405                 410                 415

Ser Gln Arg Lys Val Lys Phe Ser Ser Arg Phe Leu Pro Ile Thr Ala
                420                 425                 430

Pro Phe His Ser Ser Tyr Leu Asp Gly Val Ser Ala Leu Val Glu Ser
            435                 440                 445

Asp Ile Ala Arg Tyr Asp Leu Arg Phe Asp His Thr Gln Met Thr Ile
        450                 455                 460

Pro Val Phe Ser Thr Asp Ser Gly Lys Asp Ile Ala Gly Ser Pro Thr
465                 470                 475                 480

Ile Thr Thr Asp Leu Val Asn Gln Ile Cys Ser Leu Pro Val His Trp
                485                 490                 495

Glu Lys Ala Thr Ala Met Ala Gly Leu Thr His Val Ile Asp Phe Gly
                500                 505                 510

Pro Gly Gly Ser Ser Gly Val Gly Ser Leu Thr Ala Arg Asn Lys Asp
            515                 520                 525

Gly Thr Gly Val Gln Val Met Leu Ala Gly Ala Ser Glu Gly Val Asn
    530                 535                 540

Arg Glu Leu Ser Tyr Lys Pro Asp Ile Phe Asp Ala Asn Pro Ala Ala
545                 550                 555                 560

Leu Arg Tyr Ala Pro Asn Trp Ala Asn Glu Phe Gln Pro Lys Leu Val
                565                 570                 575

Arg Ser Val Asn Gly Glu Ile His Ile Asp Thr Arg Met Ser Arg Leu
            580                 585                 590

Leu Ser Lys Pro Pro Leu Met Val Ala Gly Met Thr Pro Ser Thr Val
        595                 600                 605

Asn Glu Gly Phe Val Ser Ala Val Met Asn Ala Gly Tyr His Val Glu
    610                 615                 620

Leu Ala Gly Gly Gly His Tyr Asn Glu Ala Ala Val Arg Ser Lys Val
625                 630                 635                 640

Lys Lys Ile Met Gln Leu Thr Thr Pro Gly Ala Gly Ile Thr Leu Asn
                645                 650                 655

Thr Leu Phe Ile Asn Val Arg Gln Trp Gly Phe Gln Ala Pro Leu Val
            660                 665                 670

Pro Lys Leu Arg Arg Glu Gly Leu Pro Met Glu Gly Phe Cys Cys Ala
        675                 680                 685

Ala Gly Val Pro Ser Leu Glu Val Ala Asp Glu Phe Ile Thr Asp Met
    690                 695                 700

Leu Ser Ala Gly Ile Arg His Ile Ser Phe Lys Pro Gly Ser Ala Glu
705                 710                 715                 720

Ala Ile Arg Gln Val Leu Ala Ile Ala Asn Ala His Pro Glu Met Pro
                725                 730                 735

Ile Val Leu Gln Trp Thr Gly Gly Arg Ala Gly Gly His His Ser Phe
            740                 745                 750

Glu Asp Phe His Gln Pro Ile Leu Glu Thr Tyr Ser Ala Ile Arg Arg
```

```
                755              760            765
His Pro Asn Val Val Leu Val Ala Gly Ser Gly Phe Gly Gly Ala Glu
    770             775             780

Asp Thr Tyr Pro Tyr Leu Thr Gly Asp Trp Ser Val Gln Leu Asp Tyr
785             790             795             800

Pro Pro Met Pro Phe Asp Gly Met Leu Phe Gly Ser Arg Val Met Val
            805             810             815

Ala Lys Glu Gly Met Ala Ser Leu Gly Val Lys Gln Ala Ile Val Asp
        820             825             830

Ala Pro Gly Val Glu Asp Ser Glu Trp Glu Lys Thr Tyr Lys Gly Pro
    835             840             845

Thr Gly Gly Val Met Thr Val Arg Ser Glu Leu Gly Glu Pro Ile His
850             855             860

Lys Ile Ala Thr Arg Gly Val Lys Leu Trp Lys Glu Met Asp Asp Thr
865             870             875             880

Ile Phe Ala Leu Pro Lys Asp Lys Arg Pro Ala Ala Leu Leu Ala Lys
            885             890             895

Lys Asp Tyr Ile Ile Lys Arg Leu Asn Ala Asp Phe Gln Lys Val Trp
        900             905             910

Phe Gly Lys Lys Ala Asn Gly Ser Val Ala Asp Leu Gln Asp Met Thr
    915             920             925

Tyr Glu Glu Val Ile Asn Arg Leu Ile Glu Leu Met Phe Ile Lys His
930             935             940

Glu Glu Arg Trp Ile Asp His Ser His Arg Asn Leu Leu Gly Asp Ile
945             950             955             960

Leu Arg Arg Ile Glu Glu Arg Phe Val Gly Val Glu Lys Lys Ser Ile
            965             970             975

Val Gln Thr Phe Ser Gln Leu Asp Ile Pro Phe Ala Phe Ala Gln Glu
        980             985             990

Phe Val Asp Thr Tyr Pro Leu Thr Lys Thr Gln Leu Leu Thr Thr Glu
    995             1000            1005

Asp Val Gly Tyr Phe Leu Phe Leu Met Asn Arg Arg Gly Gln Lys
    1010            1015            1020

Pro Val Pro Phe Ile Pro Val Leu Asp Lys Asp Phe Glu Val Trp
    1025            1030            1035

Phe Lys Lys Asp Ser Leu Trp Gln Ala Glu Asp Leu Ala Ala Val
    1040            1045            1050

Val Asp Gln Asp Val Gln Arg Thr Cys Ile Leu Gln Gly Pro Ala
    1055            1060            1065

Ala Val Arg Tyr Ala Thr Lys Val Asp Glu Pro Val Lys Asp Ile
    1070            1075            1080

Leu Asp Gly Ile Phe His Ser His Ile Ala Trp Leu Lys Glu Arg
    1085            1090            1095

Tyr Tyr Asn Asn Asn Asp Ala Asn Ile Pro Gln Val Glu Tyr Phe
    1100            1105            1110

Gly Gly Lys Pro Gly Arg Phe Glu Ser Ala Leu Asp Ala Val Leu
    1115            1120            1125

Pro Leu Val Lys Val Glu Thr Tyr Asp Asn Gly Lys Val Lys Met
    1130            1135            1140

Val Glu Thr Ser Met Leu Glu Ser Ser Leu Pro Lys Asn Glu Asp
    1145            1150            1155

Trp Leu Glu Tyr Leu Ala Gly Gln Asp Pro Ser Trp Phe Arg Ala
    1160            1165            1170
```

-continued

```
Leu Leu Thr Ala Pro Ala Val Ile Gln Gly Lys Lys Phe Leu Asp
    1175            1180                1185

Asn Pro Leu Ala Arg Ile Phe Arg Pro Arg Val Ser Gln Ala Val
    1190            1195                1200

His Phe Glu Tyr Ala Glu Asp Lys Leu Gln Thr Ile Thr Val Tyr
    1205            1210                1215

Asp Arg Arg Ser Trp Ser Ala Ser Ser Lys Ser Ser Glu Leu Ser
    1220            1225                1230

Pro Ser Leu Arg Ala Arg Leu Gln Pro Asn Glu Leu Ile Glu Val
    1235            1240                1245

Val Leu Val Glu Lys Asn Gly Glu Arg Leu Ile Pro Phe Pro Leu
    1250            1255                1260

Leu Phe His Tyr Thr Pro Glu Lys Gly Tyr Ala Pro Ile His Glu
    1265            1270                1275

Val Met Glu Gly Arg Asn Glu Arg Ile Lys Glu Phe Tyr Tyr Lys
    1280            1285                1290

Leu Trp Phe Pro Ser Glu Glu Asp Gln Phe Asn Ala Cys Leu Ala
    1295            1300                1305

Thr Asp Ala Phe Thr Glu Lys Phe Ile Cys Asn Gly Glu Gln Val
    1310            1315                1320

Ser Thr Pro Glu Ile Lys Glu Phe Cys Gln Ala Val Gly Asn Gln
    1325            1330                1335

Ala Glu Leu Tyr Val Glu Arg Arg Gln Lys Val Val Tyr Ala Pro
    1340            1345                1350

Met Asp Phe Ala Ile Val Val Gly Trp Lys Ser Ile Ile Lys Ala
    1355            1360                1365

Ile Phe Pro Lys Ser Ile Asp Gly Asp Leu Leu Lys Leu Val His
    1370            1375                1380

Leu Ser Asn Gly Phe Arg Met Leu Asp Gly Ala Glu Ser Leu Lys
    1385            1390                1395

Gln Gly Asp Ile Val Asp Thr Val Ala Glu Ile Asn Ala Val Val
    1400            1405                1410

Asn Asn Asp Ser Gly Lys Leu Val Gln Val Lys Gly Val Val Leu
    1415            1420                1425

Arg Glu Gly Lys Arg Val Met Glu Val Thr Ser Glu Phe Leu Tyr
    1430            1435                1440

Arg Gly Thr Phe Val Asp Tyr Gln Asn Thr Phe Gln Lys Thr Val
    1445            1450                1455

Glu Thr Pro Met Glu Val Lys Leu Thr Ser Ala Lys Asp Val Ala
    1460            1465                1470

Val Leu Lys Ser Lys Glu Trp Ile Gln Trp Ala Glu Gly Glu His
    1475            1480                1485

Thr Val Gly Pro Asn Ala Ser Leu Val Phe Arg Leu Asn Thr Ile
    1490            1495                1500

Val Arg Phe Lys Asn Lys Thr Thr Phe Ser His Val Glu Thr Thr
    1505            1510                1515

Gly Thr Val Ser Met Gln Ile Ser Thr Lys Glu His Val Glu Ile
    1520            1525                1530

Ala Thr His Tyr Ser Asn Asp Glu Glu Thr Gln Gly Asn Pro
    1535            1540                1545

Val Leu Ala Tyr Leu Lys Arg Ser Gly Ser Pro Ile Glu Gln Ala
    1550            1555                1560

Ile His Phe Glu Asn Gly Gly Tyr Ser Val Met Pro Glu Gly Ser
    1565            1570                1575
```

-continued

Phe Ser Ser Glu Val Ile Ser Pro Phe Ser Asn Glu Pro Tyr Ala
        1580                1585                1590

Lys Val Ser Gly Asp Phe Asn Pro Ile His Val Asn Pro Tyr Phe
    1595                1600                1605

Ala Asp Leu Ala Glu Leu Pro Gly Thr Ile Thr His Gly Met Trp
1610                1615                1620

Thr Ser Ala Ser Thr Arg Lys Phe Val Glu Ile Phe Ala Ala Glu
    1625                1630                1635

Asn His Pro Gln Arg Val Thr Ser Tyr Glu Val Lys Phe Leu Ser
    1640                1645                1650

Met Val Leu Pro Gln Asp Arg Leu Ser Thr Lys Leu Ser His Ile
1655                1660                1665

Gly Met Ile Asn Gly Lys Lys Ile Ile Lys Val Glu Thr Phe Asn
1670                1675                1680

Gln Asn Gly Ser Lys Val Val Glu Gly Thr Ala Glu Ile Asp Gln
    1685                1690                1695

Pro Thr Ile Ala Tyr Val Phe Thr Gly Gln Gly Ser Gln Glu Gln
1700                1705                1710

Gly Met Gly Met Ala Leu Tyr Asp Ser Ser Pro Val Ala Lys Asp
1715                1720                1725

Ile Trp Gln Arg Ala Asp Arg His Phe Leu Glu Asn Tyr Gly Phe
1730                1735                1740

Ser Ile Leu Asp Ile Val Arg Asn Asn Pro Leu Lys Lys Thr Ile
    1745                1750                1755

His Phe Gly Gly Pro Lys Gly Asn Ala Ile Arg Gln Asn Tyr Met
    1760                1765                1770

Ser Met Arg Tyr Asp Gln Val Asp Gln Asp Gly Ser Ile Lys Ser
    1775                1780                1785

Leu Pro Leu Phe Pro Gly Ile Asn Glu Thr Thr His Phe Tyr Thr
    1790                1795                1800

Phe Gln Ser Pro Asn Gly Leu Leu Ala Ala Thr Gln Phe Thr Gln
1805                1810                1815

Pro Ala Leu Thr Leu Met Glu Lys Ala Ala Phe Glu Asp Met Arg
1820                1825                1830

Ser Lys Gly Leu Ile Gln Gly Asn Cys Ala Phe Ala Gly His Ser
    1835                1840                1845

Leu Gly Glu Tyr Ser Ala Leu Ala Ala Ile Gly Glu Val Leu Pro
1850                1855                1860

Ile Glu Ser Leu Val Asp Val Val Phe Tyr Arg Gly Met Thr Met
1865                1870                1875

Gln Val Ala Val Pro Arg Asp Ser Val Gly Arg Ser Asn Tyr Gly
    1880                1885                1890

Met Val Ala Ile Asn Pro Ser Arg Val Ser Pro Thr Phe Asn Asp
1895                1900                1905

Ser Ala Leu Arg Tyr Val Val Asp Ala Ile Ala Arg Gln Ser Asn
    1910                1915                1920

Gly Leu Leu Glu Ile Val Asn Glu Asn Val Glu Asn Trp Gln Tyr
1925                1930                1935

Val Ala Ala Gly Glu Leu Ser Asn Leu Asp Ala Leu Ser Thr Val
    1940                1945                1950

Leu Asn Tyr Leu Lys Val Gln Lys Ile Asp Leu Gln Lys Leu Met
    1955                1960                1965

Glu Thr Met Pro Leu Glu Glu Val Lys Lys His Leu Ser Gln Ile

-continued

```
                1970                1975                1980
Ile Ala Gly Ala Leu Glu Lys Val Ala Glu Lys Val Ala Lys Asp
1985                1990                1995

Gly His Ile Lys Pro Glu Arg Gly Val Ala Thr Ile Pro Leu Ala
2000                2005                2010

Gly Ile Asp Val Pro Phe His Ser Ser Phe Leu Leu Ser Gly Val
2015                2020                2025

Ala Pro Phe Arg Thr Tyr Leu Ala Lys Lys Ile Asn Pro Thr Phe
2030                2035                2040

Ile Asn Val Pro Leu Leu Thr Ser Lys Tyr Ile Pro Asn Leu Thr
2045                2050                2055

Ala Gln Pro Phe Ser Ile Glu Lys Ser Tyr Ile Glu Gly Val Tyr
2060                2065                2070

Asn Leu Thr Ser Ser Pro Arg Leu Ala Lys Val Leu Lys Asn Trp
2075                2080                2085

Ile Asp Thr Lys Leu Thr Ala Lys Gln Gln Gln Arg Leu Gly Tyr
2090                2095                2100

Thr Leu Leu Val Glu Leu Leu Ala Tyr Gln Phe Ala Ser Pro Val
2105                2110                2115

Arg Trp Ile Glu Thr Gln Asp Arg Leu Phe Lys Glu Tyr Asn Val
2120                2125                2130

Val Arg Leu Ile Glu Val Gly Pro Ser Pro Thr Leu Cys Gly Met
2135                2140                2145

Ala Gln Arg Thr Leu Lys Phe Lys Tyr Glu Ala Tyr Asp Asp Ala
2150                2155                2160

Leu Thr Phe Gln Arg Ser Thr Leu Cys Thr Ser Lys Asp Ser Lys
2165                2170                2175

Glu Ile Tyr Tyr Ala Met Asp Asn Val Glu Ser Ser Ala Pro Ala
2180                2185                2190

Pro Ala Ala Ser Ala Ala Ala Pro Ala Pro Lys Ala Thr Pro Val
2195                2200                2205

Ala Ala Ala Ala Pro Ala Pro Val Ala Val Ala Ala Ala Gly Pro
2210                2215                2220

Ala Ala Ala Val Ser Asp Val Pro Ile Lys Ala Leu Glu Ile Leu
2225                2230                2235

His Val Ile Val Ala Gln Lys Val Lys Lys Thr Leu Glu Glu Val
2240                2245                2250

Pro Leu Ser Lys Ala Ile Lys Asp Leu Val Gly Gly Lys Ser Thr
2255                2260                2265

Leu Gln Asn Glu Ile Leu Gly Asp Leu Gln Lys Glu Phe Gly Ser
2270                2275                2280

Ser Gly Phe Pro Glu Lys Gly Glu Glu Ala Pro Leu Glu Glu Leu
2285                2290                2295

Ala Asn Ala Leu Gln Gly Asn Phe Asn Gly Ala Leu Gly Lys Gln
2300                2305                2310

Thr Thr Ser Leu Ile Ala Lys Met Ile Gly Ser Lys Met Pro Gly
2315                2320                2325

Gly Tyr Ser Leu Ser Thr Ala Lys Gly Tyr Leu Ala Lys Ala His
2330                2335                2340

Gly Leu Gly Pro Val Arg Ala Asp Ala Ala Leu Leu Val Gly Leu
2345                2350                2355

Thr Met Glu Pro Ala Ala Arg Leu Gly Ala Val Pro Glu Ala Asn
2360                2365                2370
```

-continued

```
Ala Trp Leu Asp Ser Val Ala Gln Ala Tyr Ala Arg Arg Ala Gly
2375                2380                2385

Ile Ser Leu Ser Ala Gly Ala Pro Ala Gly Gly Ala Ala Pro Val
2390                2395                2400

Met Met Ala Ala Ala Gly Pro Ala Ala Ala Gly Pro Ala Ala Ala
2405                2410                2415

Val Ala Asp Ala Pro Ile Lys Ala Ile Asp Ile Leu His Val Ile
2420                2425                2430

Val Ala Gln Lys Ile Lys Lys Thr Val Glu Glu Val Pro Leu Ser
2435                2440                2445

Lys Ala Ile Lys Asp Leu Val Gly Gly Lys Ser Thr Leu Gln Asn
2450                2455                2460

Glu Ile Leu Gly Asp Leu Gln Lys Glu Phe Gly Ser Ser Gly Phe
2465                2470                2475

Pro Glu Lys Gly Glu Glu Ala Pro Leu Glu Asp Leu Gly Asn Ala
2480                2485                2490

Leu Gln Gly Asn Phe Gly Gly Ser Leu Gly Met Gln Thr Thr Ser
2495                2500                2505

Leu Ile Ala Lys Met Met Gly Ser Lys Met Pro Gly Gly Phe Thr
2510                2515                2520

Gln Ser Ser Ala Lys Ala Tyr Leu Ala Ser Ser Tyr Gly Leu Gly
2525                2530                2535

Pro Leu Arg Ala Asp Gly Ala Leu Leu Leu Gly Val Thr Met Glu
2540                2545                2550

Pro Ser Ala Arg Leu Gly Ser Glu Gly Asp Ala Lys Ala Trp Leu
2555                2560                2565

Asp Thr Val Ala Gln Ala Tyr Ala Arg Arg Ala Gly Ile Ser Leu
2570                2575                2580

Gly Gly Gly Gly Gly Gly Ala Val Ala Gly Gly Ala Val Gly Gly
2585                2590                2595

Ala Met Met Asn Ser Glu Glu Phe Asn Gln Phe Gln Ala Lys Gln
2600                2605                2610

Asn Ala Met Met Tyr Gln His Leu Glu Ile Tyr Ala Arg Tyr Leu
2615                2620                2625

Glu Lys Asp Leu Arg Ala Gly Glu Lys Gln Tyr Glu Glu Glu Lys
2630                2635                2640

Leu Ala Thr Leu Arg Leu Gln Ala Asp Ile Asp Gln Trp Met Ala
2645                2650                2655

Glu His Gly Asp Tyr Tyr Ala Glu Gly Ile Lys Pro Ala Phe Ser
2660                2665                2670

Ala Lys Lys Ala Arg Lys Tyr Asp Ser His Trp Asn Trp Val Arg
2675                2680                2685

Gln Asp Ala Met Ser Leu Leu Tyr Asp Met Ile Phe Gly Arg Leu
2690                2695                2700

Thr Val Val Asp Arg Glu Val Val Ala Gln Cys Ile His Val Met
2705                2710                2715

Asn Arg Ala Asn Pro Gln Leu Leu Glu Phe Met Ile Tyr His Ile
2720                2725                2730

Asp Asn Thr Ala Ala Asp Arg Gly Lys Thr Tyr Ala Leu Ala Lys
2735                2740                2745

Glu Phe Gly Asn Met Leu Ile Glu Asn Cys Arg Glu Val Leu Glu
2750                2755                2760

Ala Ala Pro Val Tyr Lys Asp Val Gly Val Pro Thr Gly Pro Gln
2765                2770                2775
```

-continued

```
Thr Thr Ile Asp Asn Lys Gly Asn Ile Leu Tyr Glu Glu Val Gln
        2780            2785            2790

Arg Val Gly Val Arg Lys Leu Asp His Tyr Val Lys Asp Met Val
    2795            2800            2805

Ala Gly Gly Lys Met Ser Glu Tyr Ser Asn Arg Gln Lys Val Gln
    2810            2815            2820

Lys Asn Leu Ala Gln Ile Tyr Lys Ile Ile Lys Ala Gln Asn Thr
    2825            2830            2835

Met Lys Ser Ser Ser Lys Leu Ala Ile Lys Ser Leu Tyr Gly Glu
    2840            2845            2850

Val Ile His Ala Met Asn Met Ser Asn Thr Ile Ile Arg Glu Glu
    2855            2860            2865

Lys Asn Arg Arg Ala Ser Arg Val Arg Arg Ala Ser Ala Val Pro
    2870            2875            2880

Ser Ala Asp Arg Pro Lys Lys Glu Ala Lys Lys Glu Thr Ile Pro
    2885            2890            2895

Phe Leu His Leu Lys Lys Lys Asn Pro Gln Ser Glu Ser Gly Trp
    2900            2905            2910

Glu Phe Ser Gln Arg Leu Thr Ser Val Tyr Leu Asp Val Leu Thr
    2915            2920            2925

Asn Ile Ala Arg Asp Gly Val Thr Phe Glu Asn Arg Met Val Leu
    2930            2935            2940

Met Thr Gly Ala Gly Lys Asp Ser Ile Gly Ala Ser Ile Leu Lys
    2945            2950            2955

Gly Leu Leu Ser Gly Gly Ala Lys Val Val Thr Thr Ser Arg
    2960            2965            2970

Phe Ser Arg Asp Val Thr Glu Tyr Tyr Gln Ser Ile Tyr Gln Arg
    2975            2980            2985

His Gly Ser Lys Asn Ser Cys Leu Val Val Val Pro Phe Asn Gly
    2990            2995            3000

Gly Ser Lys Gln Asp Val Asp Ala Leu Val Asn Tyr Ile Tyr Asp
    3005            3010            3015

Lys Asp Leu Lys Lys Gly Leu Gly Trp Asp Leu Asp Tyr Ile Ile
    3020            3025            3030

Pro Phe Ala Ala Ile Ser Val Gln Gly Lys Glu Ile Asp Asn Ile
    3035            3040            3045

Asp Ser Gln Ser Glu Leu Ala His Arg Ile Met Leu Thr Asn Val
    3050            3055            3060

Leu Arg Leu Leu Gly Asn Val Lys Ala Lys Lys Met Glu His Gly
    3065            3070            3075

Tyr Asp Thr Arg Pro Ala Gln Val Ile Leu Pro Leu Ser Pro Asn
    3080            3085            3090

His Gly Thr Phe Gly Ala Asp Gly Leu Tyr Gly Glu Ser Lys Val
    3095            3100            3105

Ala Leu Glu Thr Leu Phe Asn Arg Trp Ser Ser Glu Ser Trp Gly
    3110            3115            3120

Ala Tyr Leu Thr Ile Thr Gly Ala Val Ile Gly Trp Thr Arg Gly
    3125            3130            3135

Thr Gly Leu Met Ser Gly Asn Asn Ile Val Ala Glu Gly Leu Glu
    3140            3145            3150

Lys Tyr Gly Val Arg Thr Phe Ser Gly Gln Glu Met Ala Phe Asn
    3155            3160            3165

Ile Leu Gly Leu Met His Pro Ser Ile Thr Asn Leu Cys Gln Val
```

```
                3170                3175                3180

Glu Pro Val Trp Ala Asp Leu Asn Gly Gly Leu Gln Tyr Leu Pro
    3185                3190                3195

Asn Leu Asn Glu Ile Ser Ala Asn Leu Arg Ala Glu Tyr Arg Gln
    3200                3205                3210

Thr Ala Glu Ile Arg Lys Ala Ile Val Thr Glu Asn Thr Leu Asp
    3215                3220                3225

Phe Lys Glu Thr His Gly Ala Glu Ala Glu Arg Lys His Gln Pro
    3230                3235                3240

His Lys Val Thr Pro Arg Ala Asn Met Lys Phe Pro Phe Pro Glu
    3245                3250                3255

Leu Lys Asp Tyr Lys Asp Leu Ser His Ala His Lys Leu Arg Gly
    3260                3265                3270

Met Leu Asp Leu Glu Lys Val Val Val Thr Gly Phe Ser Glu
    3275                3280                3285

Val Gly Pro Trp Gly Asn Ser Arg Thr Arg Trp Glu Met Glu Ala
    3290                3295                3300

Asn Gly Gln Phe Ser Leu Glu Gly Cys Ile Glu Met Ala Trp Ile
    3305                3310                3315

Met Gly Phe Ile Lys His His Asn Gly Asn Leu Lys Ser Gly Ser
    3320                3325                3330

Pro Tyr Ser Gly Trp Val Asp Ala Lys Thr Glu Glu Pro Val Lys
    3335                3340                3345

Asp Arg Asp Val Lys Ala Lys Tyr Glu Lys Gln Ile Leu Glu His
    3350                3355                3360

Thr Gly Ile Arg Leu Ile Glu Pro Glu Leu Phe Gly Gly Tyr Asp
    3365                3370                3375

Pro Lys Arg Lys Gly Leu Leu Gln Glu Val Leu Ile Asp His Asp
    3380                3385                3390

Leu Glu Ala Phe Glu Val Ser Lys Glu Glu Ala Gln Met Phe Lys
    3395                3400                3405

Leu Glu His Gly Asp Lys Val Asp Ile Tyr Glu Glu Glu Ser Gly
    3410                3415                3420

Gln Trp Ala Val Lys Phe Lys Lys Gly Ala Asn Met Tyr Ile Pro
    3425                3430                3435

Lys Ala Leu Lys Phe Asp Arg Leu Val Ala Gly Gln Ile Pro Thr
    3440                3445                3450

Gly Trp Asp Ala Ala Arg Phe Gly Val Pro Lys Asp Ile Ile Asp
    3455                3460                3465

Gln Val Asp Thr Ile Thr Leu Tyr Val Leu Val Ser Thr Val Glu
    3470                3475                3480

Ala Leu Val Ala Ser Gly Ile Thr Asp Pro Tyr Glu Phe Tyr Gln
    3485                3490                3495

Tyr Val His Val Ser Glu Val Gly Asn Thr Ala Gly Ser Gly Val
    3500                3505                3510

Gly Gly Met Leu Ser Leu Arg Gly Met Tyr Arg Gly Arg Val Met
    3515                3520                3525

Asp Asp Pro Val Gln Lys Asp Ile Leu Gln Glu Ser Phe Ile Asn
    3530                3535                3540

Thr Met Pro Ala Trp Val Asn Met Leu Leu Leu Ser Ser Ser Gly
    3545                3550                3555

Pro Ile Lys Thr Pro Val Gly Ala Cys Ala Thr Ala Val Glu Ser
    3560                3565                3570
```

-continued

| | | | | | | | | | | |
|---|---|---|---|---|---|---|---|---|---|---|
| Val | Glu | Ile | Gly | Val | Asp | Thr | Ile | Gln | Ser | Gly | Lys | Ala | Lys | Ile |
| 3575 | | | | | 3580 | | | | | 3585 | | | | |
| Val | Ile | Val | Gly | Gly | Tyr | Asp | Asp | Phe | Gln | Glu | Glu | Gly | Ser | Tyr |
| 3590 | | | | | 3595 | | | | | 3600 | | | | |
| Glu | Phe | Ala | Asn | Met | Lys | Ala | Thr | Ser | Asn | Thr | Glu | Glu | Glu | Phe |
| 3605 | | | | | 3610 | | | | | 3615 | | | | |
| Ala | His | Gly | Arg | Thr | Pro | Lys | Glu | Met | Ser | Arg | Pro | Ala | Thr | Ser |
| 3620 | | | | | 3625 | | | | | 3630 | | | | |
| Thr | Arg | Ser | Gly | Phe | Met | Glu | Ser | His | Gly | Ala | Gly | Ile | Glu | Ile |
| 3635 | | | | | 3640 | | | | | 3645 | | | | |
| Leu | Met | Gln | Ala | Lys | Leu | Ala | Val | Glu | Met | Gly | Val | Pro | Ile | Tyr |
| 3650 | | | | | 3655 | | | | | 3660 | | | | |
| Gly | Ile | Val | Gly | Leu | Thr | Asn | Thr | Ala | Thr | Asp | Lys | Glu | Gly | Arg |
| 3665 | | | | | 3670 | | | | | 3675 | | | | |
| Ser | Val | Pro | Ala | Pro | Gly | Gln | Gly | Val | Leu | Thr | Thr | Ala | Arg | Glu |
| 3680 | | | | | 3685 | | | | | 3690 | | | | |
| Ala | Lys | Gly | Lys | Met | Pro | Ser | Arg | Leu | Leu | Asp | Ile | Lys | Tyr | Arg |
| 3695 | | | | | 3700 | | | | | 3705 | | | | |
| Lys | Arg | Gln | Ile | Asp | Ser | Arg | Arg | Ala | Gln | Ile | Lys | Gln | Trp | Val |
| 3710 | | | | | 3715 | | | | | 3720 | | | | |
| Glu | Asn | Glu | Tyr | Ala | Glu | Leu | Arg | Tyr | Glu | Leu | Asp | Glu | Leu | Lys |
| 3725 | | | | | 3730 | | | | | 3735 | | | | |
| Ala | Ser | Asn | Ser | Leu | Thr | Val | Ser | Glu | Glu | Tyr | Leu | Ala | Ala |
| 3740 | | | | | 3745 | | | | | 3750 | | | | |
| Glu | Thr | Glu | Arg | Ile | Gln | Lys | Glu | Ala | Lys | Arg | Gln | His | Arg | Glu |
| 3755 | | | | | 3760 | | | | | 3765 | | | | |
| Ala | Leu | Asn | Leu | Trp | Gly | Asn | Glu | Phe | Tyr | Arg | Gln | Asp | Pro | Gln |
| 3770 | | | | | 3775 | | | | | 3780 | | | | |
| Ile | Ala | Pro | Leu | Arg | Gly | Ala | Leu | Ala | Ser | Phe | Gly | Leu | Thr | Ile |
| 3785 | | | | | 3790 | | | | | 3795 | | | | |
| Asp | Asp | Ile | Gly | Val | Gly | Ser | Phe | His | Gly | Thr | Ser | Thr | Lys | Ala |
| 3800 | | | | | 3805 | | | | | 3810 | | | | |
| Asn | Asp | Lys | Asn | Glu | Ser | Glu | Val | Val | Asn | Lys | Gln | Leu | Glu | His |
| 3815 | | | | | 3820 | | | | | 3825 | | | | |
| Leu | Gly | Arg | Ser | Lys | Gly | Asn | Ala | Leu | Pro | Ser | Ile | Trp | Gln | Lys |
| 3830 | | | | | 3835 | | | | | 3840 | | | | |
| Tyr | Leu | Thr | Gly | His | Pro | Lys | Gly | Ala | Ala | Ala | Trp | Met | Met |
| 3845 | | | | | 3850 | | | | | 3855 | | | | |
| Asn | Gly | Val | Leu | Gln | Val | Leu | Gln | Thr | Gly | Leu | Ile | Pro | Gly | Asn |
| 3860 | | | | | 3865 | | | | | 3870 | | | | |
| Arg | Asn | Ala | Asp | Asn | Ile | Asp | Asp | Thr | Met | Arg | Gln | Tyr | Glu | His |
| 3875 | | | | | 3880 | | | | | 3885 | | | | |
| Val | Leu | Tyr | Thr | Ser | Arg | Ser | Ile | Gln | Thr | Asp | Gly | Val | Lys | Ala |
| 3890 | | | | | 3895 | | | | | 3900 | | | | |
| Gly | Leu | Leu | Lys | Ser | Phe | Gly | Phe | Gly | Gln | Val | Gly | Gly | Glu | Val |
| 3905 | | | | | 3910 | | | | | 3915 | | | | |
| Leu | Leu | Ile | His | Ser | Asp | Tyr | Ile | Leu | Gly | Ala | Leu | Glu | Glu | His |
| 3920 | | | | | 3925 | | | | | 3930 | | | | |
| Glu | Tyr | Glu | Ala | Tyr | Lys | Val | Lys | Gln | Gln | Ala | Arg | Gln | Ala | Lys |
| 3935 | | | | | 3940 | | | | | 3945 | | | | |
| Ser | Tyr | Arg | Tyr | Leu | His | Asp | Ser | Met | Thr | Gly | Gly | Pro | Ala | Leu |
| 3950 | | | | | 3955 | | | | | 3960 | | | | |
| Val | Gln | Val | Lys | Asn | Ala | Pro | Pro | Tyr | Ser | Pro | Glu | Leu | Glu | Ser |
| 3965 | | | | | 3970 | | | | | 3975 | | | | |

```
Pro Val Tyr Leu Asn Pro Lys Ala Arg Ala Gln Tyr Asn Asn Ala
    3980            3985                3990

Thr Lys Ser Trp Ala Phe Asn Ala Lys His Leu Val Pro Glu Ser
    3995            4000                4005

Asp Lys Ile Asp Val Asp Met Thr Arg Ala Ile Leu Glu Thr Ser
    4010            4015                4020

Ala Gln Glu Ser Leu Gly Val Thr Ser Ser Ser Arg Gly Val
    4025            4030                4035

Gly Val Asp Val Glu Met Val Ser Ala Ile Asn Ile Glu Asn Asp
    4040            4045                4050

Thr Phe Leu Glu Arg Asn Phe Thr Gln Gln Glu Ile Asp Tyr Cys
    4055            4060                4065

Leu Ser Arg Pro Asp Pro Gln Ala Ser Phe Ala Gly Arg Trp Ser
    4070            4075                4080

Ala Lys Glu Ala Val Val Lys Ala Val Ser Ser Phe Ser Leu Asp
    4085            4090                4095

Ser Glu Lys Val Trp Thr Gln Gly Ala Gly Ala Gly Leu Ser Glu
    4100            4105                4110

Ile Glu Ile Val Met Ala Glu Ser Gly Ala Pro Ser Val Val Phe
    4115            4120                4125

Ser Gly Ala Ala Gln Glu Ala Ala Ala Lys Ala Gly Val Lys Glu
    4130            4135                4140

Ile Lys Val Ser Ile Ser His Ser Gly Ala Tyr Ala Val Ala Val
    4145            4150                4155

Ala Asn Ala Leu
    4160

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gly Ser Gln Glu Gln Gly Met Gly Met
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Thr Gln Phe Arg Gln Pro Ala Leu Thr
1               5                   10

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, g, t, unknown or other
```

```
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other

<400> SEQUENCE: 6
carggnwsnc argarcargg natgggnatg                                    30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other

<400> SEQUENCE: 7
gtnarngcng gytgngtraa ytgngtngc                                     29

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctctgtatg actcttcccc c                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccaaaagac cgttgggtga c                                             21
```

```
<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtgcaggag cgggactgag tg                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcatttgca accgcaaccg cg                                              22

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgactaccg cacagtccaa cttgacc                                         27

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgtcttgaag agcaaggagt gg                                              22

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgtagtagt cgccgtgctc agccatc                                         27

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catggatcct ctagactgca ggcatgcaag cttctcga                             38

<210> SEQ ID NO 16
```

-continued

```
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctaggagatc tgacgtccgt acgttcgaag agctctag                               38

<210> SEQ ID NO 17
<211> LENGTH: 2051
<212> TYPE: PRT
<213> ORGANISM: Saccharomyces cerevisiae

<400> SEQUENCE: 17
```

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
            20                  25                  30

Leu Gln Glu Gln Phe Asn Lys Ile Leu Pro Glu Pro Thr Glu Gly Phe
        35                  40                  45

Ala Ala Asp Asp Glu Pro Thr Thr Pro Ala Glu Leu Val Gly Lys Phe
    50                  55                  60

Leu Gly Tyr Val Ser Ser Leu Val Glu Pro Ser Lys Val Gly Gln Phe
65                  70                  75                  80

Asp Gln Val Leu Asn Leu Cys Leu Thr Glu Phe Glu Asn Cys Tyr Leu
                85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Lys Ser Asn Ser Ala
    130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
        195                 200                 205

Phe Thr Gln Gly Leu Asn Ile Leu Glu Trp Leu Glu Asn Pro Ser Asn
    210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
            260                 265                 270

His Ser Gln Gly Leu Val Thr Ala Val Ala Ile Ala Glu Thr Asp Ser
        275                 280                 285

Trp Glu Ser Phe Phe Val Ser Val Arg Lys Ala Ile Thr Val Leu Phe
    290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser

```
                325                 330                 335
Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
            355                 360             365

Ser Leu Val Asn Gly Ala Lys Asn Leu Val Val Ser Gly Pro Pro Gln
370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                405                 410                 415

Ser Asn Arg Phe Leu Pro Val Ala Ser Pro Phe His Ser His Leu Leu
            420                 425                 430

Val Pro Ala Ser Asp Leu Ile Asn Lys Asp Leu Val Lys Asn Asn Val
            435                 440                 445

Ser Phe Asn Ala Lys Asp Ile Gln Ile Pro Val Tyr Asp Thr Phe Asp
450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Gln Phe
                485                 490                 495

Lys Ala Thr His Ile Leu Asp Phe Gly Pro Gly Ala Ser Gly Leu
            500                 505                 510

Gly Val Leu Thr His Arg Asn Lys Asp Gly Thr Gly Val Arg Val Ile
            515                 520                 525

Val Ala Gly Thr Leu Asp Ile Asn Pro Asp Asp Tyr Gly Phe Lys
530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Ser Gly Lys
                565                 570                 575

Ile Phe Val Glu Thr Lys Phe Ser Lys Leu Ile Gly Arg Pro Pro Leu
            580                 585                 590

Leu Val Pro Gly Met Thr Pro Cys Thr Val Ser Pro Asp Phe Val Ala
            595                 600                 605

Ala Thr Thr Asn Ala Gly Tyr Thr Ile Glu Leu Ala Gly Gly Gly Tyr
            610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
            660                 665                 670

Gly Tyr Pro Ile Gln Phe Leu Thr Ile Gly Ala Gly Val Pro Ser Leu
            675                 680                 685

Glu Val Ala Ser Glu Tyr Ile Glu Thr Leu Gly Leu Lys Tyr Leu Gly
            690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
            740                 745                 750
```

-continued

```
Met Tyr Ser Lys Ile Arg Arg His Pro Asn Ile Met Leu Ile Phe Gly
            755                 760                 765

Ser Gly Phe Gly Ser Ala Asp Asp Thr Tyr Pro Tyr Leu Thr Gly Glu
770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Asp Lys Trp
                820                 825                 830

Glu Gln Thr Tyr Lys Lys Pro Thr Gly Gly Ile Val Thr Val Arg Ser
                835                 840                 845

Glu Met Gly Glu Pro Ile His Lys Ile Ala Thr Arg Gly Val Met Leu
850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
                900                 905                 910

Asp Leu Ala Thr Met Thr Tyr Glu Glu Val Ala Lys Arg Leu Val Glu
                915                 920                 925

Leu Met Phe Ile Arg Ser Thr Asn Ser Trp Phe Asp Val Thr Trp Arg
930                 935                 940

Thr Phe Thr Gly Asp Phe Leu Arg Arg Val Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
                980                 985                 990

Gln Phe Leu Asn Ala Gln Asp Ile Asp His Phe Leu Ser Met Cys Gln
                995                 1000                1005

Asn Pro Met Gln Lys Pro Val Pro Phe Val Pro Val Leu Asp Arg
    1010                1015                1020

Arg Phe Glu Ile Phe Phe Lys Lys Asp Ser Leu Trp Gln Ser Glu
    1025                1030                1035

His Leu Glu Ala Val Val Asp Gln Asp Val Gln Arg Thr Cys Ile
    1040                1045                1050

Leu His Gly Pro Val Ala Ala Gln Phe Thr Lys Val Ile Asp Glu
    1055                1060                1065

Pro Ile Lys Ser Ile Met Asp Gly Ile His Asp Gly His Ile Lys
    1070                1075                1080

Lys Leu Leu His Gln Tyr Tyr Gly Asp Asp Glu Ser Lys Ile Pro
    1085                1090                1095

Ala Val Glu Tyr Phe Gly Gly Glu Ser Pro Val Asp Val Gln Ser
    1100                1105                1110

Gln Val Asp Ser Ser Ser Val Ser Glu Asp Ser Ala Val Phe Lys
    1115                1120                1125

Ala Thr Ser Ser Thr Asp Glu Glu Ser Trp Phe Lys Ala Leu Ala
    1130                1135                1140

Gly Ser Glu Ile Asn Trp Arg His Ala Ser Phe Leu Cys Ser Phe
    1145                1150                1155

Ile Thr Gln Asp Lys Met Phe Val Ser Asn Pro Ile Arg Lys Val
    1160                1165                1170
```

-continued

```
Phe Lys Pro Ser Gln Gly Met Val Val Glu Ile Ser Asn Gly Asn
    1175                1180                1185
Thr Ser Ser Lys Thr Val Val Thr Leu Ser Glu Pro Val Gln Gly
    1190                1195                1200
Glu Leu Lys Pro Thr Val Ile Leu Lys Leu Leu Lys Glu Asn Ile
    1205                1210                1215
Ile Gln Met Glu Met Ile Glu Asn Arg Thr Met Asp Gly Lys Pro
    1220                1225                1230
Val Ser Leu Pro Leu Leu Tyr Asn Phe Asn Pro Asp Asn Gly Phe
    1235                1240                1245
Ala Pro Ile Ser Glu Val Met Glu Asp Arg Asn Gln Arg Ile Lys
    1250                1255                1260
Glu Met Tyr Trp Lys Leu Trp Ile Asp Glu Pro Phe Asn Leu Asp
    1265                1270                1275
Phe Asp Pro Arg Asp Val Ile Lys Gly Lys Asp Phe Glu Ile Thr
    1280                1285                1290
Ala Lys Glu Val Tyr Asp Phe Thr His Ala Val Gly Asn Asn Cys
    1295                1300                1305
Glu Asp Phe Val Ser Arg Pro Asp Arg Thr Met Leu Ala Pro Met
    1310                1315                1320
Asp Phe Ala Ile Val Val Gly Trp Arg Ala Ile Ile Lys Ala Ile
    1325                1330                1335
Phe Pro Asn Thr Val Asp Gly Asp Leu Leu Lys Leu Val His Leu
    1340                1345                1350
Ser Asn Gly Tyr Lys Met Ile Pro Gly Ala Lys Pro Leu Gln Val
    1355                1360                1365
Gly Asp Val Val Ser Thr Thr Ala Val Ile Glu Ser Val Val Asn
    1370                1375                1380
Gln Pro Thr Gly Lys Ile Val Asp Val Val Gly Thr Leu Ser Arg
    1385                1390                1395
Asn Gly Lys Pro Val Met Glu Val Thr Ser Ser Phe Phe Tyr Arg
    1400                1405                1410
Gly Asn Tyr Thr Asp Phe Glu Asn Thr Phe Gln Lys Thr Val Glu
    1415                1420                1425
Pro Val Tyr Gln Met His Ile Lys Thr Ser Lys Asp Ile Ala Val
    1430                1435                1440
Leu Arg Ser Lys Glu Trp Phe Gln Leu Asp Asp Glu Asp Phe Asp
    1445                1450                1455
Leu Leu Asn Lys Thr Leu Thr Phe Glu Thr Glu Thr Glu Val Thr
    1460                1465                1470
Phe Lys Asn Ala Asn Ile Phe Ser Ser Val Lys Cys Phe Gly Pro
    1475                1480                1485
Ile Lys Val Glu Leu Pro Thr Lys Glu Thr Val Glu Ile Gly Ile
    1490                1495                1500
Val Asp Tyr Glu Ala Gly Ala Ser His Gly Asn Pro Val Val Asp
    1505                1510                1515
Phe Leu Lys Arg Asn Gly Ser Thr Leu Glu Gln Lys Val Asn Leu
    1520                1525                1530
Glu Asn Pro Ile Pro Ile Ala Val Leu Asp Ser Tyr Thr Pro Ser
    1535                1540                1545
Thr Asn Glu Pro Tyr Ala Arg Val Ser Gly Asp Leu Asn Pro Ile
    1550                1555                1560
His Val Ser Arg His Phe Ala Ser Tyr Ala Asn Leu Pro Gly Thr
```

```
                1565                1570                1575

Ile Thr His Gly Met Phe Ser Ser Ala Ser Val Arg Ala Leu Ile
    1580                1585                1590

Glu Asn Trp Ala Ala Asp Ser Val Ser Ser Arg Val Arg Gly Tyr
    1595                1600                1605

Thr Cys Gln Phe Val Asp Met Val Leu Pro Asn Thr Ala Leu Lys
    1610                1615                1620

Thr Ser Ile Gln His Val Gly Met Ile Asn Gly Arg Lys Leu Ile
    1625                1630                1635

Lys Phe Glu Thr Arg Asn Glu Asp Asp Val Val Leu Thr Gly
    1640                1645                1650

Glu Ala Glu Ile Glu Gln Pro Val Thr Thr Phe Val Phe Thr Gly
    1655                1660                1665

Gln Gly Ser Gln Glu Gln Gly Met Gly Met Asp Leu Tyr Lys Thr
    1670                1675                1680

Ser Lys Ala Ala Gln Asp Val Trp Asn Arg Ala Asp Asn His Phe
    1685                1690                1695

Lys Asp Thr Tyr Gly Phe Ser Ile Leu Asp Ile Val Ile Asn Asn
    1700                1705                1710

Pro Val Asn Leu Thr Ile His Phe Gly Gly Glu Lys Gly Lys Arg
    1715                1720                1725

Ile Arg Glu Asn Tyr Ser Ala Met Ile Phe Glu Thr Ile Val Asp
    1730                1735                1740

Gly Lys Leu Lys Thr Glu Lys Ile Phe Lys Glu Ile Asn Glu His
    1745                1750                1755

Ser Thr Ser Tyr Thr Phe Arg Ser Glu Lys Gly Leu Leu Ser Ala
    1760                1765                1770

Thr Gln Phe Thr Gln Pro Ala Leu Thr Leu Met Glu Lys Ala Ala
    1775                1780                1785

Phe Glu Asp Leu Lys Ser Lys Gly Leu Ile Pro Ala Asp Ala Thr
    1790                1795                1800

Phe Ala Gly His Ser Leu Gly Glu Tyr Ala Ala Leu Ala Ser Leu
    1805                1810                1815

Ala Asp Val Met Ser Ile Glu Ser Leu Val Glu Val Val Phe Tyr
    1820                1825                1830

Arg Gly Met Thr Met Gln Val Ala Val Pro Arg Asp Glu Leu Gly
    1835                1840                1845

Arg Ser Asn Tyr Gly Met Ile Ala Ile Asn Pro Gly Arg Val Ala
    1850                1855                1860

Ala Ser Phe Ser Gln Glu Ala Leu Gln Tyr Val Val Glu Arg Val
    1865                1870                1875

Gly Lys Arg Thr Gly Trp Leu Val Glu Ile Val Asn Tyr Asn Val
    1880                1885                1890

Glu Asn Gln Gln Tyr Val Ala Ala Gly Asp Leu Arg Ala Leu Asp
    1895                1900                1905

Thr Val Thr Asn Val Leu Asn Phe Ile Lys Leu Gln Lys Ile Asp
    1910                1915                1920

Ile Ile Glu Leu Gln Lys Ser Leu Ser Leu Glu Glu Val Glu Gly
    1925                1930                1935

His Leu Phe Glu Ile Ile Asp Glu Ala Ser Lys Lys Ser Ala Val
    1940                1945                1950

Lys Pro Arg Pro Leu Lys Leu Glu Arg Gly Phe Ala Cys Ile Pro
    1955                1960                1965
```

-continued

Leu Val Gly Ile Ser Val Pro Phe His Ser Thr Tyr Leu Met Asn
    1970            1975                1980

Gly Val Lys Pro Phe Lys Ser Phe Leu Lys Lys Asn Ile Ile Lys
    1985            1990                1995

Glu Asn Val Lys Val Ala Arg Leu Ala Gly Lys Tyr Ile Pro Asn
    2000            2005                2010

Leu Thr Ala Lys Pro Phe Gln Val Thr Lys Glu Tyr Phe Gln Asp
    2015            2020                2025

Val Tyr Asp Leu Thr Gly Ser Glu Pro Ile Lys Glu Ile Ile Asp
    2030            2035                2040

Asn Trp Glu Lys Tyr Glu Gln Ser
    2045            2050

<210> SEQ ID NO 18
<211> LENGTH: 2037
<212> TYPE: PRT
<213> ORGANISM: Candida albicans

<400> SEQUENCE: 18

Met Ser Thr His Arg Pro Phe Gln Leu Thr His Gly Ser Ile Glu His
1               5                   10                  15

Thr Leu Leu Val Pro Asn Asp Leu Phe Phe Asn Tyr Ser Gln Leu Lys
                20                  25                  30

Asp Glu Phe Ile Lys Thr Leu Pro Glu Pro Thr Glu Gly Phe Ala Gly
            35                  40                  45

Asp Asp Glu Pro Ser Ser Pro Ala Glu Leu Tyr Gly Lys Phe Ile Gly
        50                  55                  60

Phe Ile Ser Asn Ala Gln Phe Pro Gln Ile Val Glu Leu Ser Leu Lys
65                  70                  75                  80

Asp Phe Glu Ser Arg Phe Leu Asp Asn Asn Asn Asp Asn Ile His Ser
                85                  90                  95

Phe Ala Val Lys Leu Leu Asp Asp Glu Thr Tyr Pro Thr Thr Ile Ala
            100                 105                 110

Lys Val Lys Glu Asn Ile Val Lys Asn Tyr Tyr Lys Ala Val Lys Ser
        115                 120                 125

Ile Asn Lys Val Glu Ser Asn Leu Leu Tyr His Cys Lys His Asp Ala
130                 135                 140

Lys Leu Val Ala Ile Phe Gly Gly Gln Gly Asn Thr Asp Asp Tyr Phe
145                 150                 155                 160

Glu Glu Leu Arg Glu Leu Tyr Thr Leu Tyr Gln Gly Leu Ile Glu Asp
                165                 170                 175

Leu Leu Val Ser Ile Ala Glu Lys Leu Asn Gln Leu His Pro Ser Phe
            180                 185                 190

Asp Lys Ile Tyr Thr Gln Gly Leu Asn Ile Leu Ser Trp Leu Lys His
        195                 200                 205

Pro Glu Thr Thr Pro Asp Gln Asp Tyr Leu Leu Ser Val Pro Val Ser
    210                 215                 220

Cys Pro Val Ile Cys Val Ile Gln Leu Cys His Tyr Thr Ile Thr Cys
225                 230                 235                 240

Lys Val Leu Gly Leu Thr Pro Gly Glu Phe Arg Asn Ser Leu Lys Trp
                245                 250                 255

Ser Thr Gly His Ser Gln Gly Leu Val Thr Ala Val Thr Ile Ala Ala
            260                 265                 270

Ser Asp Ser Trp Asp Ser Phe Leu Lys Asn Ser Leu Thr Ala Val Ser
        275                 280                 285

```
Leu Leu Leu Phe Ile Gly Ser Arg Cys Leu Ser Thr Tyr Pro Arg Thr
        290                 295                 300

Ser Leu Pro Pro Thr Met Leu Gln Asp Ser Leu Asp Asn Gly Glu Gly
305                 310                 315                 320

Arg Pro Ser Pro Met Leu Ser Val Arg Asp Leu Ser Ile Lys Gln Val
                    325                 330                 335

Glu Lys Phe Ile Glu Gln Thr Asn Ser His Leu Pro Arg Glu Lys His
                340                 345                 350

Ile Ala Ile Ser Leu Ile Asn Gly Ala Arg Asn Leu Val Leu Ser Gly
            355                 360                 365

Pro Pro Glu Ser Leu Tyr Gly Phe Asn Leu Asn Leu Arg Asn Gln Lys
370                 375                 380

Ala Pro Met Gly Leu Asp Gln Ser Arg Val Pro Phe Ser Glu Arg Lys
385                 390                 395                 400

Leu Lys Cys Ser Asn Arg Phe Leu Pro Ile Phe Ala Pro Phe His Ser
                405                 410                 415

His Leu Leu Ala Asp Ala Thr Glu Leu Ile Leu Asp Asp Val Lys Glu
                420                 425                 430

His Gly Leu Ser Phe Glu Gly Leu Lys Ile Pro Val Tyr Asp Thr Phe
            435                 440                 445

Asp Gly Ser Asp Phe Gln Ala Leu Lys Glu Pro Ile Ile Asp Arg Val
        450                 455                 460

Val Lys Leu Ile Thr Glu Leu Pro Val His Trp Glu Glu Ala Thr Asn
465                 470                 475                 480

His Lys Ala Thr His Ile Leu Asp Phe Gly Pro Gly Val Ser Gly
                485                 490                 495

Leu Gly Val Leu Thr His Arg Asn Lys Glu Gly Thr Gly Ala Arg Ile
                500                 505                 510

Ile Leu Ala Gly Thr Leu Asp Ser Asn Pro Ile Asp Asp Glu Tyr Gly
            515                 520                 525

Phe Lys His Glu Ile Phe Gln Thr Ser Ala Asp Lys Ala Ile Lys Trp
530                 535                 540

Ala Pro Asp Trp Leu Lys Glu Leu Arg Pro Thr Leu Val Lys Asn Ser
545                 550                 555                 560

Glu Gly Lys Ile Tyr Val Lys Thr Lys Phe Ser Gln Leu Leu Gly Arg
                565                 570                 575

Ala Pro Leu Met Val Ala Gly Met Thr Pro Thr Thr Val Asn Thr Asp
            580                 585                 590

Ile Val Ser Ala Ser Leu Asn Ala Gly Tyr His Ile Glu Leu Ala Gly
        595                 600                 605

Gly Gly Tyr Phe Ser Pro Val Met Met Thr Arg Ala Ile Asp Asp Ile
610                 615                 620

Val Ser Arg Ile Lys Pro Gly Tyr Gly Leu Gly Ile Asn Leu Ile Tyr
625                 630                 635                 640

Val Asn Pro Phe Met Leu Gln Trp Gly Ile Pro Leu Ile Lys Asp Leu
                645                 650                 655

Arg Glu Lys Gly Tyr Pro Ile Gln Ser Leu Thr Ile Gly Ala Gly Val
                660                 665                 670

Pro Ser Ile Glu Val Ala Thr Glu Tyr Ile Glu Asp Leu Gly Leu Thr
            675                 680                 685

His Leu Gly Leu Lys Pro Gly Ser Val Asp Ala Ile Ser Gln Val Ile
        690                 695                 700

Ala Ile Ala Lys Ala His Pro Thr Phe Pro Ile Val Leu Gln Trp Thr
705                 710                 715                 720
```

```
Gly Gly Arg Gly Gly Gly His His Ser Phe Glu Asp Phe His Gln Pro
            725                 730                 735
Ile Ile Gln Met Tyr Ser Lys Ile Arg Arg Cys Ser Asn Ile Val Leu
            740                 745                 750
Val Ala Gly Ser Gly Phe Gly Ser Asp Glu Asp Thr Tyr Pro Tyr Leu
            755                 760                 765
Ser Gly Tyr Trp Ser Glu Lys Phe Asn Tyr Pro Pro Met Pro Phe Asp
            770                 775                 780
Gly Val Leu Phe Gly Ser Arg Val Met Thr Ser Lys Glu Ser His Thr
785                 790                 795                 800
Ser Leu Ala Ala Lys Lys Leu Ile Val Glu Cys Lys Gly Val Pro Asp
            805                 810                 815
Gln Gln Trp Glu Gln Thr Tyr Lys Lys Pro Thr Gly Gly Ile Ile Thr
            820                 825                 830
Val Arg Ser Glu Met Gly Glu Pro Ile His Lys Ile Ala Thr Arg Gly
            835                 840                 845
Val Met Phe Trp Lys Glu Leu Asp Asp Thr Ile Phe Asn Leu Pro Lys
            850                 855                 860
Asn Lys Leu Leu Asp Ala Leu Asn Lys Lys Arg Asp His Ile Ile Lys
865                 870                 875                 880
Lys Leu Asn Asn Asp Phe Gln Lys Pro Trp Phe Gly Lys Asn Ala Asn
            885                 890                 895
Gly Val Cys Asp Leu Gln Glu Met Thr Tyr Lys Glu Val Ala Asn Arg
            900                 905                 910
Leu Val Glu Leu Met Tyr Val Lys Lys Ser His Arg Trp Ile Asp Val
            915                 920                 925
Ser Leu Arg Asn Met Tyr Gly Asp Phe Leu Arg Arg Val Glu Glu Arg
            930                 935                 940
Phe Thr Ser Ser Ala Gly Thr Val Ser Leu Leu Gln Asn Phe Asn Gln
945                 950                 955                 960
Leu Asn Glu Pro Glu Gln Phe Thr Ala Asp Phe Phe Glu Lys Phe Pro
            965                 970                 975
Gln Ala Gly Lys Gln Leu Ile Ser Glu Asp Cys Asp Tyr Phe Leu
            980                 985                 990
Met Leu Ala Ala Arg Pro Gly Gln Lys Pro Val Pro Phe Val Pro Val
            995                 1000                1005
Leu Asp Glu Arg Phe Glu Phe Phe Lys Lys Asp Ser Leu Trp
    1010                1015                1020
Gln Ser Glu Asp Leu Glu Ser Val Val Asp Glu Asp Val Gln Arg
    1025                1030                1035
Thr Cys Ile Leu His Gly Pro Val Ala Ser Gln Tyr Thr Ser Lys
    1040                1045                1050
Val Asp Glu Pro Ile Gly Asp Ile Leu Asn Ser Ile His Glu Gly
    1055                1060                1065
His Ile Ala Arg Leu Ile Lys Glu Glu Tyr Ala Gly Asp Glu Ser
    1070                1075                1080
Lys Ile Pro Val Val Glu Tyr Phe Gly Gly Lys Lys Pro Ala Ser
    1085                1090                1095
Val Ser Ala Thr Ser Val Asn Ile Ile Asp Gly Asn Gln Val Val
    1100                1105                1110
Tyr Glu Ile Asp Ser Glu Leu Pro Asn Lys Gln Glu Trp Leu Asp
    1115                1120                1125
Leu Leu Ala Gly Thr Glu Leu Asn Trp Leu Gln Ala Phe Ile Ser
```

-continued

```
            1130                1135                1140
Thr Asp Arg Ile Val Gln Gly Ser Lys His Val Ser Asn Pro Leu
    1145                1150                1155
His Asp Ile Leu Thr Pro Ala Lys His Ser Lys Val Thr Ile Asp
    1160                1165                1170
Lys Lys Thr Lys Lys Leu Thr Ala Phe Glu Asn Ile Lys Gly Asp
    1175                1180                1185
Leu Leu Pro Val Val Glu Ile Glu Leu Val Lys Pro Asn Thr Ile
    1190                1195                1200
Gln Leu Ser Leu Ile Glu His Arg Thr Ala Asp Thr Asn Pro Val
    1205                1210                1215
Ala Leu Pro Phe Leu Tyr Lys Tyr Asn Pro Ala Asp Gly Phe Ala
    1220                1225                1230
Pro Ile Leu Glu Ile Met Glu Asp Arg Asn Glu Arg Ile Lys Glu
    1235                1240                1245
Phe Tyr Trp Lys Leu Trp Phe Gly Ser Ser Val Pro Tyr Ser Asn
    1250                1255                1260
Asp Ile Asn Val Glu Lys Ala Ile Leu Gly Asp Glu Ile Thr Ile
    1265                1270                1275
Ser Ser Gln Thr Ile Ser Glu Phe Thr His Ala Ile Gly Asn Lys
    1280                1285                1290
Cys Asp Ala Phe Val Asp Arg Pro Gly Lys Ala Thr Leu Ala Pro
    1295                1300                1305
Met Asp Phe Ala Ile Val Ile Gly Trp Lys Ala Ile Ile Lys Ala
    1310                1315                1320
Ile Phe Pro Lys Ser Val Asp Gly Asp Leu Leu Lys Leu Val His
    1325                1330                1335
Leu Ser Asn Gly Tyr Lys Met Ile Thr Gly Ala Ala Pro Leu Lys
    1340                1345                1350
Lys Gly Asp Val Val Ser Thr Lys Ala Glu Ile Lys Ala Val Leu
    1355                1360                1365
Asn Gln Pro Ser Gly Lys Leu Val Glu Val Val Gly Thr Ile Tyr
    1370                1375                1380
Arg Glu Gly Lys Pro Val Met Glu Val Thr Ser Gln Phe Leu Tyr
    1385                1390                1395
Arg Gly Glu Tyr Asn Asp Tyr Cys Asn Thr Phe Gln Lys Val Thr
    1400                1405                1410
Glu Thr Pro Val Gln Val Ala Phe Lys Ser Ala Lys Asp Leu Ala
    1415                1420                1425
Val Leu Arg Ser Lys Glu Trp Phe His Leu Glu Lys Asp Val Gln
    1430                1435                1440
Phe Asp Val Leu Thr Phe Arg Cys Glu Ser Thr Tyr Lys Phe Lys
    1445                1450                1455
Ser Ala Asn Val Tyr Ser Ser Ile Lys Thr Thr Gly Gln Val Leu
    1460                1465                1470
Leu Glu Leu Pro Thr Lys Glu Val Ile Gln Val Gly Ser Val Asp
    1475                1480                1485
Tyr Glu Ala Gly Thr Ser Tyr Gly Asn Pro Val Thr Asp Tyr Leu
    1490                1495                1500
Ser Arg Asn Gly Lys Thr Ile Glu Glu Ser Val Ile Phe Glu Asn
    1505                1510                1515
Ala Ile Pro Leu Ser Ser Gly Glu Glu Leu Thr Ser Lys Ala Pro
    1520                1525                1530
```

-continued

```
Gly Thr Asn Glu Pro Tyr Ala Ile Val Ser Gly Asp Tyr Asn Pro
1535                1540                1545

Ile His Val Ser Arg Val Phe Ala Ala Tyr Ala Lys Leu Pro Gly
    1550                1555                1560

Thr Ile Thr His Gly Met Tyr Ser Ser Ala Ser Ile Arg Ala Leu
    1565                1570                1575

Val Glu Glu Trp Ala Ala Asn Asn Val Ala Ala Arg Val Arg Ala
    1580                1585                1590

Phe Lys Cys Asp Phe Val Gly Met Val Leu Pro Asn Asp Thr Leu
    1595                1600                1605

Gln Thr Thr Met Glu His Val Gly Met Ile Asn Gly Arg Lys Ile
    1610                1615                1620

Ile Lys Val Glu Thr Arg Asn Val Glu Thr Glu Leu Pro Val Leu
    1625                1630                1635

Ile Gly Glu Ala Glu Ile Glu Gln Pro Thr Thr Thr Tyr Val Phe
    1640                1645                1650

Thr Gly Gln Gly Ser Gln Glu Gln Gly Met Gly Met Glu Leu Tyr
    1655                1660                1665

Asn Ser Ser Glu Val Ala Arg Glu Val Trp Asp Lys Ala Asp Arg
    1670                1675                1680

His Phe Val Asn Asn Tyr Gly Phe Ser Ile Leu Asp Ile Val Gln
    1685                1690                1695

Asn Asn Pro Asn Glu Leu Thr Ile His Phe Gly Ala Lys Gly
    1700                1705                1710

Arg Ala Ile Arg Asp Asn Tyr Ile Gly Met Met Phe Glu Thr Ile
    1715                1720                1725

Gly Glu Asp Gly Ala Leu Lys Ser Glu Lys Ile Phe Lys Asp Ile
    1730                1735                1740

Asp Glu Thr Thr Thr Ser Tyr Thr Phe Val Ser Pro Thr Gly Leu
    1745                1750                1755

Leu Ser Ala Thr Gln Phe Thr Gln Pro Ala Leu Thr Leu Met Glu
    1760                1765                1770

Lys Ala Ala Tyr Glu Asp Ile Lys Ser Lys Gly Leu Ile Pro Ser
    1775                1780                1785

Asp Ile Met Phe Ala Gly His Ser Leu Gly Glu Tyr Ser Ala Leu
    1790                1795                1800

Ser Ser Leu Ala Asn Val Met Pro Ile Glu Ser Leu Val Asp Val
    1805                1810                1815

Val Phe Tyr Arg Gly Met Thr Met Gln Val Ala Val Pro Arg Asp
    1820                1825                1830

Glu Leu Gly Arg Ser Asn Tyr Gly Met Val Ala Val Asn Pro Ser
    1835                1840                1845

Arg Val Ser Ala Thr Phe Asp Ser Ala Leu Arg Phe Val Val
    1850                1855                1860

Asp Glu Val Ala Asn Lys Thr Lys Trp Leu Leu Glu Ile Val Asn
    1865                1870                1875

Tyr Asn Val Glu Asn Gln Gln Tyr Val Ala Ala Gly Asp Leu Arg
    1880                1885                1890

Ala Leu Asp Thr Leu Thr Asn Val Leu Asn Val Leu Lys Ile Asn
    1895                1900                1905

Lys Ile Asp Ile Val Lys Leu Gln Glu Gln Met Ser Ile Glu Lys
    1910                1915                1920

Val Lys Glu His Leu Tyr Glu Ile Val Asp Glu Val Ala Ala Lys
    1925                1930                1935
```

```
Ser Leu Ala Lys Pro Gln Pro Ile Asp Leu Glu Arg Gly Phe Ala
    1940              1945                1950

Val Ile Pro Leu Lys Gly Ile Ser Val Pro Phe His Ser Ser Tyr
    1955              1960                1965

Leu Met Ser Gly Val Lys Pro Phe Gln Arg Phe Leu Cys Lys Lys
    1970              1975                1980

Ile Pro Lys Ser Ser Val Pro Gln Asp Leu Ile Gly Lys Tyr
    1985              1990                1995

Ile Pro Asn Leu Thr Ala Lys Pro Phe Glu Leu Thr Lys Glu Tyr
    2000              2005                2010

Phe Gln Ser Val Tyr Asp Leu Thr Lys Ser Glu Lys Ile Lys Ser
    2015              2020                2025

Ile Leu Asp Asn Trp Glu Gln Tyr Glu
    2030              2035

<210> SEQ ID NO 19
<211> LENGTH: 2091
<212> TYPE: PRT
<213> ORGANISM: Aspergillus nidulans

<400> SEQUENCE: 19

Met Tyr Gly Thr Ser Thr Gly Pro Gln Thr Gly Ile Asn Thr Pro Arg
1               5                   10                  15

Ser Ser Gln Ser Leu Arg Pro Leu Ile Leu Ser His Gly Ser Leu Glu
                20                  25                  30

Phe Ser Phe Leu Val Pro Thr Ser Leu His Phe His Ala Ser Gln Leu
            35                  40                  45

Lys Asp Thr Phe Thr Ala Ser Leu Pro Glu Pro Thr Asp Glu Leu Ala
        50                  55                  60

Gln Asp Asp Glu Pro Ser Ser Val Ala Glu Leu Val Ala Arg Tyr Ile
65                  70                  75                  80

Gly His Val Ala His Glu Val Glu Gly Glu Asp Asp Ala His Gly
                85                  90                  95

Thr Asn Gln Asp Val Leu Lys Leu Thr Leu Asn Glu Phe Glu Arg Ala
            100                 105                 110

Phe Met Arg Gly Asn Asp Val His Ala Val Ala Ala Thr Leu Pro Gly
        115                 120                 125

Ile Thr Ala Lys Lys Val Leu Val Glu Ala Tyr Tyr Ala Gly Arg
    130                 135                 140

Ala Ala Ala Gly Arg Pro Thr Lys Pro Tyr Asp Ser Ala Leu Phe Arg
145                 150                 155                 160

Ala Ala Ser Asp Glu Lys Ala Arg Ile Tyr Ser Val Leu Gly Gly Gln
                165                 170                 175

Gly Asn Ile Glu Glu Tyr Phe Asp Glu Leu Arg Glu Val Tyr Asn Thr
            180                 185                 190

Tyr Thr Ser Phe Val Asp Asp Leu Ile Ser Ser Ser Ala Glu Leu Leu
        195                 200                 205

Gln Ser Leu Ser Arg Glu Pro Asp Ala Asn Lys Leu Tyr Pro Lys Gly
    210                 215                 220

Leu Asn Val Met Gln Trp Leu Arg Glu Pro Thr Gln Pro Asp Val
225                 230                 235                 240

Asp Tyr Leu Val Ser Ala Pro Val Ser Leu Pro Leu Ile Gly Leu Val
                245                 250                 255

Gln Leu Ala His Phe Ala Val Thr Cys Arg Val Leu Gly Lys Glu Pro
            260                 265                 270
```

```
Gly Glu Ile Leu Glu Arg Phe Ser Gly Thr Thr Gly His Ser Gln Gly
            275                 280                 285
Ile Val Thr Ala Ala Ala Ile Ala Thr Ala Thr Thr Trp Glu Ser Phe
        290                 295                 300
His Lys Ala Val Ala Asn Ala Leu Thr Met Leu Phe Trp Ile Gly Leu
305                 310                 315                 320
Arg Ser Gln Gln Ala Tyr Pro Arg Thr Ser Ile Ala Pro Ser Val Leu
                325                 330                 335
Gln Asp Ser Ile Glu Asn Gly Glu Gly Thr Pro Thr Pro Met Leu Ser
            340                 345                 350
Ile Arg Asp Leu Pro Arg Thr Ala Val Gln Glu His Ile Asp Met Thr
        355                 360                 365
Asn Gln His Leu Pro Glu Asp Arg His Ile Ser Ile Ser Leu Val Asn
    370                 375                 380
Ser Ala Arg Asn Phe Val Val Thr Gly Pro Pro Leu Ser Leu Tyr Gly
385                 390                 395                 400
Leu Asn Leu Arg Leu Arg Lys Val Lys Ala Pro Thr Gly Leu Asp Gln
                405                 410                 415
Asn Arg Val Pro Phe Thr Gln Arg Lys Val Arg Phe Val Asn Arg Phe
            420                 425                 430
Leu Pro Ile Thr Ala Pro Phe His Ser Gln Tyr Leu Tyr Ser Ala Phe
        435                 440                 445
Asp Arg Ile Met Glu Asp Leu Glu Asp Val Glu Ile Ser Pro Lys Ser
    450                 455                 460
Leu Thr Ile Pro Val Tyr Gly Thr Lys Thr Gly Asp Asp Leu Arg Ala
465                 470                 475                 480
Ile Ser Asp Ala Asn Val Val Pro Ala Leu Val Arg Met Ile Thr His
                485                 490                 495
Asp Pro Val Asn Trp Glu Gln Thr Thr Ala Phe Pro Asn Ala Thr His
            500                 505                 510
Ile Val Asp Phe Gly Pro Gly Gly Ile Ser Gly Leu Gly Val Leu Thr
        515                 520                 525
Asn Arg Asn Lys Asp Gly Thr Gly Val Arg Val Ile Leu Ala Gly Ser
    530                 535                 540
Met Asp Gly Thr Asn Ala Glu Val Gly Tyr Lys Pro Glu Leu Phe Asp
545                 550                 555                 560
Arg Asp Glu His Ser Val Lys Tyr Ala Ile Asp Trp Val Lys Glu Tyr
                565                 570                 575
Gly Pro Arg Leu Val Lys Asn Ala Thr Gly Gln Thr Phe Val Asp Thr
            580                 585                 590
Lys Met Ser Arg Leu Leu Gly Ile Pro Pro Ile Met Val Ala Gly Met
        595                 600                 605
Thr Pro Thr Thr Val Pro Trp Asp Phe Val Ala Thr Met Asn Ala
    610                 615                 620
Gly Tyr His Ile Glu Leu Ala Gly Gly Gly Tyr Tyr Asn Ala Lys Thr
625                 630                 635                 640
Met Thr Glu Ala Ile Thr Lys Ile Glu Lys Ala Ile Pro Pro Gly Arg
                645                 650                 655
Gly Ile Thr Val Asn Leu Ile Tyr Val Asn Pro Arg Ala Met Gly Trp
            660                 665                 670
Gln Ile Pro Leu Ile Gly Lys Leu Arg Ala Asp Gly Val Pro Ile Glu
        675                 680                 685
Gly Leu Thr Ile Gly Ala Gly Val Pro Ser Ile Glu Val Ala Asn Glu
```

-continued

```
              690             695             700
Tyr Ile Glu Thr Leu Gly Ile Lys His Ile Ala Phe Lys Pro Gly Ser
705                     710                 715                 720

Val Asp Ala Ile Gln Gln Val Ile Asn Ile Ala Lys Ala Asn Pro Lys
                    725                 730                 735

Phe Pro Val Ile Leu Gln Trp Thr Gly Arg Gly Gly His His
                740                 745                 750

Ser Phe Glu Asp Phe His Gln Pro Ile Leu Gln Met Tyr Ser Arg Ile
        755                 760                 765

Arg Arg His Glu Asn Ile Ile Leu Val Ala Gly Ser Gly Phe Gly Gly
770                 775                 780

Ala Glu Asp Thr Tyr Pro Tyr Leu Ser Gly Asn Trp Ser Ser Arg Phe
785                 790                 795                 800

Gly Tyr Pro Pro Met Pro Phe Asp Gly Cys Leu Phe Gly Ser Arg Met
                805                 810                 815

Met Thr Ala Lys Glu Ala His Thr Ser Lys Asn Ala Lys Gln Ala Ile
            820                 825                 830

Val Asp Ala Pro Gly Leu Asp Asp Gln Asp Trp Glu Lys Thr Tyr Lys
            835                 840                 845

Gly Ala Ala Gly Gly Val Val Thr Val Leu Ser Glu Met Gly Glu Pro
850                 855                 860

Ile His Lys Leu Ala Thr Arg Gly Val Leu Phe Trp His Glu Met Asp
865                 870                 875                 880

Gln Lys Ile Phe Lys Leu Asp Lys Ala Lys Arg Val Pro Glu Leu Lys
                885                 890                 895

Lys Gln Arg Asp Tyr Ile Ile Lys Lys Leu Asn Asp Asp Phe Gln Lys
            900                 905                 910

Val Trp Phe Gly Arg Asn Ser Ala Gly Glu Thr Val Asp Leu Glu Asp
            915                 920                 925

Met Thr Tyr Ala Glu Val Val His Arg Met Val Asp Leu Met Tyr Val
            930                 935                 940

Lys His Glu Gly Arg Trp Ile Asp Asp Ser Leu Lys Lys Leu Thr Gly
945                 950                 955                 960

Asp Phe Ile Arg Arg Val Glu Glu Arg Phe Thr Thr Ala Glu Gly Gln
                965                 970                 975

Ala Ser Leu Leu Gln Asn Tyr Ser Glu Leu Asn Val Pro Tyr Pro Ala
            980                 985                 990

Val Asp Asn Ile Leu Ala Ala Tyr Pro Glu Ala Ala Thr Gln Leu Ile
            995                 1000                1005

Asn Ala Gln Asp Val Gln His Phe Leu Leu Leu Cys Gln Arg Arg
    1010                1015                1020

Gly Gln Lys Pro Val Pro Phe Val Pro Ser Leu Asp Glu Asn Phe
    1025                1030                1035

Glu Tyr Trp Phe Lys Lys Asp Ser Leu Trp Gln Ser Glu Asp Leu
    1040                1045                1050

Glu Ala Val Val Gly Gln Asp Val Gly Arg Thr Cys Ile Leu Gln
    1055                1060                1065

Gly Pro Met Ala Ala Lys Phe Ser Thr Val Ile Asp Glu Pro Val
    1070                1075                1080

Gly Asp Ile Leu Asn Ser Ile His Gln Gly His Ile Lys Ser Leu
    1085                1090                1095

Ile Lys Asp Met Tyr Asn Gly Asp Glu Thr Thr Ile Pro Ile Thr
    1100                1105                1110
```

```
Glu Tyr Phe Gly Gly Arg Leu Ser Glu Ala Gln Glu Asp Ile Glu
1115                1120                1125

Met Asp Gly Leu Thr Ile Ser Glu Asp Ala Asn Lys Ile Ser Tyr
1130                1135                1140

Arg Leu Ser Ser Ser Ala Ala Asp Leu Pro Glu Val Asn Arg Trp
1145                1150                1155

Cys Arg Leu Leu Ala Gly Arg Ser Tyr Ser Trp Arg His Ala Leu
1160                1165                1170

Phe Ser Ala Asp Val Phe Val Gln Gly His Arg Phe Gln Thr Asn
1175                1180                1185

Pro Leu Lys Arg Val Leu Ala Pro Ser Thr Gly Met Tyr Val Glu
1190                1195                1200

Ile Ala Asn Pro Glu Asp Ala Pro Lys Thr Val Ile Ser Val Arg
1205                1210                1215

Glu Pro Tyr Gln Ser Gly Lys Leu Val Lys Thr Val Asp Ile Lys
1220                1225                1230

Leu Asn Glu Lys Gly Pro Ile Ala Leu Thr Leu Tyr Glu Gly Arg
1235                1240                1245

Thr Ala Glu Asn Gly Val Val Pro Leu Thr Phe Leu Phe Thr Tyr
1250                1255                1260

His Pro Asp Thr Gly Tyr Ala Pro Ile Arg Glu Val Met Asp Ser
1265                1270                1275

Arg Asn Asp Arg Ile Lys Glu Phe Tyr Tyr Arg Ile Trp Phe Gly
1280                1285                1290

Asn Lys Asp Val Pro Phe Tyr Thr Pro Thr Thr Ala Thr Phe Asn
1295                1300                1305

Gly Gly Arg Glu Thr Ile Thr Ser Gln Ala Val Ala Asp Phe Val
1310                1315                1320

His Ala Val Gly Asn Thr Gly Glu Ala Phe Val Glu Arg Pro Gly
1325                1330                1335

Lys Glu Val Phe Ala Pro Met Asp Phe Ala Ile Val Ala Gly Trp
1340                1345                1350

Lys Ala Ile Thr Lys Pro Ile Phe Pro Arg Thr Ile Asp Gly Asp
1355                1360                1365

Leu Leu Lys Leu Val His Leu Ser Asn Gly Phe Lys Met Val Pro
1370                1375                1380

Gly Ala Gln Pro Leu Lys Val Gly Asp Val Leu Asp Thr Thr Ala
1385                1390                1395

Gln Ile Asn Ser Ile Ile Asn Glu Glu Ser Gly Lys Ile Val Glu
1400                1405                1410

Val Cys Gly Thr Ile Arg Arg Asp Gly Lys Pro Ile Met His Val
1415                1420                1425

Thr Ser Gln Phe Leu Tyr Arg Gly Ala Tyr Thr Asp Phe Glu Asn
1430                1435                1440

Thr Phe Gln Arg Lys Asp Glu Val Pro Met Gln Val His Leu Ala
1445                1450                1455

Ser Ser Arg Asp Val Ala Ile Leu Arg Ser Lys Glu Trp Phe Arg
1460                1465                1470

Leu Asp Met Asp Asp Val Glu Leu Leu Gly Gln Thr Leu Thr Phe
1475                1480                1485
```

```
Arg Leu Gln Ser Leu Ile Arg Phe Lys Asn Lys Asn Val Phe Ser
    1490                1495                1500

Gln Val Gln Thr Met Gly Gln Val Leu Leu Glu Leu Pro Thr Lys
    1505                1510                1515

Glu Val Ile Gln Val Ala Ser Val Asp Tyr Glu Ala Gly Thr Ser
    1520                1525                1530

His Gly Asn Pro Val Ile Asp Tyr Leu Gln Arg Asn Gly Thr Ser
    1535                1540                1545

Ile Glu Gln Pro Val Tyr Phe Glu Asn Pro Ile Pro Leu Ser Gly
    1550                1555                1560

Lys Thr Pro Leu Val Leu Arg Ala Pro Ala Ser Asn Glu Thr Tyr
    1565                1570                1575

Ala Arg Val Ser Gly Asp Tyr Asn Pro Ile His Val Ser Arg Val
    1580                1585                1590

Phe Ser Ser Tyr Ala Asn Leu Pro Gly Thr Ile Thr His Gly Met
    1595                1600                1605

Tyr Thr Ser Ala Ala Val Arg Ser Leu Val Glu Thr Trp Ala Ala
    1610                1615                1620

Glu Asn Asn Ile Gly Arg Val Arg Gly Phe His Val Ser Leu Val
    1625                1630                1635

Asp Met Val Leu Pro Asn Asp Leu Ile Thr Val Arg Leu Gln His
    1640                1645                1650

Val Gly Met Ile Ala Gly Arg Lys Ile Ile Lys Val Glu Ala Ser
    1655                1660                1665

Asn Lys Glu Thr Glu Asp Lys Val Leu Leu Gly Glu Ala Glu Val
    1670                1675                1680

Glu Gln Pro Val Thr Ala Tyr Val Phe Thr Gly Gln Gly Ser Gln
    1685                1690                1695

Glu Gln Gly Met Gly Met Glu Leu Tyr Ala Thr Ser Pro Val Ala
    1700                1705                1710

Lys Glu Val Trp Asp Arg Pro Ser Phe His Trp Asn Tyr Gly Leu
    1715                1720                1725

Ser Ile Ile Asp Ile Val Lys Asn Asn Pro Lys Glu Arg Thr Val
    1730                1735                1740

His Phe Gly Gly Pro Arg Gly Lys Ala Ile Arg Gln Asn Tyr Met
    1745                1750                1755

Ser Met Thr Phe Glu Thr Val Asn Ala Asp Gly Thr Ile Lys Ser
    1760                1765                1770

Glu Lys Ile Phe Lys Glu Ile Asp Glu Thr Thr Thr Ser Tyr Thr
    1775                1780                1785

Tyr Arg Ser Pro Thr Gly Leu Leu Ser Ala Thr Gln Phe Thr Gln
    1790                1795                1800

Pro Ala Leu Thr Leu Met Glu Lys Ala Ser Phe Glu Asp Met Arg
    1805                1810                1815

Ser Lys Gly Leu Val Gln Arg Asp Ser Ser Phe Ala Gly His Ser
    1820                1825                1830

Leu Gly Glu Tyr Ser Ala Leu Ala Asp Leu Ala Asp Val Met Leu
    1835                1840                1845

Ile Glu Ser Leu Val Ser Val Val Phe Tyr Arg Gly Leu Thr Met
    1850                1855                1860

Gln Val Ala Val Glu Arg Asp Glu Gln Gly Arg Ser Asn Tyr Ser
    1865                1870                1875

Met Cys Ala Val Asn Pro Ser Arg Ile Ser Lys Thr Phe Asn Glu
    1880                1885                1890
```

```
Gln Ala Leu Gln Tyr Val Val Gly Asn Ile Ser Glu Gln Thr Gly
    1895            1900            1905

Trp Leu Leu Glu Ile Val Asn Tyr Asn Val Ala Asn Met Gln Tyr
    1910            1915            1920

Val Ala Ala Gly Asp Leu Arg Ala Leu Asp Cys Leu Thr Asn Leu
    1925            1930            1935

Leu Asn Tyr Leu Lys Ala Gln Asn Ile Asp Ile Pro Ala Leu Met
    1940            1945            1950

Gln Ser Met Ser Leu Glu Asp Val Lys Ala His Leu Val Asn Ile
    1955            1960            1965

Ile His Glu Cys Val Lys Gln Thr Glu Ala Lys Pro Lys Pro Ile
    1970            1975            1980

Asn Leu Glu Arg Gly Phe Ala Thr Ile Pro Leu Lys Gly Ile Asp
    1985            1990            1995

Val Pro Phe His Ser Thr Phe Leu Arg Ser Gly Val Lys Pro Phe
    2000            2005            2010

Arg Ser Phe Leu Ile Lys Lys Ile Asn Lys Thr Thr Ile Asp Pro
    2015            2020            2025

Ser Lys Leu Val Gly Lys Tyr Ile Pro Asn Val Thr Ala Arg Pro
    2030            2035            2040

Phe Glu Ile Thr Lys Glu Tyr Phe Glu Asp Val Tyr Arg Leu Thr
    2045            2050            2055

Asn Ser Pro Arg Ile Ala His Ile Leu Ala Asn Trp Glu Lys Tyr
    2060            2065            2070

Glu Glu Gly Thr Glu Gly Gly Ser Arg His Gly Gly Thr Thr Ala
    2075            2080            2085

Ala Ser Ser
    2090
```